(12) United States Patent
Hernandez et al.

(10) Patent No.: US 12,128,004 B2
(45) Date of Patent: Oct. 29, 2024

(54) SYSTEMS AND METHODS FOR TREATING FLUID STASIS

(71) Applicant: Slipstream Solutions, LLC., Austin, TX (US)

(72) Inventors: Mark Hernandez, Austin, TX (US); Mateusz Gierdalski, College Station, TX (US); Steven S. Golden, Menlo Park, CA (US); James Lee, Los Gatos, CA (US)

(73) Assignee: Slipstream Solutions, LLC., Austin, TX (US)

( * ) Notice: Subject to any disclaimer, the term of this patent is extended or adjusted under 35 U.S.C. 154(b) by 0 days.

(21) Appl. No.: 18/665,969

(22) Filed: May 16, 2024

(65) Prior Publication Data

US 2024/0299234 A1    Sep. 12, 2024

Related U.S. Application Data

(63) Continuation of application No. PCT/US2023/073341, filed on Sep. 1, 2023.

(60) Provisional application No. 63/403,032, filed on Sep. 1, 2022.

(51) Int. Cl.
*A61H 9/00* (2006.01)

(52) U.S. Cl.
CPC ......... *A61H 9/0071* (2013.01); *A61H 9/0057* (2013.01); *A61H 2201/5056* (2013.01); *A61H 2201/5082* (2013.01); *A61H 2201/5092* (2013.01); *A61H 2209/00* (2013.01); *A61H 2230/655* (2013.01)

(58) Field of Classification Search
CPC .... A61H 9/0071; A61H 9/005; A61H 9/0057; A61H 2201/025
See application file for complete search history.

(56) References Cited

U.S. PATENT DOCUMENTS

| | | | | |
|---|---|---|---|---|
| 3,163,161 | A | * | 12/1964 | Courtin ............... A61H 9/0071 601/16 |
| 3,227,157 | A | * | 1/1966 | Courtin ............... A61H 9/0071 601/169 |
| 9,949,881 | B2 | | 4/2018 | Self et al. |
| 10,973,731 | B2 | | 4/2021 | Taskinen et al. |

(Continued)

FOREIGN PATENT DOCUMENTS

FR         2667247 A1 *  4/1992  ......... A61H 15/0092

OTHER PUBLICATIONS

"Lymphatic Drainage Massage", Cleveland Clinic, Sep. 2, 2021, 8 pages.

(Continued)

*Primary Examiner* — Joseph D. Boecker
*Assistant Examiner* — Thomas W Greig
(74) *Attorney, Agent, or Firm* — Kilpatrick Townsend & Stockton LLP

(57) ABSTRACT

Systems and methods for treating fluid stasis employ an airstream to move static fluid to one or more natural drainage areas for static fluid. A system for treating fluid stasis includes an airstream nozzle and an airflow generator for supplying an airflow to the airstream nozzle. The airflow nozzle is configured to output an airstream configured to be directed onto a patient to induce shear-thinning of static fluid and movement of static fluid toward one or more natural drainage areas for static fluid.

24 Claims, 31 Drawing Sheets

(56) References Cited

U.S. PATENT DOCUMENTS

2007/0173751 A1 7/2007 Ohashi et al.
2013/0296744 A1* 11/2013 Taskinen .................. A61H 7/00
601/11

OTHER PUBLICATIONS

PCT/US2023/073341, "International Search Report and the Written Opinion", Feb. 28, 2024, 15 pages.

* cited by examiner

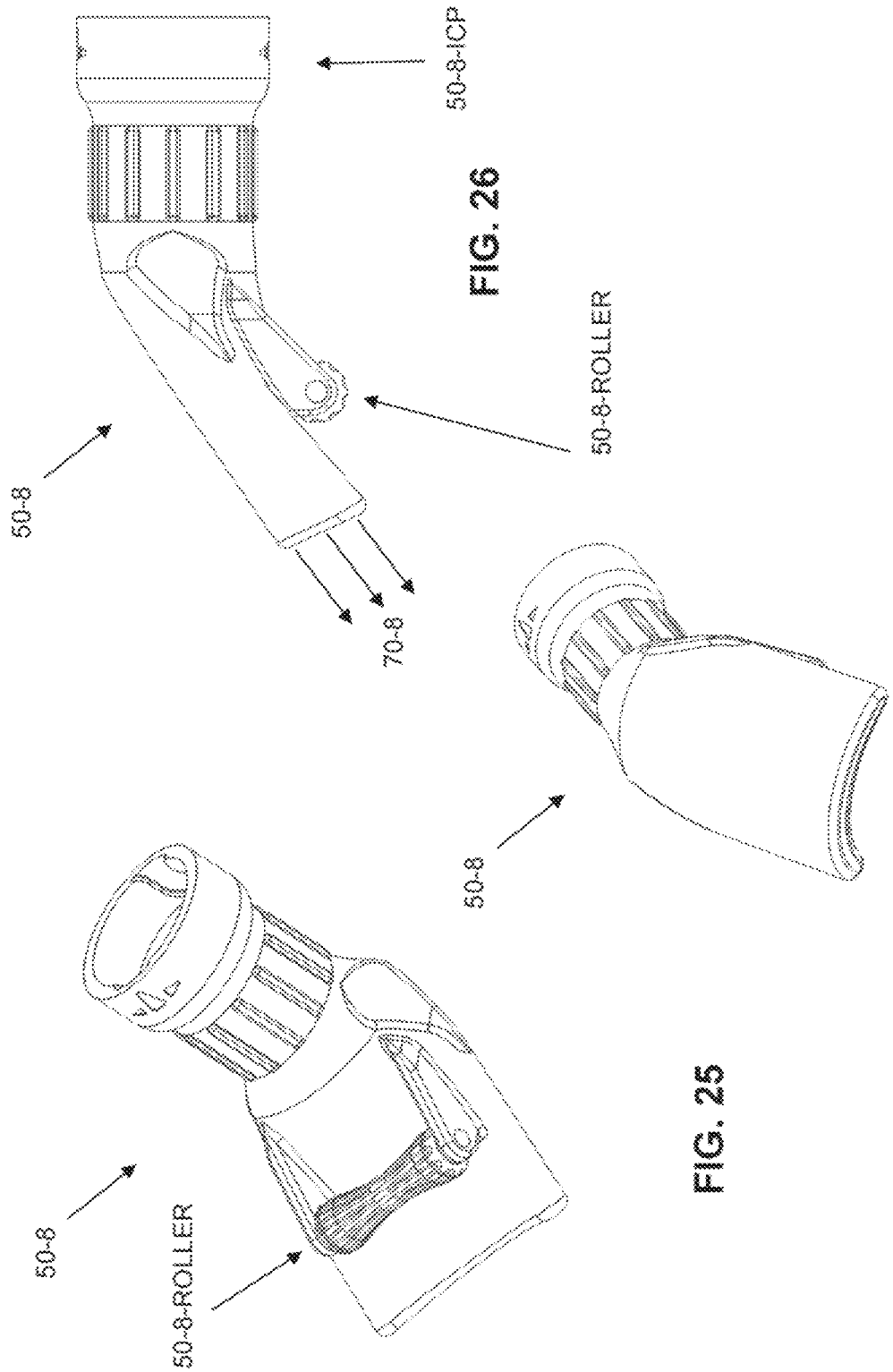

Airflow effect
hitting skin

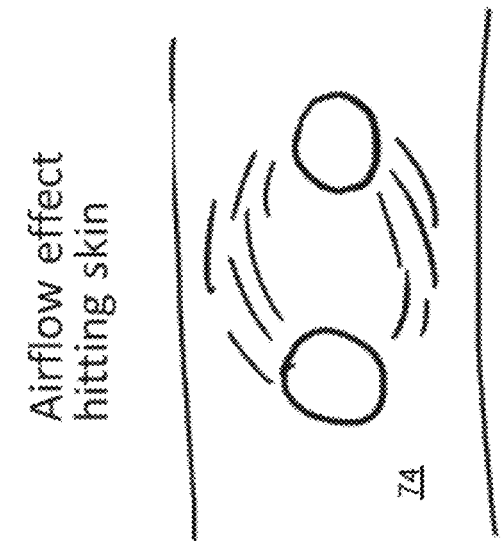
FIG. 41
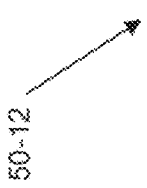
FIG. 42
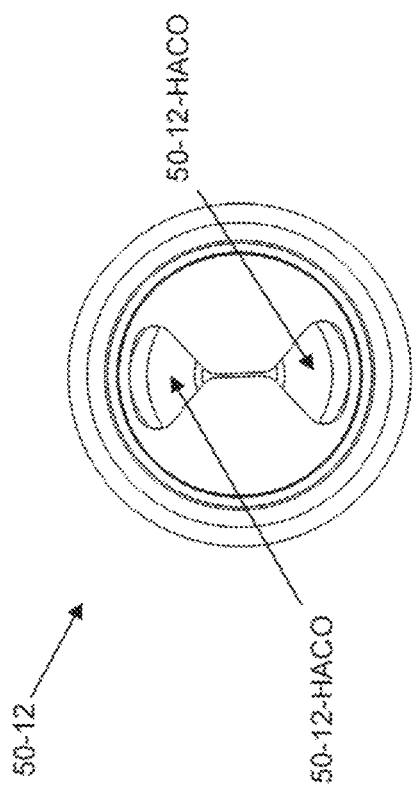
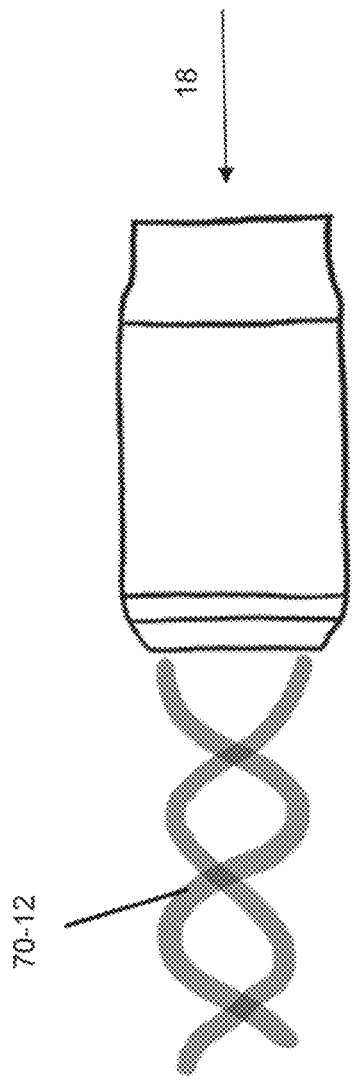
FIG. 43

SYSTEMS AND METHODS FOR TREATING FLUID STASIS

CROSS-REFERENCES TO RELATED APPLICATIONS

This application is a continuation of PCT Application No. PCT/US23/73341, filed on Sep. 1, 2023, which claims the benefit of and priority to U.S. Provisional Patent Application No. 63/403,032, filed Sep. 1, 2022, the entire contents of which are hereby incorporated by reference for all purposes in its entirety.

BACKGROUND

The lymphatic system is a fluid management system of the body, complementary to the blood circulatory system. Blood passing through capillaries naturally leaks out of the vascular bed to the surrounding tissues, primarily in the form of blood plasma, some of which permanently remains in the tissues moving throughout the tissue as interstitial fluid, delivering nutrients to cells. This interstitial fluid is collected by lymphatic vessels and passed through lymphatic nodes, where it is cleaned of cellular debris, bacteria, and other pathogens and finally returned to blood circulatory system. The lymphatic system plays an important dual function of combating infectious diseases as a part of immunological defenses and regulating tissue volume and pressure (e.g., via mitigating edema) by returning the interstitial fluid to the blood circulatory system.

Edema is a build-up of interstitial fluid in a tissue resulting in swelling (often visible) due to an overarching condition known as fluid stasis. Tissues are normally infused with interstitial fluid that is constantly moving through it and exchanged. When, however, fluid removal via the lymphatic system is impaired and/or fluid infiltration is increased (for example by anti-cancer therapy agents), accumulation of interstitial fluid may occur and induce different types of edemas, which can cause pain and discomfort for the patient and/or limit mobility of the affected area.

The presence of edema often negatively impacts outcomes of surgical interventions. Pre-operative edema can present due to co-existing conditions, such as from traumatic injury. Excessive mechanical stretching or compression of soft tissue often leads to extravasation of blood/blood plasma from capillaries and shifting intercellular fluid. Moreover, post-traumatic inflammation itself causes infiltration of lymphocytes to the affected region, adding to edema. Pre-operative edema is a recognized risk factor for developing post-operative infection, a major complication typically treated via antibiotic therapy and resulting in an extended period of healing. A recent study has shown that patients who suffer from lymphedema before a total hip arthroplasty have a 7.3% decrease in 5-year infection-free survival rate. Similar results have been observed for total knee arthroplasties, making pre-operative edema a concern for anyone soon to undergo surgery.

Even if a patient goes into a surgery in the best possible condition, the surgery itself is often traumatic to tissue. Surgery often involves the cutting of capillary vessels and lymphatic ducts and application of mechanical trauma on soft tissue and bones, which result in extravasation of fluids, inflammation, and finally edema. Postoperatively, edema (which is characterized by increased pressure in tissue and decreased fluid circulation) impedes removal of cellular debris and inhibits provision of growth factors, thereby impeding healing. Post-operative edema also decreases mobility of joints, which adds to the length of recovery and rehabilitation.

Inflammation, edema, and associated pain are poorly understood phenomena in medicine today and far too often treated by just prescribing medication, which only masks the pain and is often highly addictive. Other nonpharmaceutical solutions such as cold therapy and compression can be very uncomfortable and only temporarily effective. Today's active population is increasingly looking to get back to normal activities as soon as possible following surgery and other bodily injuries, but few effective, atraumatic, nonpharmaceutical options exist. A clear need exists for a major change in the way fluid stasis-related inflammation and edema are treated. Whether resulting from surgery, cancer treatment, injury, etc., the inflammation and fluid stasis must be mechanically addressed at their core in order to achieve immediate and lasting results without simply masking the symptoms. All together, these medical conditions represent a drain on the medical system in the US reaching into the billions of dollars. There has long been a need for treatments of fluid stasis that can effectively and efficiently bring patients back to their former selves.

Existing approaches and devices for treating fluid stasis-related edema include sequential compression devices, negative pressure devices, and manual massage. A compression devices are typically a full appendage device that apply peristaltic action to slowly move edematous fluid within a leg or arm proximally. Compression devices, however, may be unsuitable for treatment of fluid stasis in non-elongated portions of a patient, such as the head, armpits, hands, and shoulder areas. It is also possible for excess edematous fluid to build up around the proximal end of a compression device. Another drawback of compression devices can result due to lack of customization required to accommodate body size/type and individual needs of a patient. Compression devices can also be cumbersome to use, which may decrease patient compliance.

Taskinen et al. (U.S. Pat. No. 10,973,731) discloses a massage apparatus utilizing negative pressure to stimulate lymphatic fluids. A significant drawback to this type of technology is that it interacts with the body physically by pulling the skin up into a suction cup type apparatus, which can cause discomfort and damage to skin.

BRIEF SUMMARY

The following presents a simplified summary of some embodiments of the present technology in order to provide a basic understanding of some embodiments. This summary is not an extensive overview of the invention. It is not intended to identify key/critical elements of the invention or to delineate the scope of the invention. Its sole purpose is to present some embodiments in a simplified form as a prelude to the more detailed description that is presented later.

Systems and methods disclosed herein for the treatment of fluid stasis (e.g., edema) employ application of an airstream to a patient's skin to induce subsurface pressure changes that induce movement of static fluid toward one or more natural drainage regions for uptake/recycling of static fluid. The systems and methods disclosed herein may produce rapid visible results and provide for relatively painless drainage of vascular, lymphatic, and interstitial fluid buildup in tissue and vessels. The airstream can be applied to any externally exposed part of a patient, and the patient can be disposed in any suitable position (e.g., standing, prone, sitting, etc.). The system and methods described herein can be employed in a timely manner following surgery or traumatic injury. With some existing approaches that employ direct mechanical manipulation, it may take weeks for a surgical incision or an injury to be sufficiently healed to accommodate such direct mechanical manipulation without inducing excessive pain, discomfort, or dehiscence. Since the airstreams employed in the systems and methods described herein interact with the patient in a less traumatic manner than for direct mechanical manipulation, the systems and methods describe herein can be employed sooner, thereby decreasing post-operative/injury swelling and inflammation, leading to an expedited recovery. The systems and methods described herein may provide for movement of static fluid without physically touching the patient, which is particularly advantageous when treating patients with compromised skin, which may otherwise be injured with even gentle touching or direct manual manipulation.

Bodily fluids involved in creation of edema include blood, lymphatic fluids, and interstitial fluids (herein collectively referred to as "static fluid", recognizing that one or all of these fluids may not be fully static at any given time), each of which can be categorized as non-Newtonian fluids (which have a variable viscosity) and more specifically as shear-thinning type of non-Newtonian fluids (which have a viscosity that decreases with increased pressure). Due to trauma, illness, cancer treatments, or other reasons, these non-Newtonian fluids can thicken and become static, often resulting in edema. In many embodiments, the application of pressure changes and/or shear forces is used to decrease the viscosity of static fluids and induce movement of the less viscous fluid to known drainage areas.

Thus, in one aspect, a system for treating fluid stasis includes a directional airstream nozzle, an airflow hose, and an airflow generator. The directional airstream nozzle includes a directional airstream nozzle inlet configured to receive an airflow and a directional airstream nozzle outlet orifice configured to output a directional airstream generated from the airflow. The directional airstream is configured to be directed onto a skin of a patient to induce shear-thinning of static fluid and movement of static fluid toward one or more natural drainage areas for static fluid. The directional airstream nozzle outlet orifice has a directional airstream nozzle outlet orifice cross-sectional area. The airflow hose is configured for supplying the airflow to the directional airstream nozzle. The airflow generator is operable to generate and output the airflow to the airflow hose at a flow rate. A ratio of the flow rate to the directional airstream nozzle outlet orifice cross-sectional area is in a range from 0.004 $(m^3/min)/mm^2$ to 0.020 $(m^3/min)/mm^2$. The flow rate is at least 0.85 $m^3/min$. In many embodiments, the static fluid includes one or more of interstitial fluid, blood, or lymph fluid.

Flow parameters of the directional airstream can be controlled by the configuration of the directional airstream nozzle and the flow rate of the airflow. For example, in some embodiments, the flow rate is in a range from 1.3 $m^3/min$ to 7.1 $m^3/min$. In some embodiments, the airflow has a pressure in a range from 10,000 Pa to 35,000 pa within the directional airstream nozzle upstream of the directional airstream nozzle outlet orifice. In some embodiments, the directional airstream nozzle outlet orifice has a cross-sectional width and a cross-sectional length that is at least 2 times greater than a cross-sectional width. In some embodiments, the directional airstream nozzle outlet orifice is shaped to conform the directional airstream to a shape of an anatomical region of the patient treated.

In some embodiments, the directional airstream nozzle is configured for generating a zone of negative pressure under the directional airstream nozzle sufficient to lift the skin toward the directional airstream nozzle. For example, the directional airstream nozzle can be configured to form an external airflow channel that extends between the skin and the directional airstream nozzle through which a secondary airflow is drawn through via the airstream thereby creating the zone of negative pressure via the venturi effect.

The directional airstream nozzle can be configured to be pressed against the patient to directly apply pressure to the skin to shear thin and/or move static fluid. For example, in some embodiments, the directional airstream nozzle includes a lower surface protrusion shaped for application against the skin to apply pressure to the skin to shear thin and/or move static fluid. The lower surface protrusion can provide a lower side surface with a suitable shape (e.g., flat, convex, concave) complimentary to a typical shape of a targeted area of fluid stasis. In some embodiments, the directional airstream nozzle includes a roller configured to be rolled along the skin to apply a contact pressure to the skin to shear thin and/or move static fluid.

The directional airstream can be shaped to conform with the shape of an area being treated. For example, in some embodiments, the directional airstream nozzle outlet orifice has a curved shape configured to conform the directional airstream to a curvature of an arm or a leg.

The directional airstream nozzle can be configured to be interfaced with the patient to control a position and orientation of the directional airstream relative to the patient. For example, in some embodiments, the directional airstream nozzle includes longitudinally extending side skirts configured to form a negative pressure channel between the directional airstream nozzle and the skin in which a negative pressure is formed as a result of the directional airstream via the negative pressure channel functioning as a venturi.

The directional airstream nozzle can be configured for ease of application of the directional airstream to portions of a patient with limited space for the directional airstream nozzle, such as certain concave areas of a patient. For example, the directional airstream nozzle can have an upwardly curving distal portion that includes the directional airstream nozzle outlet orifice; the directional airstream nozzle can include an inlet portion having an inlet centerline; and the directional airstream can be directed transverse to the inlet centerline.

In some embodiments, the directional airstream nozzle is configured to shape the directional airstream for application to a substantially flat region of a patient. For example, in some embodiments, the directional airstream nozzle outlet orifice has flat oval cross-section.

The directional airstream nozzle can be configured to induce turbulence in the directional airstream. For example, the directional airstream nozzle can include a turbulence channel that receives the directional airstream from the directional airstream nozzle outlet orifice and is configured to induce turbulence in the directional airstream.

In many embodiments, the system for treating fluid stasis further includes a regional airstream nozzle configured for detachable mounting to the airflow hose. The regional airstream nozzle can include a regional airstream nozzle inlet configured to receive the airflow and a regional airstream nozzle outlet orifice configured to output a regional airstream generated from the airflow. The regional airstream can be configured to be directed onto the skin to induce shear-thinning of static fluid. In many embodiments, the regional airstream nozzle outlet orifice has a regional airstream nozzle outlet orifice cross-sectional area. In many embodiments a ratio of the flow rate to the regional airstream nozzle outlet orifice cross-sectional area is in a range from 0.004 (m$^3$/min)/mm$^2$ to 0.020 (m$^3$/min)/mm$^2$.

Flow parameters of the regional airstream can be controlled by the configuration of the regional airstream nozzle and the flow rate of the airflow. For example, in some embodiments, the flow rate is in a range from 1.3 $m^3/min$ to 7.1 $m^3/min$. In some embodiments, the airflow has a pressure in a range from 10,000 Pa to 35,000 pa within the regional airstream nozzle upstream of the regional airstream nozzle outlet orifice. In some embodiments, the regional airstream nozzle outlet orifice has a cross-sectional width and a cross-sectional length that is at least 2 times greater than a cross-sectional width. In some embodiments, the regional airstream nozzle outlet orifice is shaped to conform the directional airstream to a shape of an anatomical region of the patient treated. In some embodiments, the regional airstream nozzle outlet orifice has a flat oval shape. In some embodiments, the regional airstream nozzle includes a rotating assembly that generates a pulsatile component of the regional airstream. In some embodiments, the regional airstream nozzle includes a rotating assembly that generates a directionally varying component of the regional airstream. In some embodiments, the regional airstream nozzle includes an entrainment shell configured to incorporates a secondary airstream into the regional airstream.

In some embodiments, the system for treating fluid stasis is configured for measuring an extent of static fluid residing in an area of fluid stasis for use in assessing progress of a fluid stasis treatment. For example, the system for treating fluid stasis can further include a fluid sensor, an output device, and a control unit. The fluid sensor can be configured to generate a fluid sensor output signal indicative of an extent of static fluid within a tissue of the patient. The control unit can be configured to process the fluid sensor output signal to determine the extent of static fluid within the tissue. The control unit can be configured to control operation of the output device to output a feedback indicative of the extent of static fluid within the tissue. In some embodiments, the fluid sensor includes an impedance sensor.

In some embodiments, the system for treating fluid stasis includes an image sensor, an output device, and a control unit. The image sensor can be configured to generate skin movement image data for a region of the skin of the patient having induced movements resulting from directing the directional airstream onto the skin of the patient. The control unit can be configured to process the skin movement image data to estimate an extent of static fluid within a tissue underlying the region of the skin of the patient, wherein the control unit is configured to control operation of the output device to output a feedback indicative of the extent of static fluid within the tissue.

In another aspect, a method of treating fluid stasis is provided. The method includes outputting a directional airstream from a directional airstream nozzle onto a skin of a patient to shear-thin static fluid and move static fluid toward one or more natural drainage regions for static fluid. In many embodiments, the static fluid includes one or more of interstitial fluid, blood, or lymph fluid. In many embodiments, the method includes moving the directional airstream nozzle toward the one or more natural drainage regions for static fluid one or more times. In many embodiments, the directional airstream nozzle is configured and oriented so that an angle between a direction of the directional airstream leaving the directional airstream nozzle and the skin is in a range from 0 degrees to 60 degrees. In some embodiments of the method, a ratio of a flow rate of the directional airstream to a directional airstream nozzle outlet orifice cross-sectional area of the directional airstream nozzle is in a range from 0.004 $(m^3/min)/mm^2$ to 0.020 $(m^3/min)/mm^2$ and the flow rate is at least 0.85 $m^3/min$. In some embodiments, the directional airstream nozzle is not contacted with the skin of the patient.

In many embodiments of the method, the directional airstream has an elongated cross-sectional shape to interact with a corresponding elongated portion of the skin. For example, in some embodiments of the method, the directional airstream nozzle includes a directional airstream nozzle outlet orifice for the directional airstream having a directional airstream nozzle outlet orifice area having a length that is at least 2 times longer than a width of the directional airstream nozzle outlet orifice area. In some embodiments of the method, the directional airstream nozzle outlet orifice area is shaped to conform the directional airstream to a shape of an anatomical region of the patient treated.

In some embodiments of the method, the directional airstream nozzle is configured for generating a zone of negative pressure under the directional airstream nozzle sufficient to lift the skin toward the directional airstream nozzle. For example, the directional airstream nozzle can be configured to form an external airflow channel that extends between the skin and the directional airstream nozzle through which a secondary airflow is drawn through via the airstream thereby creating the zone of negative pressure via the venturi effect.

In many embodiments, the method further includes assessing progress of the treatment. For example, the method can include assessing movement of the skin induced by the directional airstream to determine when the skin has a degree of pliability indicative of a desired amount of static fluid having been moved toward the one or more natural drainage regions.

In many embodiments, the method further includes outputting a regional airstream from a regional airstream nozzle onto the skin to condition the one or more natural drainage regions for uptake of static fluid. In some embodiments of the method, the regional airstream includes a pulsatile component or a directionally varying component. In some embodiments of the method, the regional airstream induces rotation of a rotatable component of the regional airstream nozzle and the rotation of the rotatable component induces the pulsatile component or the directionally varying component.

In many embodiments, the method further includes outputting a regional airstream from a regional airstream nozzle onto the skin to shear-thin static fluid. In some embodiments of the method, the regional airstream includes a pulsatile component or a directionally varying component.

In many embodiments of the method, the directional airstream nozzle is configured to be pressed against the patient to directly apply pressure to the skin to shear thin and/or move static fluid. For example, in some embodiments of the method, the directional airstream nozzle includes a lower surface protrusion shaped for application against the skin to apply pressure to the skin to shear thin and/or move static fluid. The lower surface protrusion can provide a lower side surface with a suitable shape (e.g., flat, convex, concave) complimentary to a typical shape of a targeted area of fluid stasis. In some embodiments of the method, the directional airstream nozzle includes a roller configured to be rolled along the skin to apply a contact pressure to the skin to shear thin and/or move static fluid.

In many embodiments, the method includes providing feedback indicative of an amount of static fluid within the treated tissue. For example, the method can include: (a) generating, by a fluid sensor, a fluid sensor output signal indicative of an extent of static fluid within a treated tissue of the patient; (b) processing the fluid sensor output signal to determine the extent of static fluid within the treated tissue; and (c) outputting a feedback indicative of the extent of static fluid within the treated tissue. In many embodiments of the method, the fluid sensor includes an impedance sensor. In some embodiments, the method includes: (a) generating, via an image sensor, skin movement image data for a region of the skin of the patient having induced movements induced by the directional airstream; (b) processing the skin movement image data to estimate an extent of static fluid within a tissue underlying the region of the skin of the patient; and (c) outputting a feedback indicative of the extent of static fluid within the tissue underlying the region of the skin of the patient.

In some embodiments, the method includes inducing turbulence in the directional airstream within a turbulence chamber of the directional airstream nozzle. For example, the directional airstream nozzle can include a turbulence channel that receives the directional airstream from the directional airstream nozzle outlet orifice and is configured to induce turbulence in the directional airstream.

In some embodiments, the method includes generating, via the directional airstream, a zone of negative pressure under the directional airstream nozzle sufficient to lift the skin toward the directional airstream nozzle. For example, the directional airstream nozzle can be configured to form an external airflow channel that extends between the skin and the directional airstream nozzle through which a secondary airflow is drawn through via the airstream thereby creating the zone of negative pressure via the venturi effect.

For a fuller understanding of the nature and advantages of the present invention, reference should be made to the ensuing detailed description and accompanying drawings.

BRIEF DESCRIPTION OF THE DRAWINGS

FIG. 25, FIG. 26, and FIG. 27 show views of a roller nozzle having a roller configured to be contacted with a patient to apply direct mechanical compression in combination with an airstream output from the roller nozzle for application to the patient to induce compressive shear thinning, stimulation, and directional movement of static fluid, in accordance with embodiments.

FIG. 41, FIG. 42, FIG. 43, and FIG. 44 illustrate a dual helical output nozzle configured to output a rotating dual helical airstream for application to a patient to induce compressive shear thinning, stimulation, and directional movement of static fluid, in accordance with embodiments.

DETAILED DESCRIPTION

Figure 1:
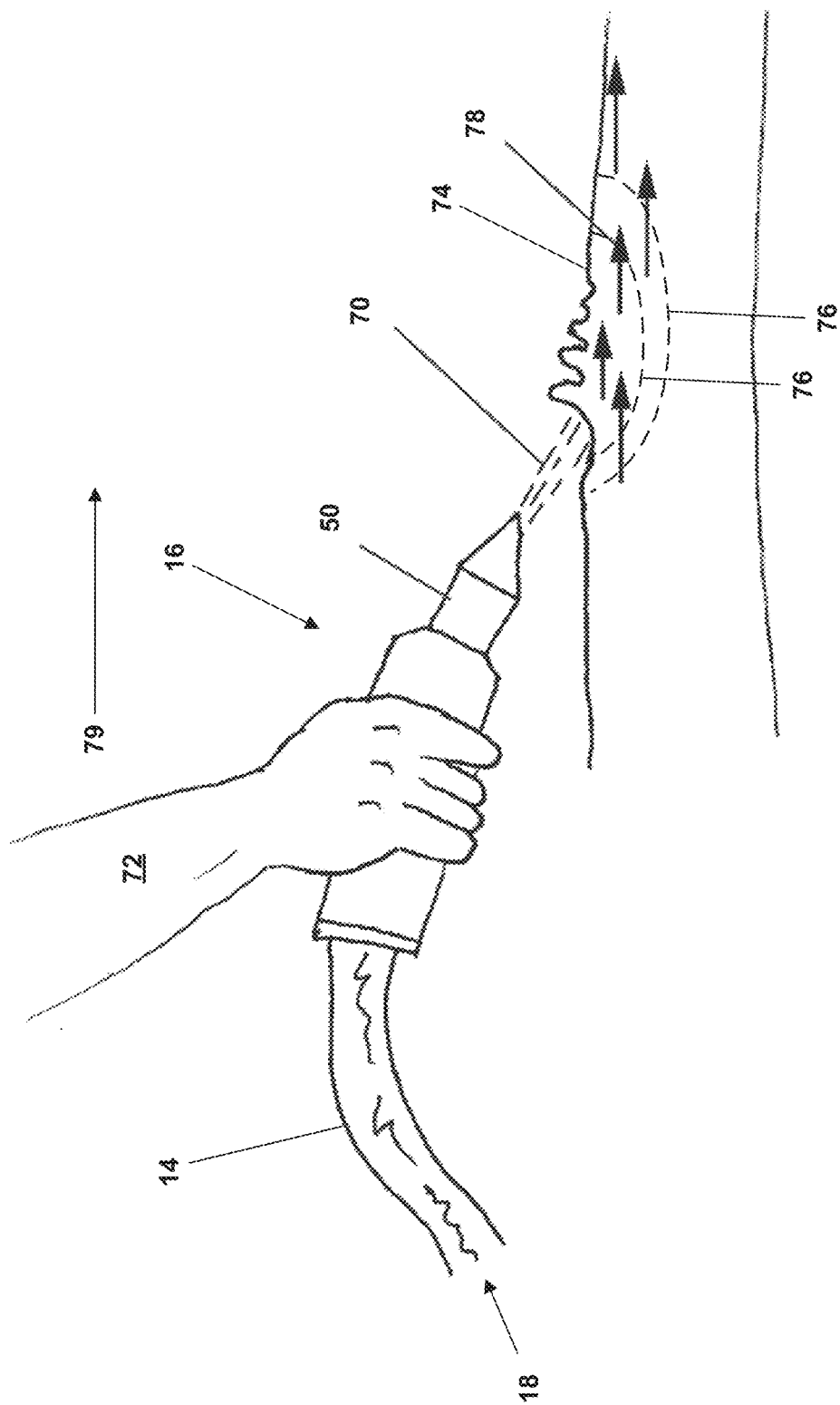
FIG. 1 illustrates directional application of an airstream to induce shear thinning of static fluid and induce movement of static fluid toward one or more lymphatic nodes, one or more drainage points, and/or the heart, in accordance with embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

In many embodiments, systems and methods described herein for treatment of fluid stasis (e.g., edema) employ a forced-air flow device to generate an airstream that is discharged from a treatment nozzle onto the skin of a patient to induce subsurface pressure changes that decrease the viscosity of static fluid and induce movement of static fluid to known naturally occurring drainage areas. The systems and methods described herein can be selectively and efficiently applied to various parts of the body to provide for treatment of fluid stasis by thinning and moving static fluid. One or more fans can be employed to generate an airflow that is transmitted to a nozzle via an airflow hose. In many embodiments, various specially configured nozzles can be selectively employed to generate corresponding specialized airstreams for incident on the patient's skin as described herein. As described herein, one or more feedback mechanisms can be employed to provide information indicative of the extent of static fluid movement and/or how much static fluid remains to be moved via continued treatment. An airflow generating device can be configured to control one or more parameters of the airflow, such as temperature, flow rate, and/or pulsation, and include suitable input devices for specifying the value of each of the one or more parameters of the airflow. The specially configured nozzles can be detachably mountable to the hose for selective use based upon the area of the patient being treated and specific type of treatment. The systems and methods described herein can be employed using the approaches described herein to further facilitate and optimize treatment of fluid stasis (e.g., edema) via movement of static fluid to one or more natural drainage areas within a patient's body.

The system and methods described herein have broad application in management of fluid stasis and various edemas. Some of those applications include lymphedema; pre- and post-operative edemas (particularly edemas resulting from orthopedic procedures); acute or chronic soft tissue injury edema; peripheral vascular and neurological conditions such as gout; inflammatory dermatological conditions; systemic edemas, fibromyalgia, and other inflammatory disorders. Stasis of fluids containing anti-cancer therapy agents (chemo), particularly in the extremities is an application that may or may not explicitly involve edema. Other non-edematous applications include athletic recovery, evaporative cooling, and fever/high body temperature management. In the case of athletic recovery, the system and methods disclosed herein may also be effective for clearance of lactic acid and other byproducts of athletic exertion. The system and methods disclosed herein may also be effective for clearance of chemotherapy agents and other therapeutics from the distal extremities to prevent pain, peripheral neuropathy, and skin dermatological conditions associated with accumulation of such agents. The foregoing list of applications for the systems and methods described herein is intended to be partial, demonstrating some non-limiting examples of the wide range of applications in fluid stasis (e.g., edema) management for the system and methods disclosed herein.

Various methods are proposed herein for providing efficient, comfortable, convenient, and effective treatment of edemas and fluid stasis. In an embodiment, a method includes application of a regional shear-thinning force from outside the body directly over the clavicular regions (thoracic duct and subclavian vein on the left; lymphatic duct, and subclavian vein on the right) in order to stimulate and decrease the viscosity of blood, lymph, and interstitial fluid, and stimulate the lymphatic system. The regional shear-thinning force is generally provided by the system in the form of a column of high-velocity air, which primes the lymphatic/venous interface (at the above-mentioned locations) for efficient flow. The method can further include directional application of an airstream onto the skin to further facilitate shear thinning and movement of static fluids directionally in relation to the anatomical course of the lymphatic and vascular pathways. The method can also include application of directional sweeping of an airstream to the skin in specific patterns/directions in accordance with the lymphatic drainage protocol and vascular pathways for the bodily region being treated. In many embodiments, the airstream is customized by a shaped nozzle and directionally applied to the skin.

Movement of static fluid as described herein flushes or influences local concentrations of various cytokines, vaso-regulating substances, and other pain-regulating substances, which helps to restore local tissue homeostasis. These aforementioned chemical substances exist in the occurrence of inflammatory interstitial stasis, colloquially known as an "inflammatory soup", which is commonly the root cause of pain, inflammation, and prolonged recovery in patients with fluid stasis. Such restoration of local tissue homeostasis may help reduce swelling and edema, reduce pain, and accelerate recovery.

Approaches for treating fluid stasis (e.g., edema) in specific areas of the body are described herein. For example, in many embodiments, a method for treatment of fluid stasis in upper extremities initially employs a regional application of an airstream to the upper chest/lower neck area beneath clavicle where lymph nodes are located and lymphatic drainage naturally occurs. This is followed by a directional application of an airstream onto the extremity consistent with natural lymphatic drainage pathways. The regional application of the airstream can employ an airstream that interacts with the skin to apply regional compressive forces to the skin over any suitably shaped area (e.g., round, elongated oval, square, rectangle). The applied regional compressive forces may be applied using a forced air system as described herein to apply an airstream to the skin that is directed substantially perpendicular to the skin (e.g., at angles greater than 45 deg). The regionally applied airstream can be applied to the skin in any suitable specific bodily region to actively reduce the viscosity (shear-thin) underlying static fluid. Alternately, regional compressive forces may be applied manually by the therapist using a compressive massage technique or other compressive tools. Subsequent to application of regional compressive forces, the system may be configured with another nozzle suited to provide an airstream shaped to conform to an external shape of a portion of the patient being treated. For example, the airstream can have an elongated blade configuration having an elongated cross-sectional length or arc length and a narrower cross-sectional thickness transverse to the cross-sectional length or arc length. Regardless of the nozzle employed, an airstream can be applied directionally to the skin at an angle (e.g., less than 90 degrees from parallel with the skin) to facilitate directional movement of static fluid in the general direction of the directionally applied airstream. The directionally applied airstream can also produce wave-like movements of the skin. The directionally applied airstream can be applied so that a deployment zone of the airstream on the skin is moved along the skin directionally any suitable number of times to induce movement of static fluid along the lymphatic and vascular pathways. For example, when treating upper extremities, such as the hand or fingers, static fluid can be pushed (via movement of the deployment zone of the airstream on the skin) first over the palm area of the hand to the distal fingertips and between the fingers. Static fluid can then be pushed (via movement of the deployment zone of the airstream on the skin) down the back side of the fingers/hand, continually sweeping static fluid up the arm proximally toward the lymph axillary and other lymph nodes for drainage of static fluid. Additional nozzles may be employed (further described below) to move static fluid through specific anatomy, such as the fingers, where a shorter, narrower nozzle outlet with a tighter radius may be utilized.

Fluid stasis (e.g., fluid stasis) of the lower extremities may be treated by regional application of an airstream to apply regional compressive forces over inguinal lymph nodes followed by regional application of an airstream to apply regional compressive forces to the leg and foot area as well to stimulate and shear-thin static fluid. In the case of treatment of the foot area, a smaller foot-specific nozzle may then be attached to output a higher velocity stream of air incident on the foot area. The smaller foot-specific nozzle, in combination with sweeping movements of a zone of incidence of the higher velocity stream of air with the foot, can be used to move static fluid starting at the bottom/sole of the foot and pushing static fluid distally toward the toes and subsequently around and between the toes to the top side of the foot. Static fluid may then be compelled with sweeping motions of the zone of incidence up the leg and into known drainage areas in the inguinal region.

The systems and methods described herein can also be applied to treat fluid stasis (e.g., edema) in other areas (e.g., head/neck, thorax/abdomen, pelvic floor) using the approaches described herein. In all cases, an airstream can be regionally applied to induce stimulation of fluid movement pathways and/or shear-thinning of static fluid in combination with directional application of an airstream to induce movement of static fluid of the stasis area along lymphatic and vascular pathways.

Regional application and/or directional application of airstreams to skin can be accomplished to produce wave-like movements of the skin. Such wave-like movements may serve to enhance both shear-thinning of static fluid and well as enhance the movement of static fluid in a desired direction. The wave like motions of the skin have been observed to become more pronounced as the viscosity and/or volume of static fluid local to the zone of deployment of the airstream on the skin is reduced. For example, application of an airstream to an area of the body with significant fluid stasis produces very few waves. The skin and underlying tissues and static fluid are not moving well and thus produce no waves. With continued application of an airstream, static fluid thins and the tissue local to the zone of deployment of the airstream become more supple and exhibit increasing levels of wave-like movements. Accordingly, the magnitude of wave-like movements of the skin local to the deployment zone of the airstream on the skin provides feedback to the operator/therapist regarding the progress of moving static fluid out of the fluid stasis area.

Turning now to the drawing figures, in which similar reference identifies are used to designate similar elements in the various figures, FIG. 1 illustrates directional application of an airstream 70 to induce shear thinning of static fluid and directional movement of static fluids in a direction 78 out of an area of fluid stasis along lymphatic and vascular pathways toward one or more lymphatic nodes, one or more drainage points, and/or the heart, in accordance with embodiments. In the illustrated embodiment, the directional application of the airstream 70 is output from a nozzle 50 of a nozzle assembly 16 held and manipulated by an operator 72 to direct the airstream 70 onto the skin 74 of a patient to apply compressive forces to the skin 74 to generate subsurface pressure changes 76. The nozzle 50 is attached to an airflow supply hose 14, which delivers an airflow to the nozzle 50 from a main unit 22 (shown in FIG. 45). The subsurface pressure changes 76 include subsurface pressure increases that produce shear-thinning of static fluid within the tissue, which increases the mobility of static fluid through the tissue. The airstream 70 is oriented non-perpendicular to the skin 74 so that the airstream 70 has a component directed along the skin 74 in a direction of desired movement of static fluid through the tissue. The airstream 70 can be oriented relative to the skin 74 to apply both compressive forces to the skin 74 and to generate wave-like movements of the skin 74, which may serve to increase variability of the subsurface pressure changes 76 and thereby increase motive force applied to move static fluid through the tissue. Static fluid can be pushed out of the fluid stasis area via movement of the area of deployment of the airstream 70 along the skin 74 via corresponding movement of the nozzle 50 by the operator 72. The movement of the area of deployment results in corresponding movement of the subsurface pressure changes 76, which serves to push static fluid in the direction 78 of movement of the subsurface pressure changes 76. The nozzle 50 can be repeatedly moved along the skin 74 in a direction 79 (corresponding to direction 78) to move the subsurface pressure changes 76 through the tissue to move static fluid along lymphatic and vascular pathways.

Figure 2:
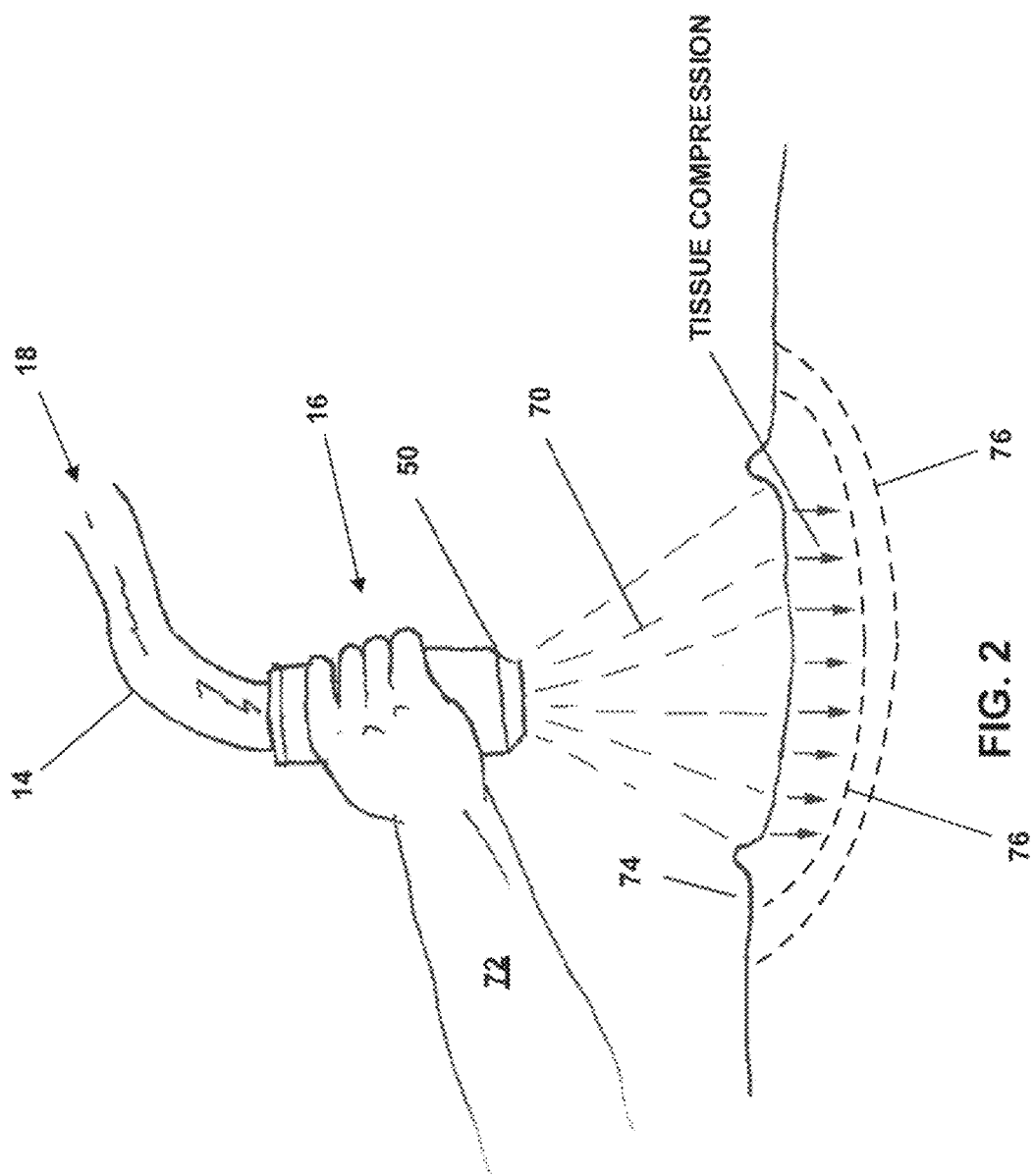
FIG. 2 illustrates application of an airstream to induce shear thinning of static fluid and/or stimulate/condition one or more lymphatic nodes, one or more lymphatic ducts, and/or blood vessels for transport and/or uptake of static fluid, in accordance with embodiments.

FIG. 2 illustrates a regional application of an airstream 70 primarily to induce shear thinning of static fluids and/or stimulate/condition one or more lymphatic nodes, one or more lymphatic ducts, and/or blood vessels for transport and/or uptake of static fluid, in accordance with embodiments. In the regional application of the airstream 70, the airstream can be oriented substantially perpendicular to the skin 74 in contrast to the directional application illustrated in FIG. 1, thereby applying increased compressive forces to the skin 74 relative to the directional application of the airstream 70 illustrated in FIG. 1. The increased compressive forces applied cause corresponding increased magnitudes of the subsurface pressure changes 76. Increased magnitudes of the subsurface pressure changes 76 may induce greater reduction in viscosity of static fluid and greater level of stimulation/conditioning of the one or more lymphatic nodes, the one or more lymphatic ducts, and/or the blood vessels for transport and/or uptake of static fluid.

The airstream 70 can be output from the nozzle 50 at any suitable volumetric flow rate relative to nozzle outlet area. The suitable ratio of volumetric flow rate to nozzle outlet area (in units of ($m^3$/min) to $mm^2$) can be in the range from 0.004 to 0.020, more preferably in a range from 0.009 to 0.014.) The nozzle 50 can have any suitable outlet opening area with a minimum area of 113 $mm^2$ to any max area suitable for treating the body as long as the ratio of volumetric flow rate to nozzle outlet meets the stated suitable ratio. The current preferred therapeutic nozzle opening area is in a range from 300 to 700 $mm^2$. The airstream 70 can be configured for application to any particular area of a patient via selection and use of the nozzle 50 from a collection of nozzles (such as described herein). In embodiments, an airflow supplied to the nozzle 50 and output from the nozzle 50 as the airstream 70 is filtered using a high efficiency particulate air (HEPA) filter.

Figure 3:
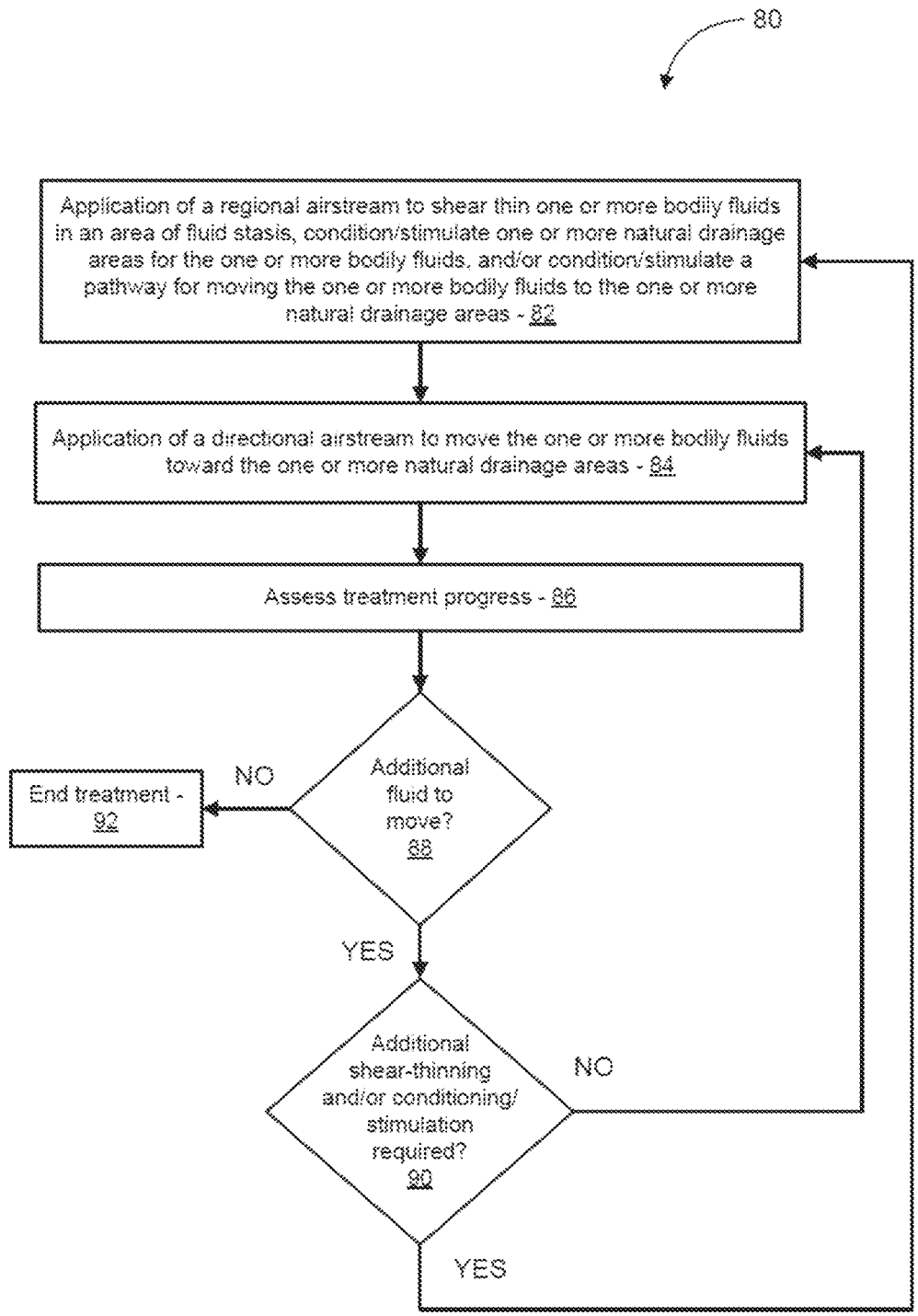
FIG. 3 is a simplified block diagram of a method of treating fluid stasis, in accordance with embodiments.

FIG. 3 is a simplified block diagram of a method 80 of treating fluid stasis, in accordance with embodiments. Method 80 can be practiced using any suitable systems and/or fluid movement routes within a patient, such as those described herein.

In act 82, an airstream is regionally applied to a patient's skin (e.g., as illustrated in FIG. 2 and discussed with reference to FIG. 2) to condition/stimulate a fluid movement pathway and/or a drainage area(s) (e.g., lymphatic nodes(s), lymphatic duct(s), and/or circulatory system) within the patient to enhance movement and uptake of static fluid moved out of an area of fluid stasis within the patient and/or along a fluid movement pathway.

In act 84, an airstream is directionally applied to a patient's skin (e.g., as illustrated in FIG. 1 and discussed with reference to FIG. 1) to induce shear thinning of static fluid and movement of static fluid out of an area of fluid stasis along a fluid movement pathway to one or more uptake areas for static fluid (e.g., one or more lymphatic nodes, one or more drainage points). As discussed herein, static fluid can be pushed out of the fluid stasis area via movement of the airstream 70 along the skin 74. The nozzle 50 can be repeatedly moved along the skin 74 to move the subsurface pressure changes 76 through the tissue to move static fluid along the lymphatic drainage pathway.

After (and during) the directional application of the airstream in act 84, the progress of the treatment can be assessed (act 86). In many embodiments, the assessment of progress of the treatment includes determining progress of movement of static fluid out of the area of fluid stasis, progress of movement of static fluid along a fluid movement pathway to one or more collection/uptake areas for static fluid, amount of static fluid remaining in the fluid stasis area, and/or amount of static fluid remaining in the fluid movement pathway. The assessment of the progress of the treatment can employ any suitable feedback, the most basic of which is visual. For example, the appearance and increase in the size and frequency of the tissue waves is an important feedback mechanism for assessing progress of the treatment. When fluid in a body part is static (for example, when edema is present), the tissue is typically stiffer and resists movement. Tissue waves created by the airstream when the tissue is stiff and resists movement are generally muted or nonexistent. As the treatment method 80 is accomplished, static fluid thins and begin to move out of the area of fluid stasis and may be replaced by fresh fluid, which increases pliability of tissue/skin thereby increasing the extent of wave-like movements of the skin in response to the application of the airstream. In some embodiments, one or more video monitoring sensors are integrated as part of the system to generate one or more video sensor outputs indicative of movement of the skin in the area of deployment of the airstream. A system configured for application of the treatment method 80 (e.g., a system for treating fluid stasis (e.g., edema) described herein) can include a control unit configured to process the one or more video sensor outputs to generate and output a feedback indicative of the extent of wave-like movements of the skin for use in assessing the progress of the treatment. In some embodiments, one or more photoplethysmography (PPG) sensors may be used to assess the status of the fluid stasis condition and thus aid in determining the need for further treatment. In some embodiments, one or more bio-impedance sensors may be used to assess the status of the fluid stasis condition and thus aid in determining the need for further treatment. In some embodiments, one or more ultrasound transducers may be used to assess the status of the fluid stasis condition and thus aid in determining the need for further treatment. Yet other embodiments may employ feedback sensors such as temperature/heat mapping sensors for use in generating feedback indicative of real time vascular activity levels, which may be indicative of treatment progress. For example, when using a forward looking infrared camera (FLIR), high perfusion areas present a stronger heat signature which is easily distinguishable from the less perfused areas. These aforementioned sensors may be integrated into the nozzle or integrated with the system as separate components. One or more ultrasound transducers or video sensors may also be integrated so as to provide user feedback regarding proper proximity of the nozzle to the treatment area so as to provide optimal treatment. The user may then use any of this feedback to inform their decision as to treatment continuation or cessation.

Based on the assessment accomplished in act 86, a decision can be made whether there is additional static fluid to be moved during the treatment (act 88). If there is no additional static fluid to be moved during the treatment, the treatment can be ended (act 90). If there is additional static fluid to be moved during the treatment, the method 80 can proceed to determining whether additional stimulation and/or conditioning of the fluid pathway is required. If additional stimulation and/or conditioning of the fluid pathway is required, method 90 can loop back to act 82 to accomplish additional stimulation and/or conditioning of the fluid pathway. If no additional stimulation and/or conditioning of the fluid pathway is required, the method 80 can be loop back to act 84 to induce additional shear thinning of static fluid and directional movement of static fluid out of an area of fluid stasis along a fluid movement pathway to one or more uptake areas for static fluid. To determine if additional treatment is required, one knowledgeable in the art will be able to visibly distinguish between the pre-treatment tissue condition versus post-treatment tissue condition. Lack of further change to tissue condition would indicate to the user to modify treatment or to stop treatment. In embodiments, feedback sensors will be able to detect relative parameters pre and post-treatment and indicate to the user that they should repeat or end the treatment.

Fluid Movement Pathways

The systems and methods described herein can be employed to move static fluid along any suitable fluid movement pathway to move static fluid out of an area of fluid stasis to one or more uptake areas for static fluid. For example, some suitable fluid pathways for static fluid are illustrated in FIG. 4 through FIG. 10.

Figure 4:
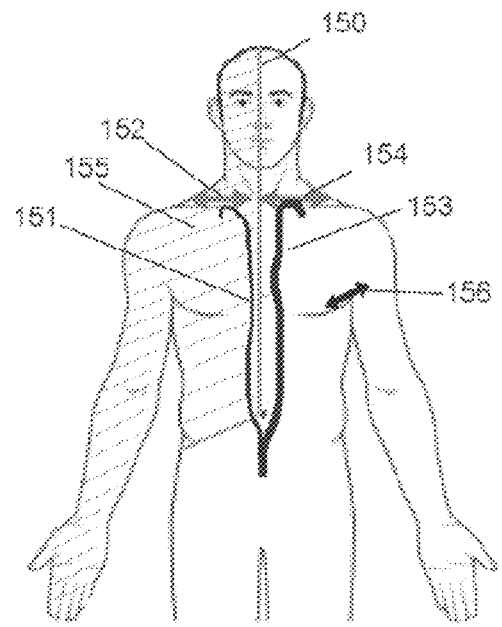
FIG. 4 shows a schematic diagram of the human body illustrating areas for compressive shear thinning, stimulation, and directional movement of static fluid for the general torso area via airstream application, in accordance with embodiments.

FIG. 4 shows a schematic diagram of the human body illustrating areas for compressive shear thinning, stimulation, and directional movement of static fluid for the general torso area via airstream application, in accordance with embodiments. The upper torso area houses a majority of the drainage points for lymphatic and interstitial fluid. While the human body is symmetrical phenotypically, the lymphatic vessels and drainage system are different on either side of the sagittal midline 150. The right lymphatic duct 151 on the right side of the body and the thoracic duct 153 on the left side of the body empty into the right subclavian vein (located under the right-side clavicle bone) and the left subclavian vein (located under the left-side clavicle bone), respectively. The right lymphatic duct 151 and subsequently the right subclavian vein receives lymphatic and interstitial fluid from the right head and neck area, right trunk and abdomen, and right arm, as represented by the hatched area 155. The lymphatic fluid from the remainder of the body (not hatched) dumps into the thoracic duct 153 and subsequently the left subclavian vein. In view of the differences of the lymphatic vessels and drainage system on either side of the sagittal midline 150, the approaches described herein for drainage of static fluid are different for certain anatomically symmetric areas of the body.

With continued reference to FIG. 4, act 82 of method 80 can be accomplished via regional application of the airstream 70 to the area over major drainage points 152, 154 (designated by the thick arrows in FIG. 4). While the regional application of the airstream 70 can be accomplished using any suitable nozzle, such as any of the nozzles describe herein, some of the nozzle described herein (such as the round nozzle 50-1 illustrated in FIG. 11 and FIG. 12, the entrainment nozzle 50-2 illustrated in FIG. 13, the pulsation nozzle 50-10 illustrated in FIG. 31 through FIG. 34, the helical output nozzle 50-11 illustrated in FIG. 35 through FIG. 40, and the dual helical output nozzle 50-12 illustrated in FIG. 41 through FIG. 44) may be especially suited for use in generating the airstream 70 for the regional application of the airstream in act 82 of the method 80. In act 82 of method 80, the nozzle can be oriented relative to the body so that the airstream 70 is incident on the body substantially perpendicular to the body. The distance between the output of the nozzle and the skin 74 can be in a range from 0 cm to 50 cm depending upon the state of fluid stasis and skin integrity. In some regional applications of the airstream 70, a preferred distance between the output of the nozzle and the body during the regional application of the airstream 70 in act 82 of the method 80 is in a range from 10 cm to 30 cm. The nozzle can be moved laterally back and forth across areas 152, 154 (including just above and below the clavicle) to compress and thin as much static fluid as possible and stimulate the drainage areas. The regional application of the airstream to areas 152, 154 can be used to effectively unclog and prepare areas 152, 154 for subsequent receipt of static fluid moved to the areas 152, 154 using the approaches described herein. The regional application of the airstream 70 can be repeated for the right side of the body, particularly if the fluid stasis area to be treated is disposed in the right arm or right side of the torso. Also, the left axillary region 156, which houses large lymph nodes which the rest of the body drain to, can be stimulated via regional application of the airstream 70 in accordance with act 82 of the method 80.

FIG. 5 through FIG. 10 illustrate fluid movements paths that can be used to practice act 84 of method 80 to treat fluid stasis (e.g., edema) in corresponding portions of a patient. As described herein, method 80 includes act 82, which can be used for: (1) conditioning and stimulation of one or more drainage areas and shear thinning of static fluid within the one or more drainage areas, and/or (2) conditioning and stimulation of an area of fluid stasis to be treated and shear thinning of static fluid within the area of fluid stasis to be treated. Method 80 also includes act 84, which can be used to directionally move static fluid to a drainage area for static fluid along any suitable fluid movement path (e.g., any of the regional fluid movement paths illustrated in FIG. 5 through FIG. 10 via which static fluid can be moved from the fluid stasis area to the fluid drainage area). While the directional application of the airstream 70 employed in act 84 of method 80 can be accomplished using any suitable nozzle, such as any of the nozzles describe herein, some of the nozzle described herein (such as the flat oval nozzle 50-3 illustrated in FIG. 14 and FIG. 15, the curved blade nozzle 50-4 illustrated in FIG. 16 and FIG. 17, the extended curved blade nozzle 50-5 illustrated in FIG. 18 and FIG. 19, the upturned nozzle 50-6 illustrated in FIG. 21, the bump nozzle 50-7 illustrated in FIG. 23 and FIG. 24, the roller nozzle 50-8 illustrated in FIG. 25 through FIG. 27, the hooded nozzle 50-9 illustrated in FIG. 28 and FIG. 29, the pulsation nozzle 50-10 illustrated in FIG. 31 through FIG. 34, the helical output nozzle 50-11 illustrated in FIG. 35 through FIG. 40, and the dual helical output nozzle 50-12 illustrated in FIG. 41 through FIG. 44) may be especially suited for use in generating the airstream 70 for the directional application of the airstream in act 84 of the method 80. As described herein, the directional application of the airstream in act 84 of the method 80 can be accomplished via any suitable number of sweeping movements of the area of deployment of the airstream 70 over the skin 74 of the patient in a direction aligned with the fluid movement pathway employed. The sweeping motions can include long sweeps over the length of the affected area and/or short sweeps, depending on the location of the fluid stasis area being treated.

Figure 5:
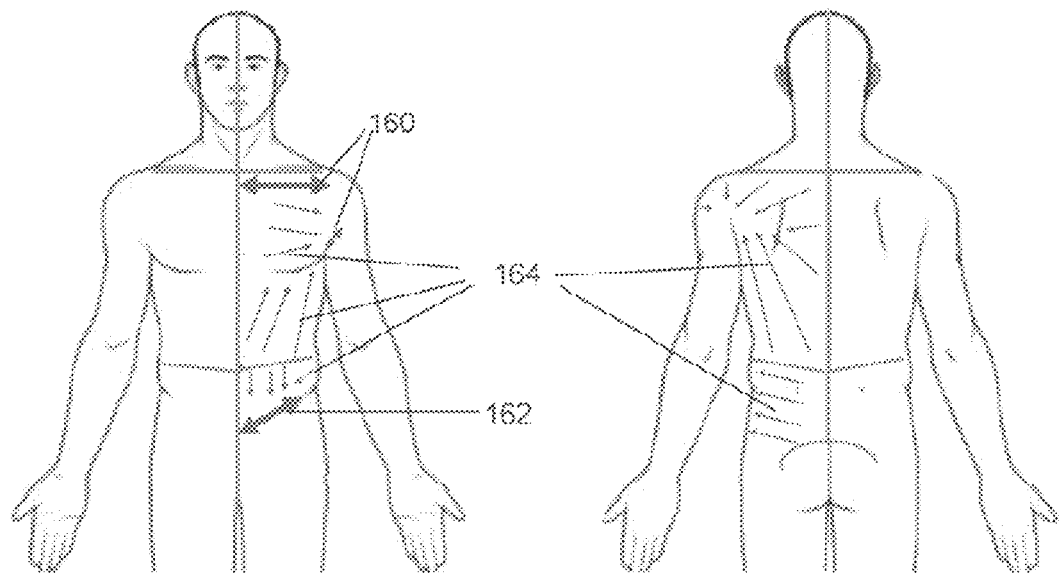
FIG. 5 shows schematic diagrams of the human body illustrating areas for compressive shear thinning, stimulation, and directional movement of static fluid specifically with respect to the chest and abdomen via airstream application, in accordance with embodiments.

FIG. 5 illustrates fluid movement paths in the torso area. Act 82 of the method 80 can be accomplished to treat a fluid stasis area in the torso area via regional application of the airstream 70 to drainage areas 160, 162 (designated by the thick arrows in FIG. 5) to stimulate and condition the drainage areas 160, 162 for uptake of static fluid moved from an area of fluid stasis in the torso area. The airstream 70 can be applied to compress and shear thin the inguinal lymph node area (i.e., the drainage area 162). Additionally, the area of fluid stasis in the torso area being treated can also be compressed and agitated via regional application of the airstream 70 in act 82 of the method 80. In act 84 of the method 80, directional application of the airstream 70 to the patient is used to move static fluid through the torso area fluid movement paths (designated in FIG. 5 via arrows 164). Some of the nozzles described herein (i.e., such as the flat oval nozzle 50-3 illustrated in FIG. 14 and FIG. 15, the curved blade nozzle 50-4 illustrated in FIG. 16 and FIG. 17, the extended curved blade nozzle 50-5 illustrated in FIG. 18 and FIG. 19, the upturned nozzle 50-6 illustrated in FIG. 21, the bump nozzle 50-7 illustrated in FIG. 23 and FIG. 24, the roller nozzle 50-8 illustrated in FIG. 25 through FIG. 27, the hooded nozzle 50-9 illustrated in FIG. 28 and FIG. 29) are configured so that the resulting airstream 70 is formed as a thinner blade of high velocity air configured to be imparted onto the skin 74 of the patient to cause the induced subsurface pressure changes 76 to be concentrated within an elongated region that extends transverse to the direction of desired movement of static fluid so that sweeping of the area of deployment of the airstream 70 in the direction of the desire movement of static fluid may enhance movement of static fluid in the desired direction. Act 84 of the method 80 to accomplish the directional movement of static fluid in the torso area can be accomplished on the front of the body and/or on the back of the body. Any of the nozzles described herein can be used in any sequence to accomplish one or more directional applications of the airstream 70 to move static fluid over fluid movement pathways in the torso area.

Figure 6:
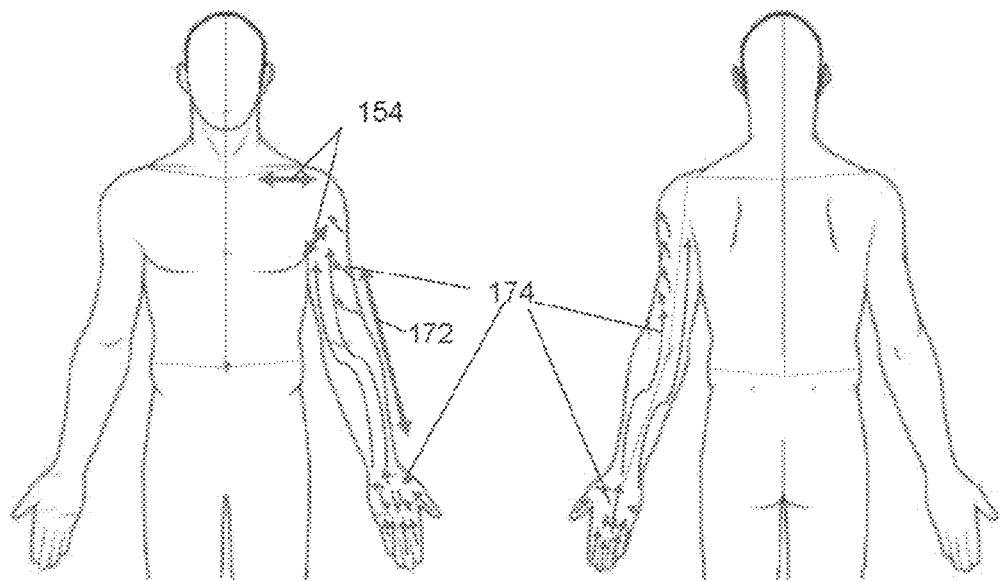
FIG. 6 shows schematic diagrams of the human body illustrating areas for compressive shear thinning, stimulation, and directional movement of static fluid specifically with respect to the upper extremities via airstream application, in accordance with embodiments.

FIG. 6 shows schematic diagrams of the human body illustrating areas for compressive shear thinning, stimulation, and directional movement of static fluid within the left arm. In applying method 80 to the left arm, the regional application of the airstream 70 in act 82 of the method 80 can be applied to the drainage area 170 and the entirety of the left arm (as designated in FIG. 6 by arrow 172). In act 84 of method 80, directional application of the airstream 70 to the patient is used to move static fluid proximally along the left arm through lymphatic pathways (designated in FIG. 6 via arrows 174). As described herein, some of the nozzles described herein are configured so that the resulting airstream 70 is formed as a thinner blade of high velocity air configured to be imparted onto the skin 74 of the patient to cause the induced subsurface pressure changes 76 to be concentrated within an elongated region that extends transverse to the direction of desired movement of static fluid so that sweeping of the area of deployment of the airstream 70 in the direction of the desire movement of static fluid may enhance movement of static fluid in the desired direction. Any of the nozzles described herein can be used in any sequence to accomplish one or more directional applications of the airstream 70 to move static fluid over fluid movement pathways in the left arm. The proximal movement of static fluid in the left arm can be accomplished using sweeping strokes in the distal to proximal direction (indicated by arrows 174) starting the sweeping near the proximal part of the left arm and working distally. By thinning and activating static fluid in the proximal arm first, the fluid movement pathways 174 can be effectively conditioned for the arrival of static fluid from more distal portions of the left arm during movement of static fluid to the drainage area 170. The treatment method described above applies to both the left and right arm.

Figure 7:
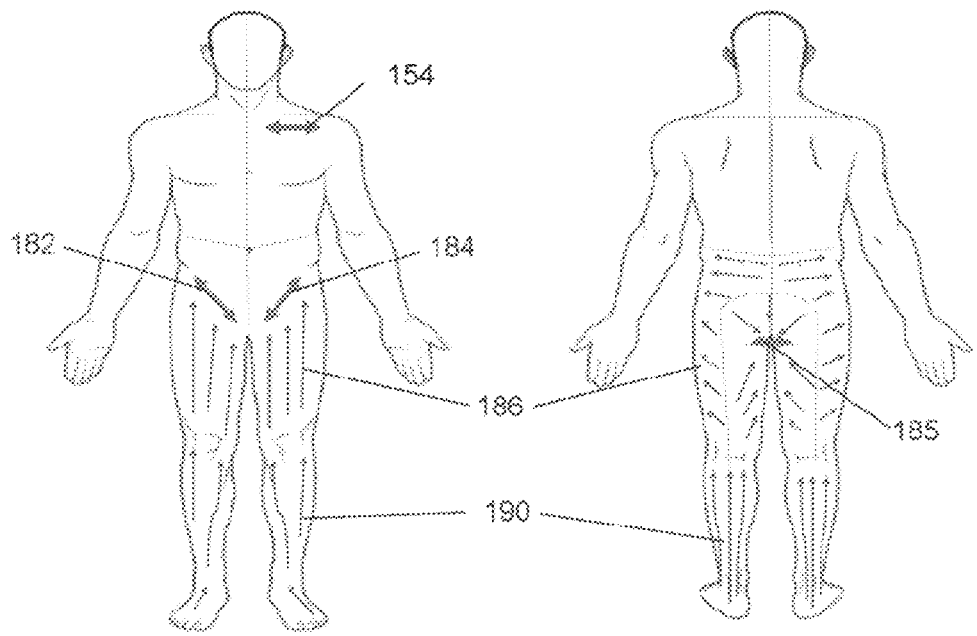
FIG. 7 shows schematic diagrams of the human body illustrating areas for compressive shear thinning, stimulation, and directional movement of static fluid specifically with respect to the lower extremities via airstream application, in accordance with embodiments.

FIG. 7 shows schematic diagrams of the human body illustrating areas for compressive shear thinning, stimulation, and directional movement of static fluid specifically with respect to the lower extremities (i.e., legs) via airstream application, in accordance with embodiments. In act 82 of method 80 as applied to the legs, the regional application of the airstream 70 can be applied to the major drainage areas 152, 154 (especially the left side major drainage area 154 since it provides drainage for the lower part of the body) as described previously. Preferably, the regional application of the airstream 70 is also applied to stimulate and condition the inguinal and pelvic lymph node area 182 and 184 since they too provide drainage for the lower part of the body. The stimulation of the areas 152, 154, 182, and 184 in the accomplishment of act 82 as applied to the legs shear thins static fluid trapped in the main lymphatic ducts to accommodate transfer of a large amount of static fluid from the legs into the torso via the pelvic area. The regional application of the airstream 70 accomplished in act 82 applied to the legs can include regional application of the airstream 70 to shear thin fluid in the dorsal and ventral inguinal lymph nodes in the pelvis. Airstream 70 can be directed perpendicularly to the groin and swept at a diagonal following the crease of the groin as depicted by the arrows 182 and 184 as well as to the perineal area 185. Static fluid from each of one or more of the legs can be agitated in a random pattern on the leg via deployment of the airstream 70, which can be generated using any suitable configuration and/or size of nozzle based on patient size. Act 82 of method 80 is performed to enhance movement of static fluid during subsequent accomplishment of act 84 of method 80 to directly move static fluid out of an area of fluid stasis within each of one or more of the legs. While any of the nozzles described herein can be employed to generate and directionally apply the airstream 70 to the legs, it may be preferable to employ one of the curved blade nozzle 50-4, the extended curved blade nozzle 50-5, the upturned nozzle 50-6, the bump nozzle 50-7, the roller nozzle 50-8, or the hooded nozzle 50-9 to move static fluid in the leg proximally towards the groin. The nozzle is preferably held at an angle such that the airstream 70 emanating from the nozzle is incident upon the skin 74 at suitable angle (e.g., between 0 deg and 60 deg) so as to efficiently induce movement of static fluid. The angle of incidence of the airstream 70 upon the skin 74 can be selected to produce wave-like motions of the skin 74 that may enhance shear thinning and directional movement of static fluid. A nozzle attachment or spacer can be employed to help maintain a suitable positioning and orientation of the nozzle relative to the skin 74. To enhance movement of static fluid out of the leg, fluid within the upper leg can be moved out of the upper leg first via sweeping of the nozzle in the distal to proximal direction (indicated by arrows 186) followed by movement of static fluid out of the lower leg via sweeping of the nozzle in directions 190, 186.

Figure 8:
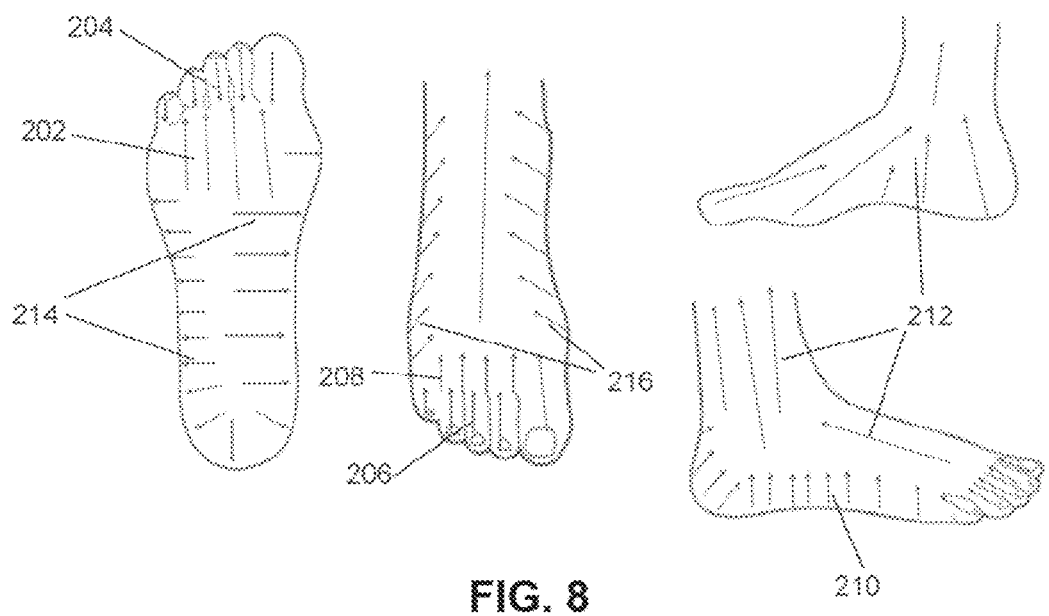
FIG. 8 shows schematic diagrams of the human foot illustrating areas for compressive shear thinning, stimulation, and directional movement of static fluid via airstream application, in accordance with embodiments.
Figure 9:
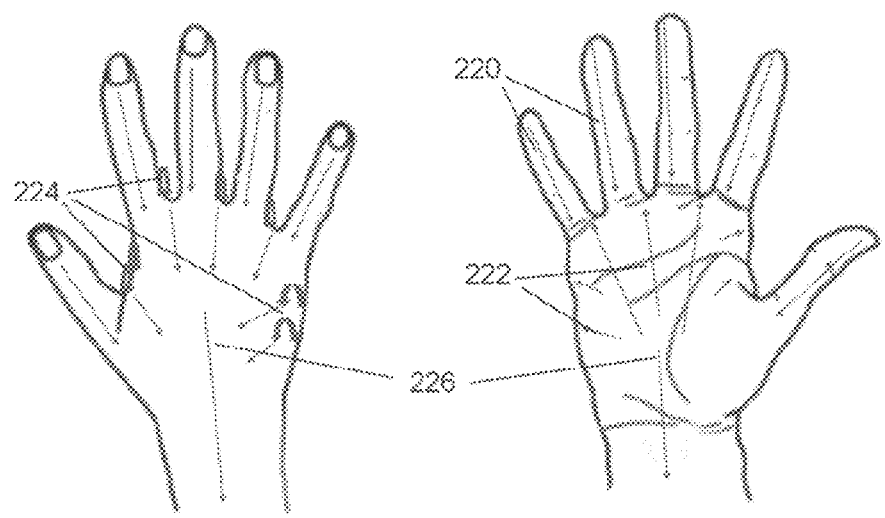
FIG. 9 shows schematic diagrams of the human hand illustrating areas for compressive shear thinning, stimulation, and directional movement of static fluid via airstream application, in accordance with embodiments.

FIG. 8 shows schematic diagrams of the human foot illustrating areas for compressive shear thinning, stimulation, and directional movement of static fluid via airstream application, in accordance with embodiments. FIG. 9 shows schematic diagrams of the human hand illustrating areas for compressive shear thinning, stimulation, and directional movement of static fluid via airstream application, in accordance with embodiments. Due to the complex lymphatic structures in the feet and hands, a simple distal to proximal movement of static fluid is not the most optimal approach for treating fluid stasis (e.g., edema) in the feet and hands. Instead, to enhance efficacy of treatment of fluid stasis in a hand or a foot, method 80 can be separately applied to a hand or a foot to move static fluid out of the hand or the foot via the more complex fluid movement pathways of the hand or the foot.

Management of fluid stasis (e.g., edema) in the feet/toes is ideally performed after the method 80 is accomplished on the legs, inguinal nodes, and torso, thereby ensuring that the lymphatic and vascular pathways in the legs are cleared and stimulated to support more effective movement of static fluid from the feet to the drainage points. An appropriately sized flattened or curved nozzle may be used to push fluid from the sole of the foot toward the base of the toes as indicated by the arrows 202 and the tips of the toes proximally to the base of the toes as indicated by the arrows 204 and 206. Following the lymphatic pathways, static fluid may be pushed between the toes to the top of the foot and continued to be directed proximally as indicated by the arrows 208. In embodiments, this movement of fluid may utilize a small, curved, or oval nozzle specifically designed for the toes. Generally, static fluid can be moved from the sole of the foot to the top of the foot as shown by the arrows 210, then pushed proximally as shown by the arrows 212. The area around the heel and midsole may be worked laterally using the appropriately sized nozzle as indicated by the arrows 214, and ultimately pushing static fluid and stimulating the pathways on the top of the foot as indicated by the arrows 216. Following this procedure, the method 80 may be applied to the legs once again to move static fluid through the legs to the torso for drainage. The application of method 80 to a foot may be effective for preventing nerve damage and subsequent neuropathy from chemical agents (e.g. chemotherapy) and pharmaceuticals.

As can be appreciated in view of FIG. 9, the application of the method 80 to a hand is similar to the application of the method 80 to a foot. As with a foot, management of fluid stasis in a hand is ideally performed after the method 80 has been applied to the corresponding arm and 152 or 154 to stimulate the arm and flush fluid from the arm to better accommodate transfer static fluid out of the hand. An appropriately sized embodiment of the flat oval nozzle 50-3 can be used to produce and direct the airstream 70 onto the hand to move fluid distally from the wrist to the creases between the flingers. Starting on the palm side, the airstream 70 can be directed onto the hand to move the fluid using small sweeping motions from the fingertips toward the base of the fingers as indicated by the arrows 220 and from the center of the palm as indicated by arrows 222. Each finger can be individually drained of excess fluid, starting from the distal end of the finger to where the finger meets the hand. After this, the areas between the fingers can be stimulated from the palm to the top of the hand distally, following the lymphatic pathways indicated by the curved arrows 224. The flat oval nozzle 50-3 can then be used to move the fluid proximally as indicated by the arrows 226 towards the top of the wrist and into the arm. After moving the fluid into the arm, method 80 can be reapplied to the arm to move static fluid proximally through the arm to a corresponding one of the drainage areas 152, 154. The application of method 80 to a hand may be effective for preventing nerve damage and subsequent neuropathy from chemical agents (e.g., chemotherapy) and pharmaceuticals.

Figure 10:
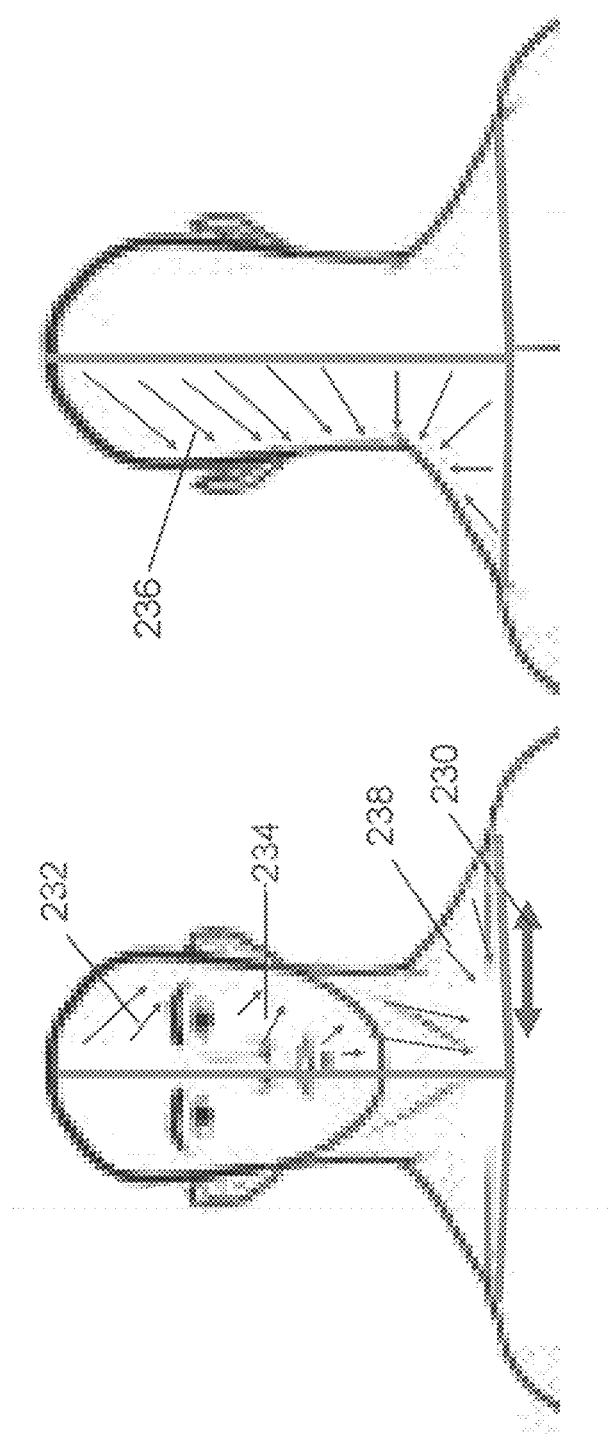
FIG. 10 shows schematic diagrams of the human head and neck region illustrating areas for compressive shear thinning, stimulation, and directional movement of static fluid via airstream application, in accordance with embodiments.

FIG. 10 shows schematic diagrams of the human head and neck region illustrating areas for compressive shear thinning, stimulation, and directional movement of static fluid via airstream application, in accordance with embodiments. The application of method 80 to the head and neck region can start with the regional application of the airstream 70 to the drainage area 230 in accordance with act 82 of method 80. Following the regional application of the airstream 70 to the drainage area 230, the airstream 70 can be used to 84 directionally sweep static fluid from the top of the head, towards the outer portion of the face as indicated by the arrows 232, and from the center of the face towards the rear as indicated by the arrows 234. This fluid movement approach can be repeated for the back of the head using sweeping motions aimed towards the crease between the neck and shoulder as indicated by the arrows 234, following the lymphatic pathways. The sweeping motion can be continued towards the proximal end of the clavicle as indicated by the arrows 238, so that the fluid is moved towards the subclavian vein.

Nozzles for Treating Fluid Stasis

Each of the nozzles described herein, when supplied an airflow having a suitable volumetric flow rate, is configured to output an airstream 70 that is suitably configured for deployment upon the skin 74 of the patient so that the induced subsurface pressure variations 76? are configured for producing shear thinning of static fluid and/or stimulation and conditioning of fluid movement pathways and drainage areas as described herein. Each of the nozzles described herein can be used to practice the method 80 and selectively used based on the location of the area of fluid stasis being treated and/or whether the airstream 70 is regionally applied (as accomplished in act 82 of the method 80) or directionally applied (as accomplished in act 84 of the method 80).

Figure 45:
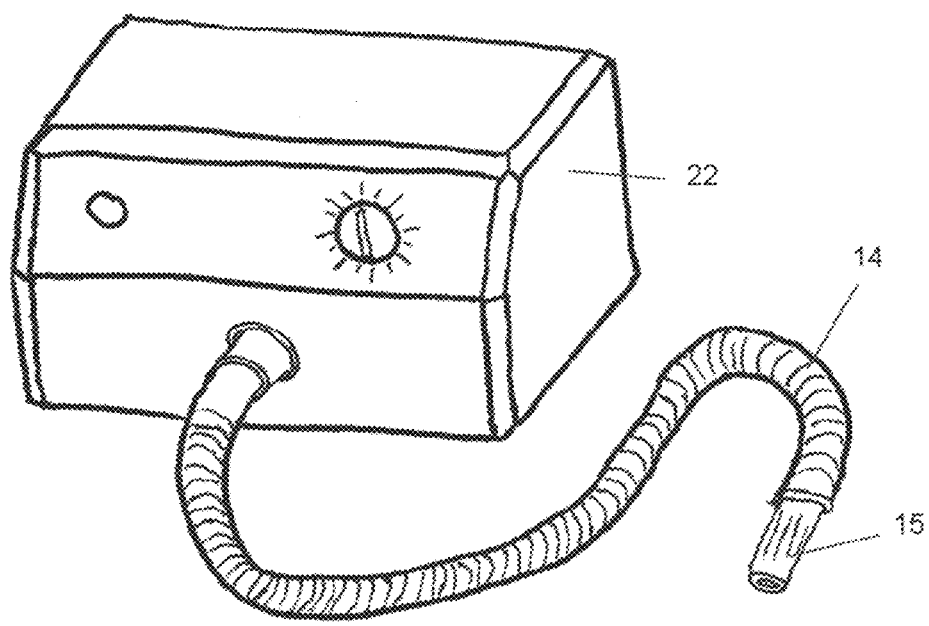
FIG. 45 illustrates an example airstream generator and airstream hose configured to generate and deliver an airstream for inducing shear thinning of static fluid, inducing movement of static fluid, and/or simulating/conditioning one or more lymphatic nodes, one or more lymphatic ducts, and/or blood vessels for transport and/or uptake of static fluid, in accordance with embodiments.

In many embodiments, each of the nozzles disclosed herein is detachably mountable to the airflow supply hose 14 used to supply airflow to the nozzle generated by the main unit 12 (shown in FIG. 45). The nozzles described herein provide a way to produce and direct the airstream 70 onto the surface of a patient to exerts pressure on the patient to induce the subsurface pressure changes 76, which are used to induce shear thinning of static fluid and/or stimulate/ condition fluid movement pathways in the patient. Each of the nozzles has an outlet orifice having a specific cross-section and contour for configuring the airstream 70 (e.g., cross-sectional shape of the airstream, average flow rate of the airstream at the outlet orifice) to be suitable for application to a portion of the patient being treated, such as arms, fingers, legs, abdomen, head, or neck areas. Variations of each of the nozzles described herein can be configured to tailor the airstream 70 (e.g., specific shapes, specific average flow rate at the outlet orifice) for use in treating fluid stasis (e.g., edema) within any one or more regions of a patient. By employing a nozzle specifically configured for a corresponding region of the patient being treated, the deployment of the airstream 70 onto the patient may more efficiently displace and move static fluid into the lymphatic system.

In embodiments, the nozzles may be configured with a manual compressive element configured to be manually pressed onto the patient to directly apply associated compressive pressure to the patient. The manual compressive element can have any suitable configuration. For example, the manual compressive element may be attached via a securing mechanism or manufactured to be integral with the nozzle. The manual compressive element may include a set of rigid or semi-rigid rollers configured to be interfaced with the skin 74 of the patient to manually impart compressive forces to induce shear thinning and/or movement of static fluid within the tissue of the patient to one or more drainage areas for fluid. Alternatively, the manual compressive element can include one or more soft rollers (such as rubber or foam), which may be more comfortable for the patient. In embodiments, the manual compressive element is manually pressed against the patient in combination with the application of the airstream 70 to the patient during the accomplishment of the method 80. In embodiments, the nozzle is configured to generate an area of negative air pressure beneath and immediately behind the nozzle via the venturi effect resulting from flow of air between the nozzle and the skin 74 induced by the output of the airstream 70 from the nozzle. The area of negative pressure pulls a region of the skin 74 subjected to the negative pressure towards the nozzle. The pulling of the region of skin 74 toward the nozzle, in combination with the compressive forces applied to the patient via deployment of the airstream on the patient forward of the nozzle, may have the effect of both inducing shear thinning of static fluid, opening the lymphatic vessels to induce and/or accommodate movement of static fluid, and quickly re-perfusing the immediate area behind the nozzle.

In embodiments, the nozzle is configured to output a first airstream and a second airstream (configured primarily to induce shear thinning of static fluid and/or stimulation/conditioning of a fluid movement pathway) and a second airstream (configured primarily for inducing movement of static fluid). The first airstream can be shaped and oriented, preferably to be incident on the skin no more than 20 degrees from being perpendicular to the skin, to primarily to induce shear thinning of static fluid and/or stimulation/conditioning of a fluid movement pathway. The second airstream can be shaped to have a thin blade configuration and oriented, preferably at an acute angle less than 60 degrees relative to the skin, to induce movement of static fluid. The nozzle can be configured as a split nozzle configured to produce the first airstream and the second airstream from a single airflow provided to the split nozzle by a single hose. Alternatively, the nozzle can be configured to be attached to a first airflow supply hose that supplies a first airflow used to generate the first airstream and a second airflow supply hose that supplies a second airflow used to generate the second airstream.

In embodiments, a nozzle for use in accomplishing the method 80 is customizable to accommodate customization of the airstream 70 via customization of the shape and/or size of the outlet orifice of the nozzle to conform the airstream 70 to the patient anatomy and thus provide more efficient treatment. In some embodiments, the outlet orifice is defined by an outlet portion of the nozzle made from a malleable metal or thermoplastic resin that accommodates reconfiguration of the outlet portion of the nozzle (via deformation of the malleable metal or application of heat to the thermoplastic resin) to effect reshaping and/or resizing of the outlet orifice to customize the airstream 70.

In many embodiments, each of the nozzles described herein is configured for detachable mounting to the airflow supply hose 14. A quick-change nozzle may also be employed that includes a single airflow inlet and a set of different nozzle outlets that can be selectively coupled with the airflow inlet to select that configuration of the airstream 70 output by the quick-change nozzle to provide expediency when moving between body parts or forced air functionality (shear-thinning only vs directional fluid movement).

Figure 11:
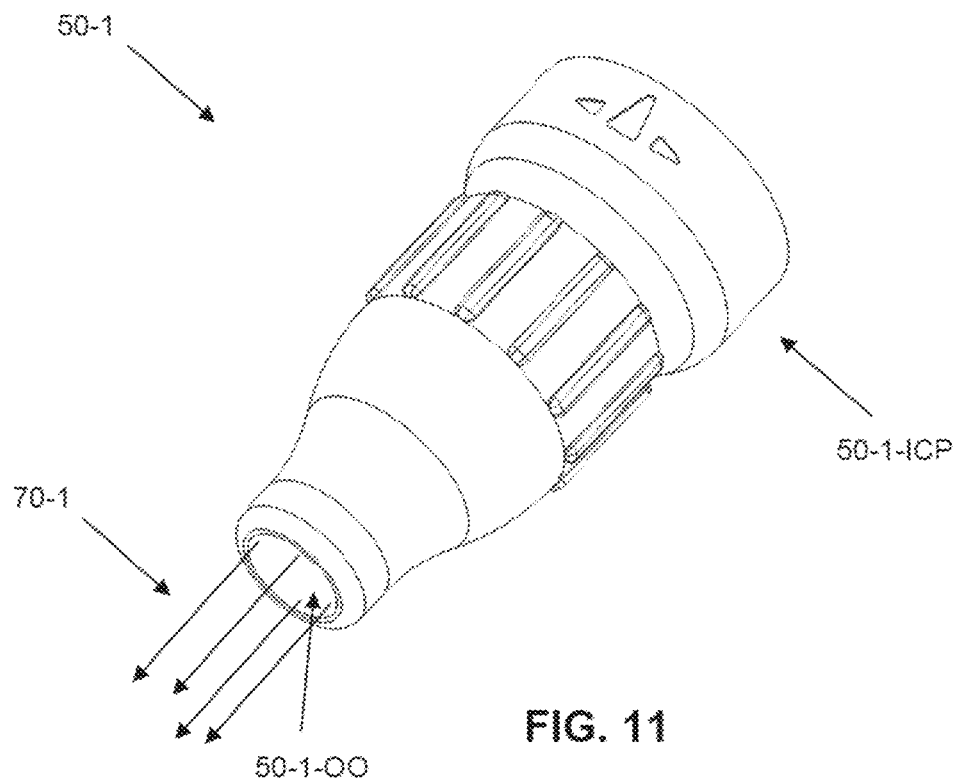
FIG. 11 and FIG. 12 show views of a round nozzle configured to output a round airstream for application to a patient to induce compressive shear thinning, stimulation, and directional movement of static fluid, in accordance with embodiments.
Figure 12:
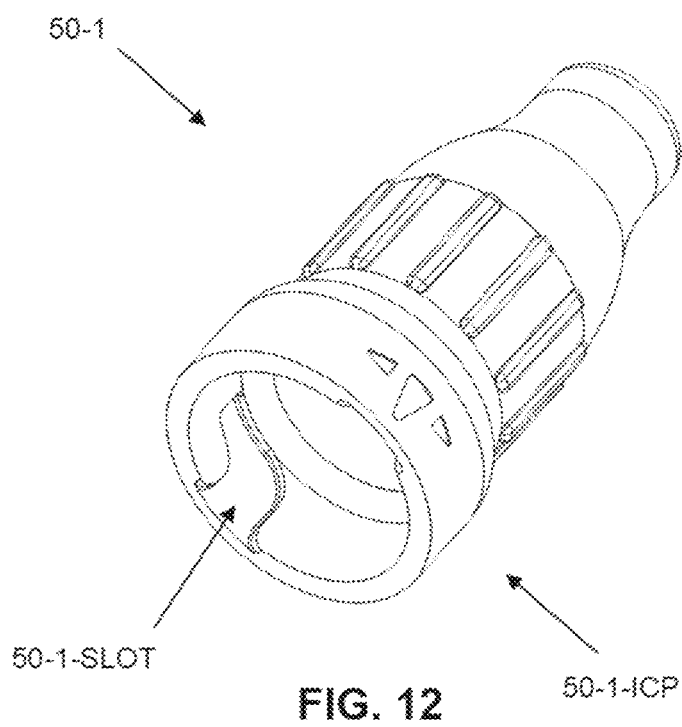

FIG. 11 and FIG. 12 show views of a round nozzle 50-1 configured to output a round airstream 70-1 for application to a patient to induce compressive shear thinning, stimulation, and directional movement of static fluid, in accordance with embodiments. The round nozzle 50-1 includes a round outlet orifice (50-1-OO) and an inlet coupling portion (50-1-ICP). The inlet coupling portion (50-1-ICP) and the airflow supply hose 14 can have any suitable coupling features configured to accommodate detachable coupling of the round nozzle 50-1 to the airflow supply hose 14. For example, in the illustrated embodiment, the inlet coupling portion (50-1-ICP) includes bayonet style coupling slots (50-1-SLOTS) shaped to accommodate and engage complementarily shaped bayonet features of the airflow supply hose 14. The round outlet orifice (50-1-OO) can have any suitable cross-sectional area greater than 113 mm$^2$.

As described herein, act 82 of the method 80 employs a regional application of an airstream 70 to induce shear-thinning of static fluid and stimulating/conditioning of one or more lymph nodes and/or vasculature. The round nozzle 50-1 is configured for use in accomplishing the regional application of the airstream 70. With the round nozzle 50-1 affixed to the airflow supply hose 14, the round airstream 70-1 (which has a round cross-sectional shape as output from the round outlet orifice (50-1-OO)) can be applied at an angle substantially perpendicular to the skin 74. The round airstream 70-1 can have a suitable average flow rate to nozzle area ratio at the round outlet orifice (50-1-OO) of (in units of (m$^3$/min) to mm$^2$) 0.004 to 0.020, more preferably in a range from 0.009 to 0.014. Application of the round airstream 70-1 to the skin 74 substantially perpendicular to the skin 74 can be used to induce subsurface compression changes 22 applied to one or more lymph nodes, one or more lymphatic system ducts, and/or one or more blood vessels as well as to static fluid residing in the subcutaneous soft tissues. As discussed herein, the induced subsurface compression changes 22 reduce the viscosity of static fluid to aid in the movement of static fluid out of an area of fluid stasis and through a fluid movement pathway to a drainage area. In addition to the shear-thinning effect on static fluid, the subsurface pressure changes 76 stimulate lymphatic nodes and ducts enhance movement of static fluid through the lymphatic nodes and ducts.

In the illustrated embodiment, the round nozzle 50-1 has a straight converging bore between the inlet coupling portion (50-1-ICP) and the round outlet orifice (50-1-OO). Alternatively, the round nozzle can have a diverging bore from the inlet coupling portion (50-1-ICP) and the round outlet orifice (50-1-OO), as in the form a reverse funnel. Because the round nozzle 50-1 can be configured in a wide range of sizes, the round nozzle 50-1 can be configured for use in treating any particular area of a patient in either of act 82 or act 84 of method 80. The round nozzle 50-1 can be especially suited for use in accomplishing the regional application of the airstream 70 in act 82 of the method 80.

In some embodiments, the round nozzle 50-1 includes an adjustable aperture or iris that is adjustable to accommodate changing of the nozzle outlet diameter on the fly without having to manually change the round nozzle 50-1 for a different nozzle. Equipping the round nozzle 50-1 can be used to reduce the number of nozzles employed to practice the method 80 on a patient and may decrease total treatment time due to reduction in the time consumed changing nozzles.

Figure 13:
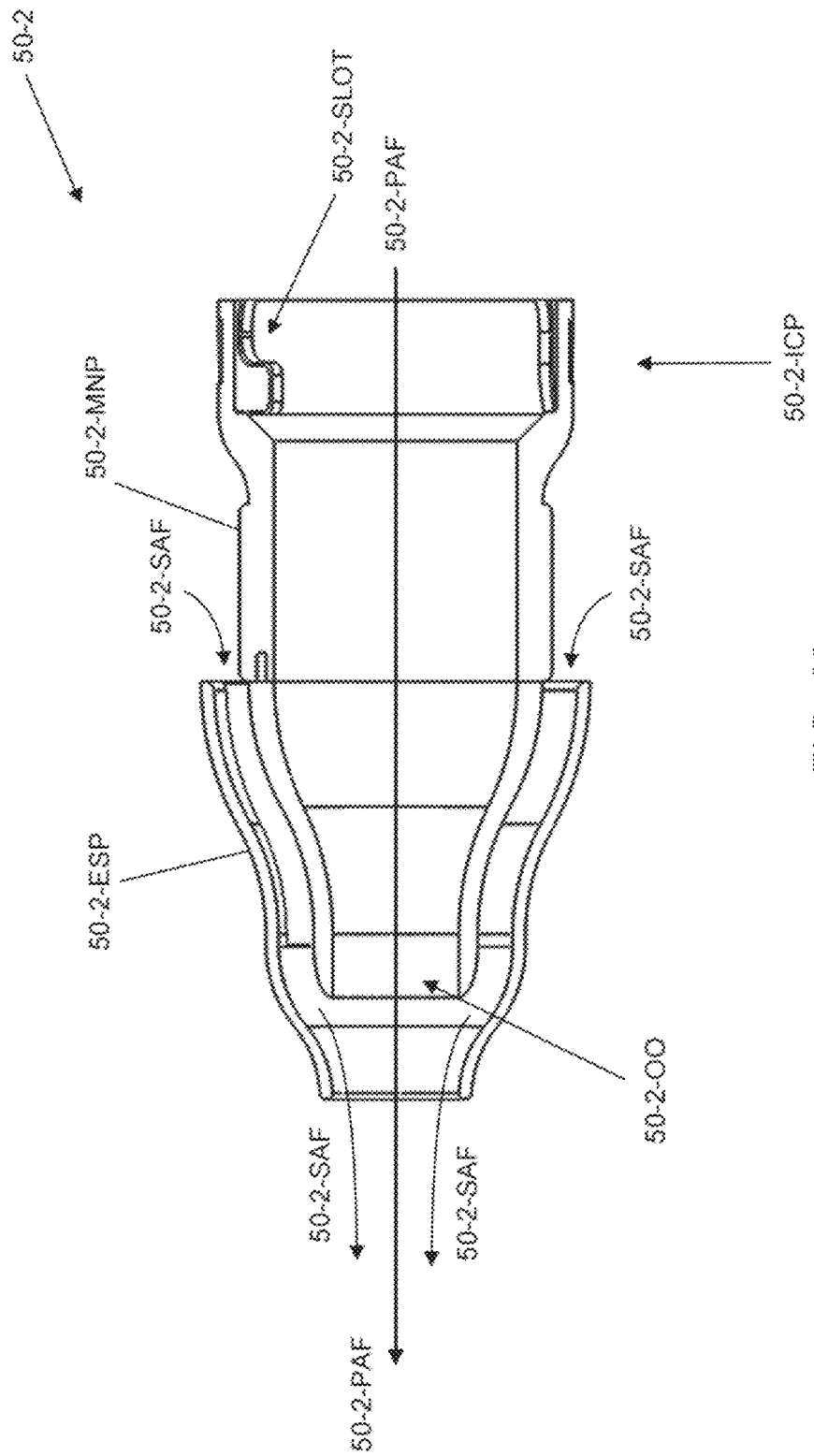
FIG. 13 shows a cross-sectional view of an entrainment nozzle configured to output an airstream that includes an entrained airflow for application to a patient to induce compressive shear thinning, stimulation, and directional movement of static fluid, in accordance with embodiments.

FIG. 13 shows a cross-sectional view of an entrainment nozzle 50-2 configured to output an airstream that includes an entrained airflow for application to a patient to induce compressive shear thinning, stimulation, and directional movement of static fluid, in accordance with embodiments. The entrainment nozzle includes a main nozzle portion (50-2-MNP) and an entrainment shell portion (50-2-ESP). The main nozzle portion (50-2-MNP) includes a round main nozzle portion outlet orifice (50-2-OO) and an inlet coupling portion (50-2-ICP). The inlet coupling portion (50-2-ICP) and the airflow supply hose 14 can have any suitable coupling features configured to accommodate detachable coupling of the entrainment nozzle 50-2 to the airflow supply hose 14. For example, in the illustrated embodiment, the inlet coupling portion (50-2-ICP) includes bayonet style coupling slots (50-2-SLOT) shaped to accommodate and engage complementarily shaped bayonet features of the airflow supply hose 14. The round main nozzle portion outlet orifice (50-2-OO) can have any suitable cross-sectional area (e.g., in a range from 300 to 700 mm$^2$). The entrainment shell portion (50-2-ESP) surrounds a distal end portion of the main nozzle portion (50-2-MNP). The entrainment shell portion (50-2-ESP) and the main nozzle portion (50-2-MNP) combined to define an annular entrainment airstream inlet via which a secondary airflow (50-2-SAF) is entrained with a primary airflow (50-2-PAF) received from the airflow supply hose 14. The entrainment nozzle 50-2 can be employed in practicing the method 80 the same as or similar to the round nozzle 50-1. The primary airstream 50-2-PAF can have a suitable average flow rate to nozzle area ratio at the round outlet orifice (50-2-OO) of (in units of (m$^3$/min) to mm$^2$) 0.004 to 0.020, more preferably in a range from 0.009 to 0.014.

Figure 14:
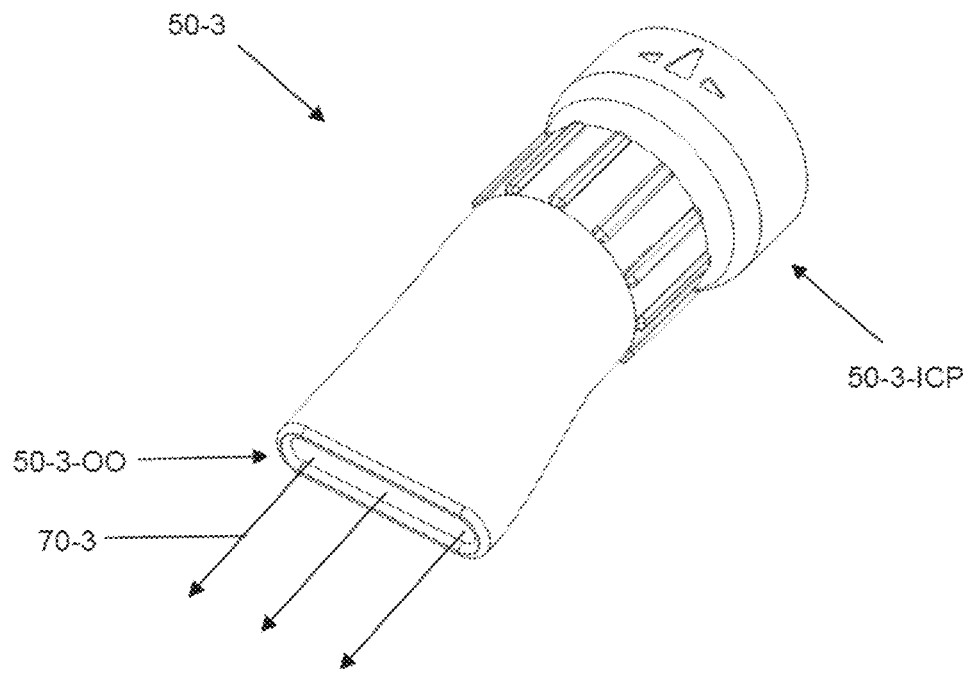
FIG. 14 and FIG. 15 show views of a flat oval nozzle configured to output a flat oval airstream for application to a patient to induce compressive shear thinning, stimulation, and directional movement of static fluid, in accordance with embodiments.
Figure 15:
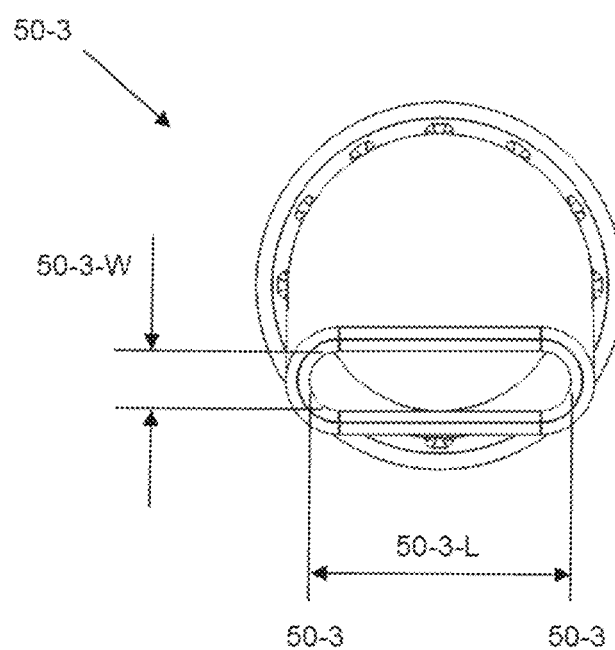

FIG. 14 and FIG. 15 show views of a flat oval nozzle 50-3 configured to output a flat oval airstream 70-3 for application to a patient to induce compressive shear thinning, stimulation, and directional movement of static fluid, in accordance with embodiments. The flat oval nozzle 50-3 has an elongated flat oval outlet orifice (50-3-OO) configured so that the flat oval airstream 70-3 has a relatively thin flat oval cross-sectional shape, which can be especially suited for use in act 84 of the method 80 to induce directional movement of static fluid. The flat oval nozzle 50-3 can also be used in act 82 of method 80 for the regional application of the airstream 70. The flat oval airstream 70-3 can have a suitable average flow rate to nozzle area ratio at the round outlet orifice (50-3-OO) of (in units of (m$^3$/min) to mm$^2$) 0.004 to 0.020, more preferably in a range from 0.009 to 0.014. The flat oval outlet orifice (50-3-OO) can have any suitable cross-sectional area (e.g., in a range from 300 to 700 mm$^2$). The elongated flat oval outlet orifice (50-3-OO) can have any suitable length (50-3-L) to width (50-3-W) ratio (e.g., in a range from 2:1 to 10:1). In the illustrated embodiment, the elongated flat oval outlet orifice (50-3-OO) has a length to width ratio of 5.4:1. The flat oval nozzle 50-3 may be especially useful for moving static fluid within a flat anatomical region. The flat oval nozzle 50-3 can be configured with relatively small size for use in moving static fluid around smaller anatomical features (e.g., finger, toes) and in areas with limited room to accommodate the nozzle 50. The flat oval opening may also be offset from the centerline or the inlet opening to aid in guiding the nozzle tip around the anatomy and achieving a generally more parallel angle of airflow 70-3 in relation to the anatomy or a treatment table surface.

Figure 16:
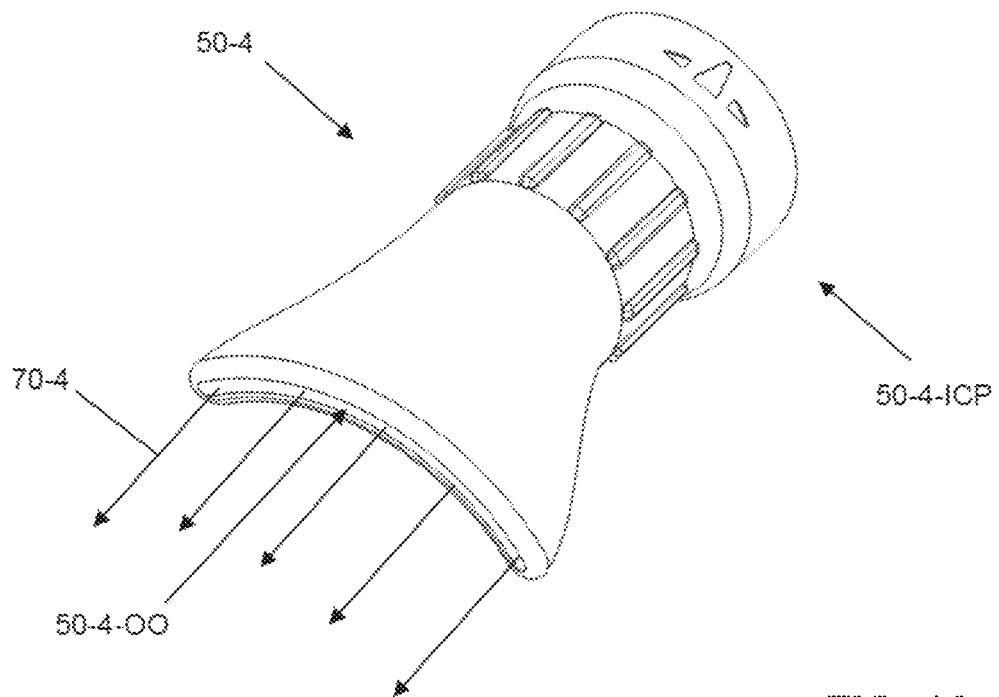
FIG. 16 and FIG. 17 show views of a curved blade nozzle configured to output a curved blade airstream for application to a patient to induce compressive shear thinning, stimulation, and directional movement of static fluid, in accordance with embodiments.
Figure 17:
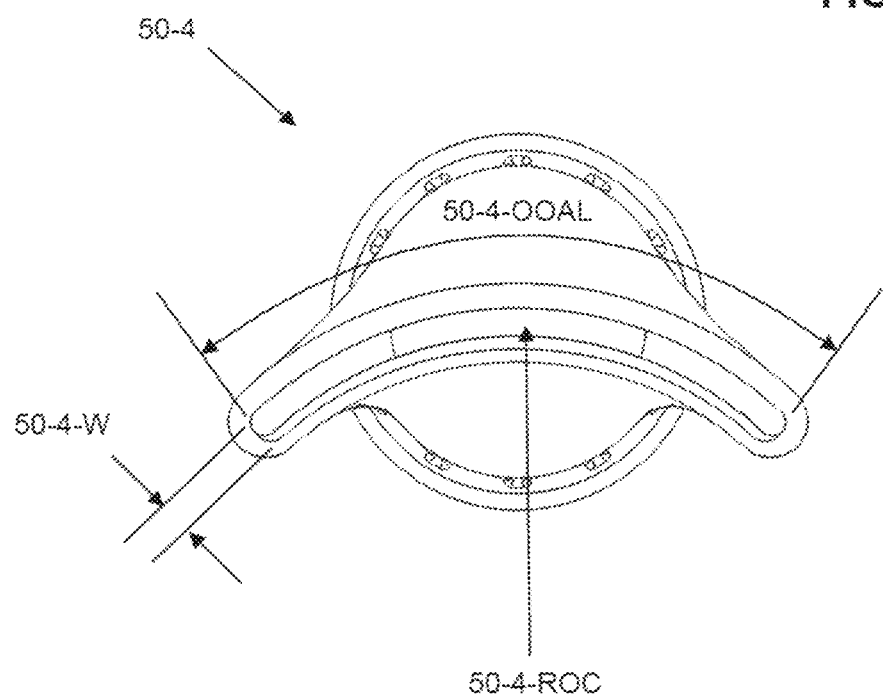

FIG. 16 and FIG. 17 show views of a curved blade nozzle 50-4 configured to output a curved blade airstream 70-4 for application to a patient to induce compressive shear thinning, stimulation, and/or directional movement of static fluid, in accordance with embodiments. The curved blade nozzle 50-4 is configured similar to the flat oval nozzle 50-3 but has a curved blade nozzle outlet orifice (50-4-OO) with a curved profile configured so that the curved blade airstream 70-4 has a corresponding thin curved blade cross-sectional shape corresponding to the shape of the outlet orifice (50-4-OO). The curved blade airstream 70-4 can have a suitable average flow rate to nozzle area ratio at the round outlet orifice (50-4-OO) of (in units of (m$^3$/min) to mm$^2$) 0.004 to 0.020, more preferably in a range from 0.009 to 0.014. The curved blade airstream 70-4 may be particularly effective for use in accomplishing act 84 of the method 80 to induce movement of static fluid within a curved bodily region like the leg or back because the curved blade airstream 70-4 is shaped to better match the shape of the curved bodily region, thereby more uniformly and completely imparting on the curved bodily region, which helps to maximize the coverage of the resulting distribution of the induced subsurface pressure changes 76. Configurational parameters of the curved blade nozzle outlet orifice (50-4-OO) (i.e., outlet orifice arc length (50-4-OOAL), outlet orifice radius of curvature (50-4-ROC), and outlet orifice width (50-4-W) can be tailored to configure the curved blade nozzle 50-4 for use with any particular area of the body. For example, the configuration parameters of the curved blade nozzle 50-4 can be selected to conform to the curved blade airstream 70-4 for application to particular body regions (e.g., to a large slightly curved body regions such as the back, to a small tightly curved body region such as a finger, or to a medium sized curved body region such as an arm or a leg).

Figure 18:
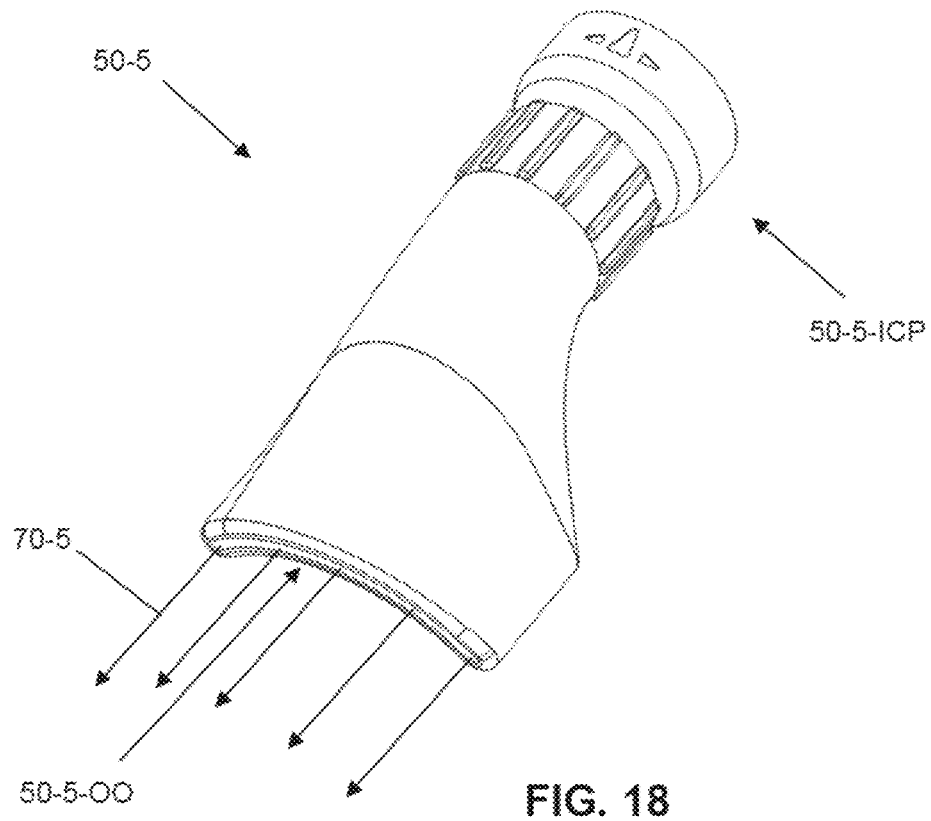
FIG. 18 and FIG. 19 show views of an extended curved blade nozzle configured to output a curved blade airstream for application to a patient and operable to apply suction to a region of the patient to induce compressive shear thinning, stimulation, and directional movement of static fluid, and apply suction to a region, in accordance with embodiments.
Figure 19:
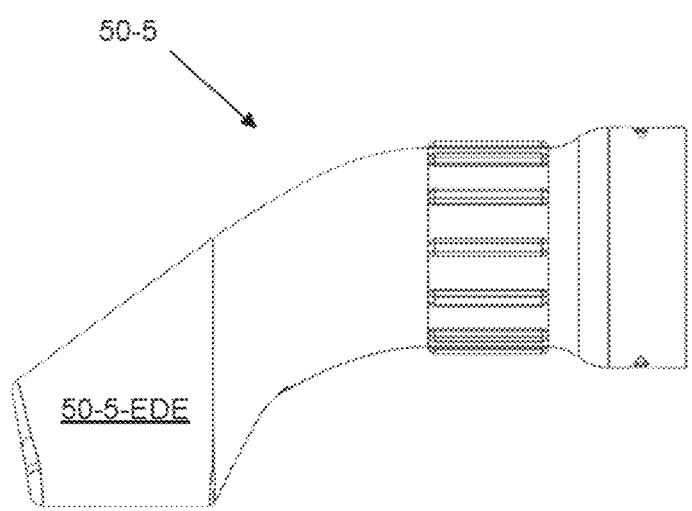

FIG. 18 and FIG. 19 show views of an extended curved blade nozzle 50-5 configured to output an extended curved blade airstream 50-5 for application to a patient and operable to apply suction (50-5-S) (illustrated in FIG. 20) to a region of the patient to induce compressive shear thinning, stimulation, and directional movement of static fluid, in accordance with embodiments. The extended curved blade nozzle 50-5 is configured similar to the curved blade nozzle 50-4 but further includes an extended distal end portion (50-5-EDE). The extended curved blade nozzle 50-5 further includes an extended curved blade nozzle outlet orifice (50-5-OO) with a curved profile configured so that the extended curved blade airstream 70-5 has a corresponding thin curved blade cross-sectional shape corresponding to the shape of the outlet orifice (50-5-OO). The extended curved airstream 70-5 can have a suitable average flow rate to nozzle area ratio at the round outlet orifice (50-5-OO) of (in units of (m$^3$/min) to mm$^2$) 0.004 to 0.020, more preferably in a range from 0.009 to 0.014. The extended curved blade nozzle outlet orifice (50-4-OO) can have any suitable cross-sectional area (e.g., in a range from 300 to 700 mm$^2$). The extended curved blade airstream 70-5 may be particularly effective for use in accomplishing act 84 of the method 80 to induce movement of static fluid within a curved bodily region like the leg or back because the extended curved blade airstream 70-5 is shaped to better match the shape of the curved bodily region, thereby more uniformly and completely imparting on the curved bodily region, which helps to maximize the coverage of the resulting distribution of the induced subsurface pressure changes 76. Configurational parameters of the extended curved blade nozzle outlet orifice (50-5-OO) (i.e., orifice arc length, orifice radius of curvature, and orifice width) can be tailored to configure the extended curved blade nozzle 50-5 for use with any particular area of the body. For example, the configuration parameters of the extended curved blade nozzle 50-5 can be selected to conform to the extended curved blade airstream 70-5 for application to particular body regions (e.g., to a large slightly curved body regions such as the back, to a small tightly curved body region such as a finger, or to a medium sized curved body region such as an arm or a leg).

The extended distal end portion (50-5-EDE), when interfaced with patient, a suction channel (50-5-SC) is formed and extends between the extended distal end portion (50-5-EDE) and the patient's skin 74. The extended curve blade nozzle 50-5 includes an outlet orifice (50-5-OO) from which the curved blade airstream 70-5 is discharged. The curved blade airstream 70-5 draws air through the suction channel (50-5-SC), which lowers the pressure of the air flowing through the suction channel (50-5-SC) due to the venturi effect. The extended distal end portion (50-5-EDE) forms sidewalls of the suction channel (50-5-SC), thereby helping to enhance the magnitude of the pressure drop within the suction channel (50-5-SC).

Figure 20:
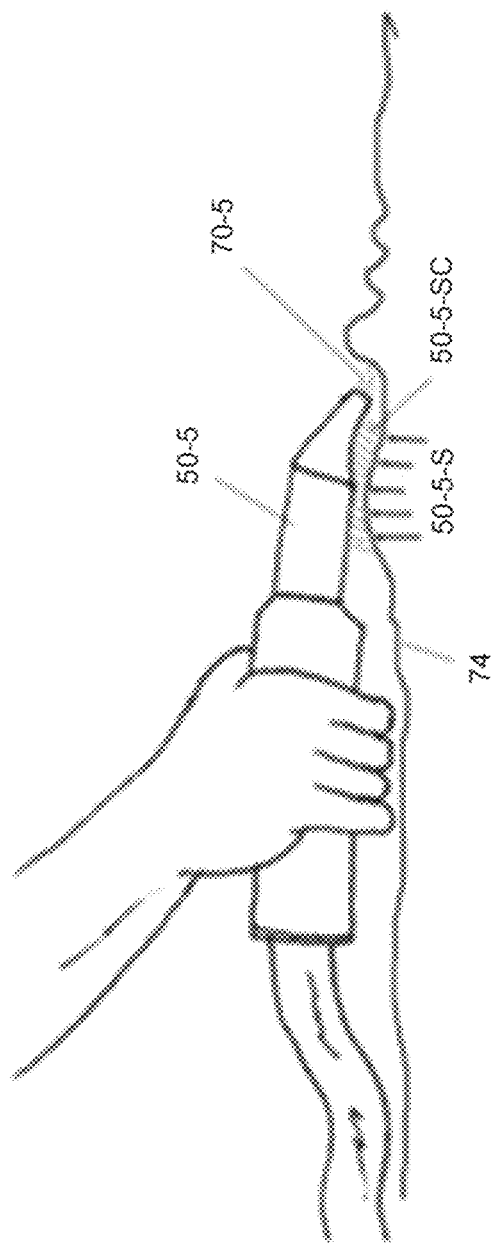
FIG. 20 illustrates operation of the extended curved blade nozzle of FIG. 18 and FIG. 19 to apply the curved blade airstream and suction to a patient to induce compressive shear thinning, stimulation, and directional movement of static fluid, in accordance with embodiments.

FIG. 20 illustrates operation of the extended curved blade nozzle 50-5. In the illustrated configuration, lower end side surfaces of the extended distal end portion (50-5-EDE) are interfaced with the skin 74 of the patient thereby forming the suction channel (50-5-SC) that extends between an under surface of the extended curved blade nozzle 50-5 and the skin 74. Discharge of the curved airstream 70-5 from the outlet orifice (50-5-OO) draws a flow of air through the suction channel (50-5-SC), thereby generating suction within the suction channel (50-5-SC), which pulls the skin 74 toward the anterior of nozzle 50-5 thereby expanding lymphatic ducts within the tissue local to the suction channel (50-5-SC), which may serve to re-perfuse the immediate area as the deployment zone of the curved airstream 70-5 is moved along the skin towards a drainage area during the accomplishment of act 84 of the method 80.

Figure 21:
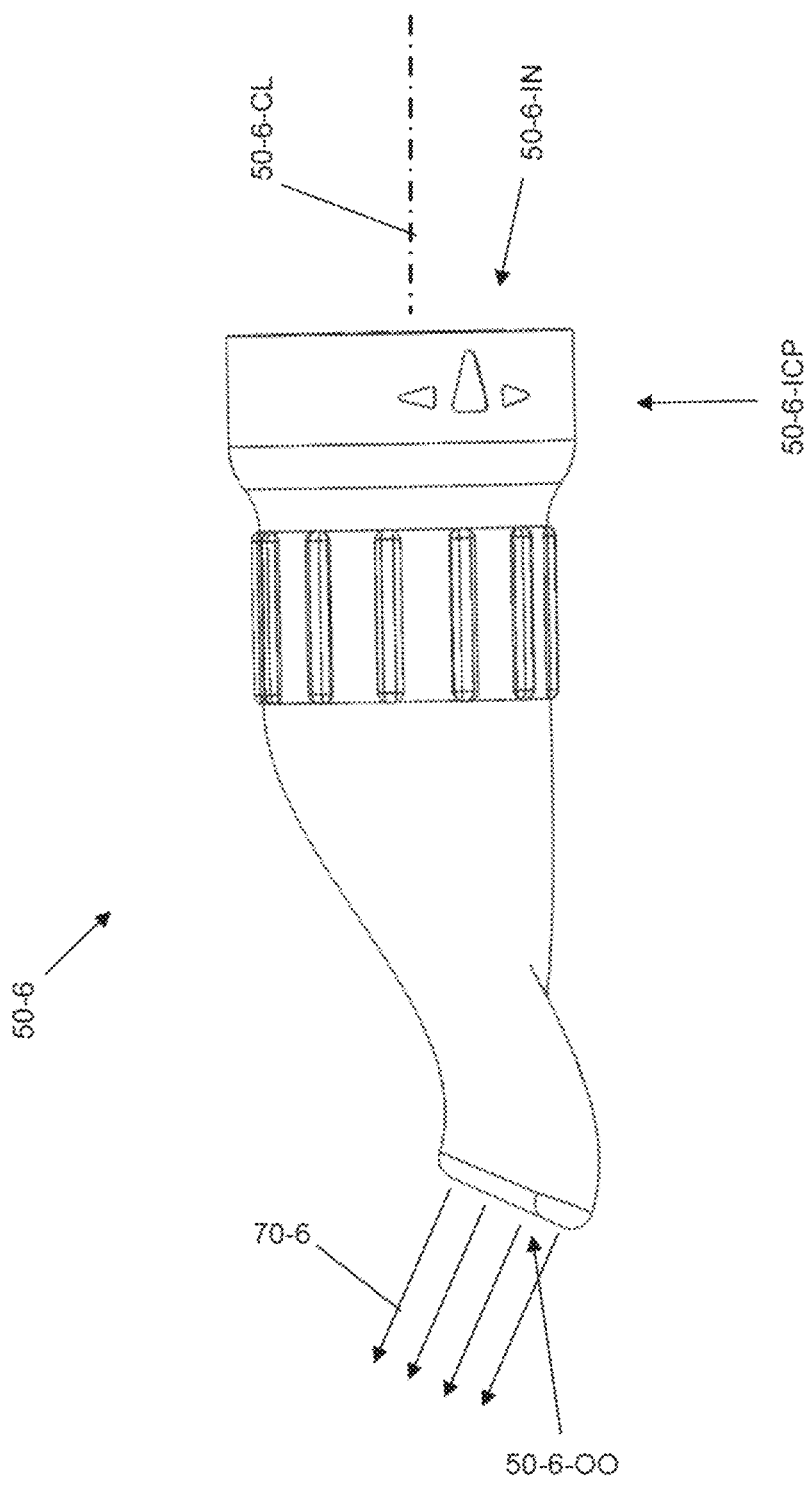
FIG. 21 illustrates an upturned nozzle configured to output an upturned airstream that can be applied to concave shaped regions of a patient to induce compressive shear thinning, stimulation, and directional movement of static fluid, in accordance with embodiments.

FIG. 21 illustrates an upturned nozzle 50-6 configured to output an upturned nozzle airstream 70-6 that can be applied to concave shaped regions of a patient to induce compressive shear thinning, stimulation, and directional movement of static fluid, in accordance with embodiments. The upturned nozzle 50-6 is configured similar to either of the flat oval nozzle 50-3 of the curved blade nozzle 50-4 but has an upturned nozzle outlet orifice (50-6-OO) configured to direct the upturned airstream 70-6 with an upward directional component relative to a centerline (50-6-CL) of an inlet (50-6-IN) of the upturned nozzle 50-6. The outlet orifice (50-6-OO) can have a straight flattened oval shape similar to the flat oval nozzle outlet orifice (50-3-OO) or a curved profile similar to the curved blade nozzle outlet orifice (50-4-OO). The upturned nozzle airstream 70-6 can have a suitable flow rate to nozzle area ratio at the round outlet orifice (50-6-OO). For example, the upturned nozzle airstream 70-6 can have a flow rate to nozzle area ratio in a range from 0.004 to 0.020 ($m^3$/min) to $mm^2$, more preferably in a range from 0.009 to 0.014 ($m^3$/min) to $mm^2$. The upturned nozzle outlet orifice (50-6-OO) can have any suitable cross-sectional area (e.g., in a range from 300 to 700 $mm^2$). The upturned nozzle outlet orifice (50-6-OO) can be configured to conform the shape of the upturned nozzle airstream 70-6 to better match the shape of the curved bodily region (e.g. back of knee, inner elbow, etc.), thereby more uniformly and completely imparting on the curved bodily region, which helps to maximize the coverage of the resulting distribution of the induced subsurface pressure changes 76.

Figure 22:
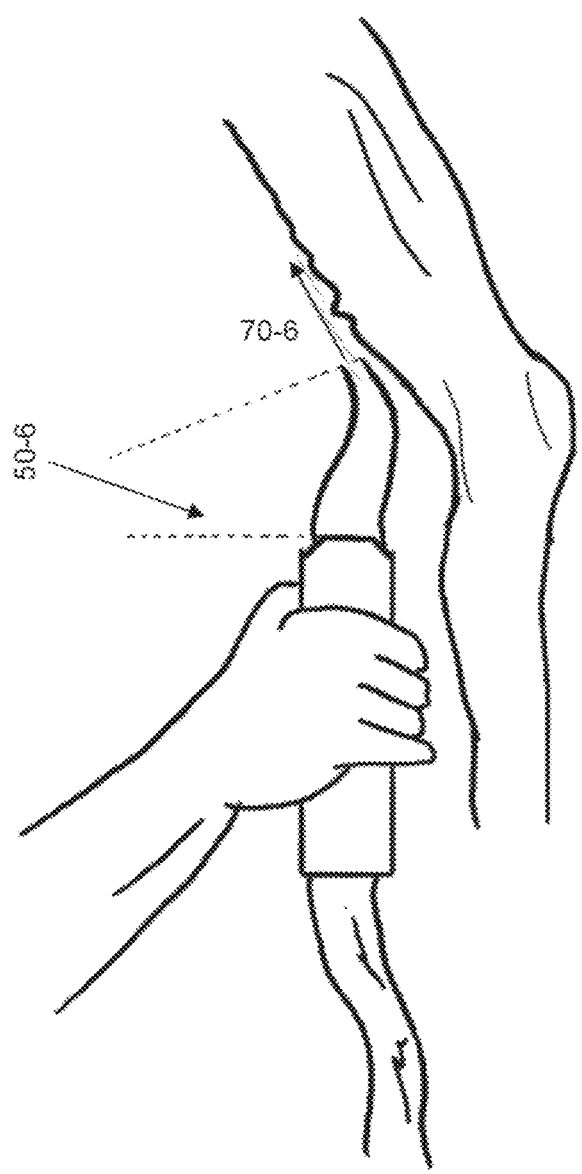
FIG. 22 illustrates operation of the upturned nozzle of FIG. 21 to apply the upturned airstream to a concave region of a patient to induce compressive shear thinning, stimulation, and directional movement of static fluid, in accordance with embodiments.

FIG. 22 illustrates operation of the upturned nozzle 50-6 to apply the upturned nozzle airstream 70-6 to a concave region of a patient to induce compressive shear thinning, stimulation, and directional movement of static fluid, in accordance with embodiments. As can be appreciated in view of FIG. 22, the upturned nozzle airstream 70-6 may be particularly effective for use in accomplishing act 84 of the method 80 to induce movement of static fluid within a concave bodily region because the upturned nozzle airstream 70-6 is output from the upturned nozzle 50-6 in a direction that accommodates orientation of the upturned nozzle 50-6 at a greater angle relative to the skin 74, thereby accommodating application of the upturned nozzle airstream 70-6 to concave areas of the body with reduced adjacent space available to accommodate a treatment nozzle used to accomplish act 82 and/or act 84 of the method 80.

Figure 23:
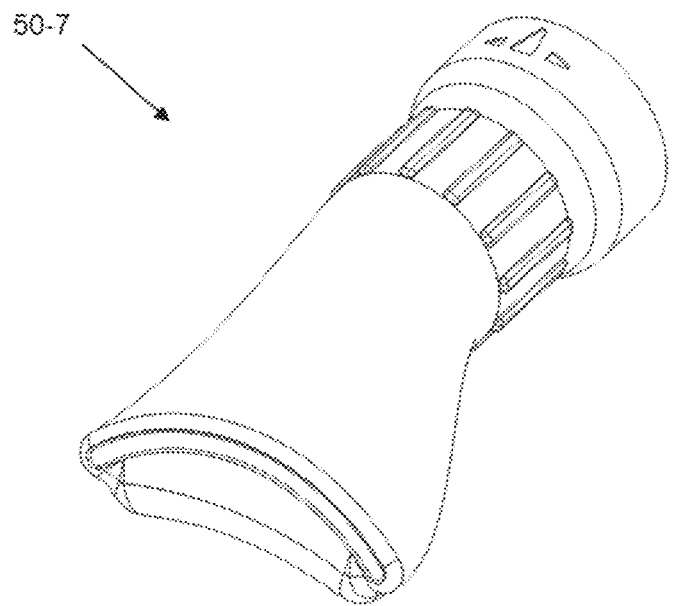
FIG. 23 and FIG. 24 show views of a bump nozzle having a protruding portion configured to be contacted with a patient to apply direct mechanical compression in combination with an airstream output from the bump nozzle for application to a patient to induce compressive shear thinning, stimulation, and directional movement of static fluid, in accordance with embodiments.
Figure 24:
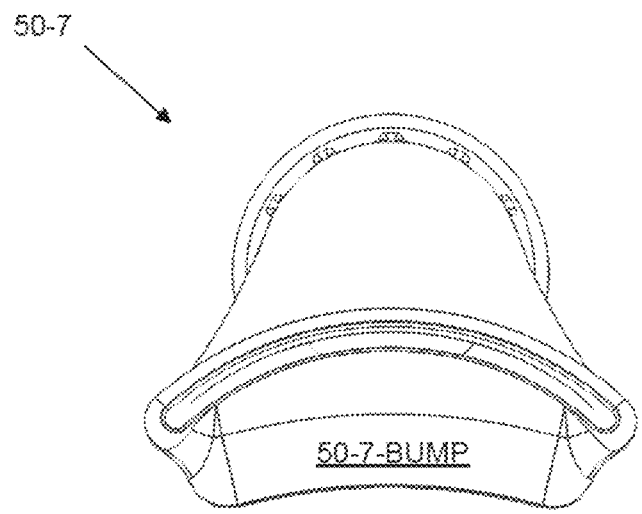

FIG. 23 and FIG. 24 show views of a bump nozzle 50-7 having a protruding bump (50-7-BUMP) configured to be contacted with a patient to apply direct mechanical compression in combination with an airstream 70-7 output from the bump nozzle 50-7 for application to a patient to induce compressive shear thinning, stimulation, and directional movement of static fluid, in accordance with embodiments. The bump (50-7-BUMP) is configured to be interfaced with and pushed against and along the skin 74 of the patient to mechanically stimulate tissue and aid in subcutaneous fluid movement towards the main drainage areas. The bump nozzle 50-7 can be used in instances where the fluid stasis is extreme (the skin is stiff) and an airstream 70 alone (output from any of the nozzles described herein) does not produce sufficient movement of fluid out of the fluid stasis area. Other than the bump (50-7-BUMP), the rest of the bump nozzle 50-7 can be configured the same or similar to the curved blade nozzle 50-4.

FIG. 25, FIG. 26, and FIG. 27 show views of a roller nozzle 50-8 having a roller (50-8-ROLLER) configured to be contacted with a patient to apply direct mechanical compression in combination with an airstream 70-8 output from the roller nozzle 50-8 for application to the patient to induce compressive shear thinning, stimulation, and directional movement of static fluid, in accordance with embodiments. The roller (50-8-ROLLER) is configured to be interfaced with and pushed against and rolled along the skin 74 of the patient to mechanically stimulate tissue and induce movement of static fluid. The roller nozzle 50-8 can be used in instances where the fluid stasis is extreme (e.g., the skin is stiff) and an airstream 70 alone (output from any of the nozzles described herein) does not produce sufficient movement of fluid out of the fluid stasis area. Other than the roller (50-8-ROLLER), the rest of the roller nozzle 50-8 can be configured the same or similar to the curved blade nozzle 50-4. In some embodiments, the roller (50-8-ROLLER) is configured to be lightly rolled along the surface of the skin 74 to apply compression to the skin 74 to induce directional movement of static fluid. The roller (50-8-ROLLER) can optionally be made from a hard, durable material like plastic or metal. Alternatively, the roller (50-8-ROLLER) can optionally be made from a softer more pliable material like rubber or foam, which may better conform to the anatomy and may be less traumatic to the skin and tissues.

Figure 28:
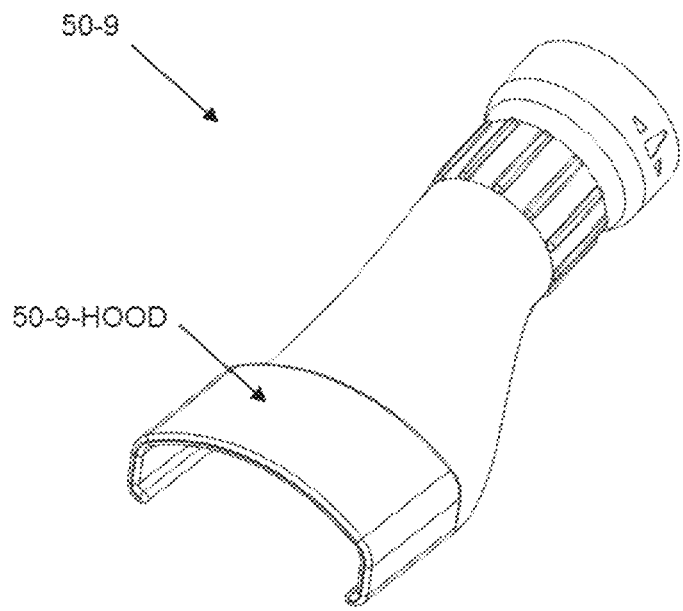
FIG. 28 shows an isometric view of a hooded nozzle having a hooded outlet configured to induce turbulence in an airstream output by the hooded nozzle for application to a patient to induce compressive shear thinning, stimulation, and directional movement of static fluid, in accordance with embodiments.
Figure 29:
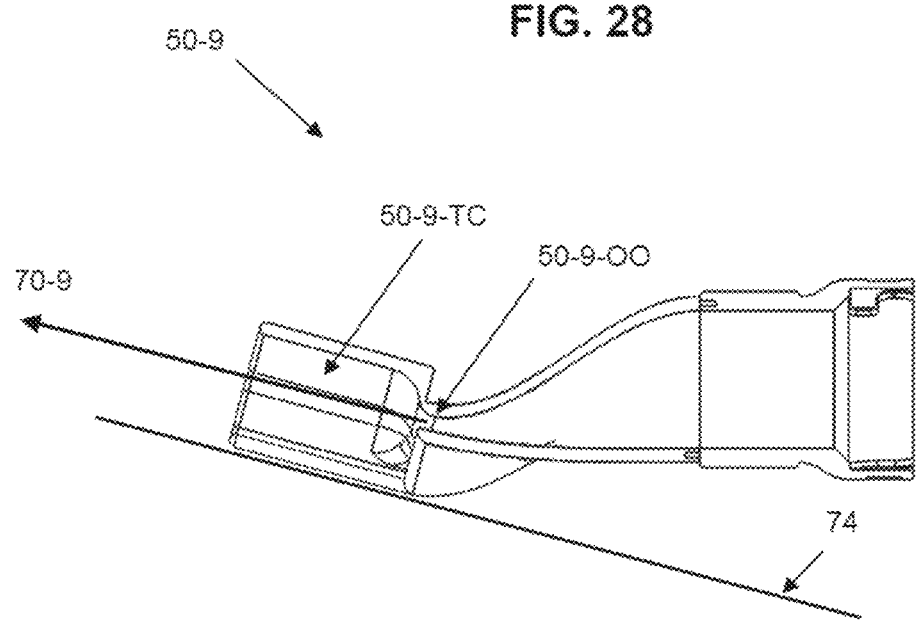
FIG. 29 shows a cross-sectional view of the hooded nozzle of FIG. 28.

FIG. 28 shows an isometric view of a hooded nozzle 50-9 that includes an outlet orifice (50-9-OO) and a hood (50-9-HOOD). FIG. 29 shows a cross-sectional view of the hooded nozzle 50-9. The hood (50-9-HOOD) partially defines a turbulence channel (50-9-TC) into which an airstream 70-9 is discharged from the outlet orifice (50-9-OO). End portions of the hood (50-9-HOOD) can be interfaced with the patient's skin 74, which, in combination with the hood (50-9-HOOD), defines the turbulence channel (50-9-TC). The turbulence channel (50-9-TC) has a larger cross-sectional area than the outlet orifice (50-9-OO), forming a larger low-pressure zone, causing the turbulence. The turbulence added to the airstream 70-9 may increase resulting variability in the induced subsurface pressure changes 76, and thereby may enhance associated shear thinning, create more intense/frequent wave mechanics, stimulation/conditioning of fluid movement pathways, and/or directional movement of static fluid.

Figure 30:
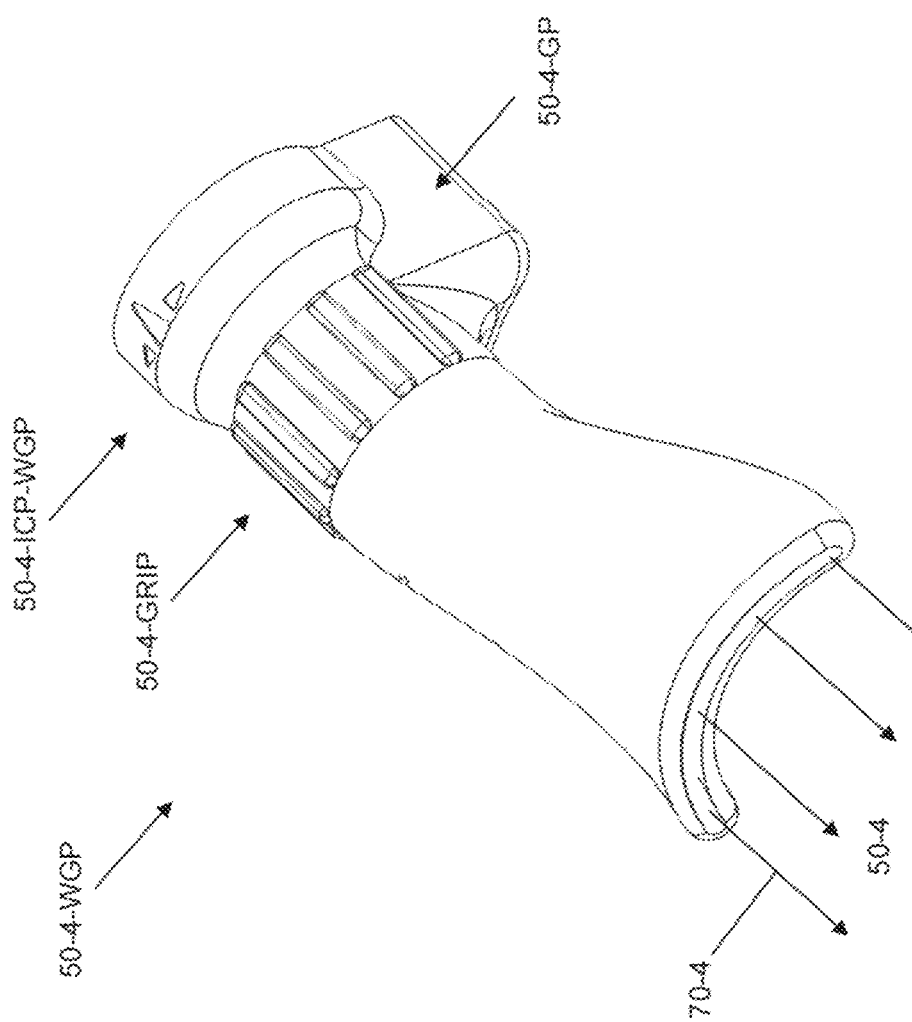
FIG. 30 shows an isometric view of a curved blade nozzle with a guide portion configured to be interfaced with the skin to control relative positioning of the curved blade nozzle relative to the skin, in accordance with embodiments.
Figure 31:
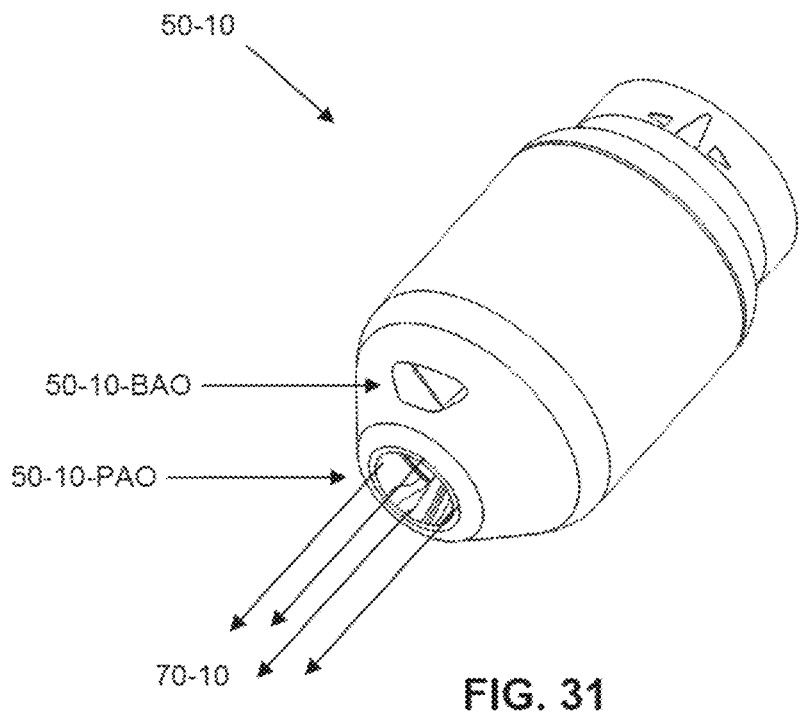
FIG. 31, FIG. 32, FIG. 33, and FIG. 34 illustrate a pulsation nozzle configured to output a pulsating airstream via induced rotation of an internal member for application to a patient to induce compressive shear thinning, stimulation, and directional movement of static fluid, in accordance with embodiments.
Figure 32:
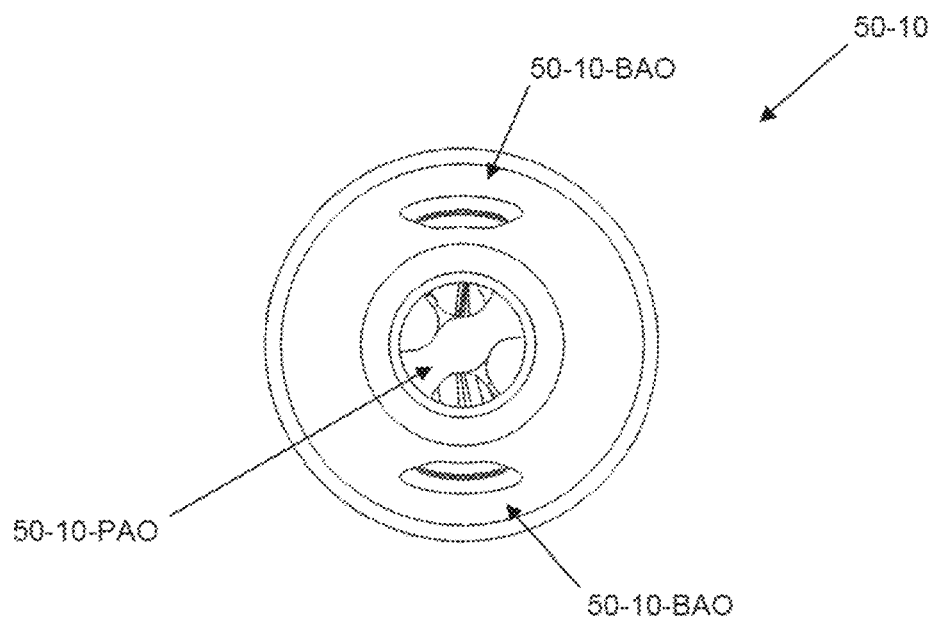
Figure 33:
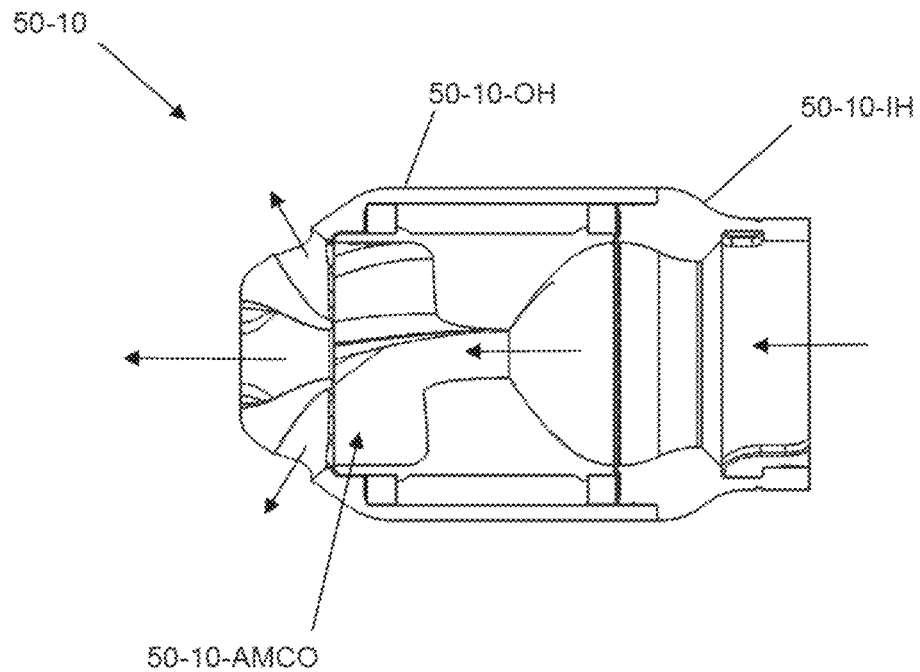
Figure 34:
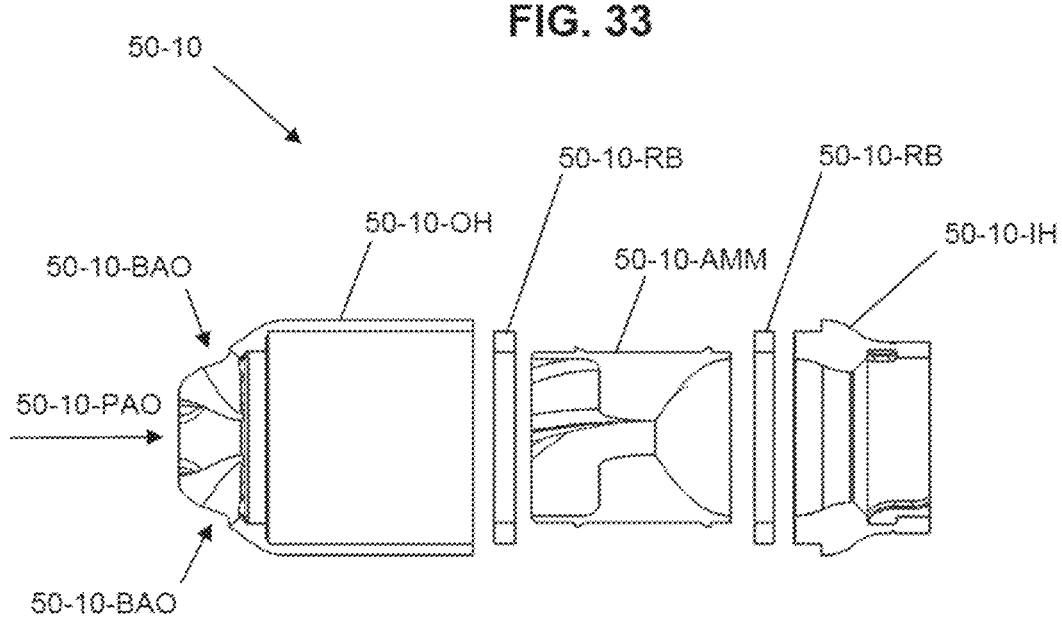
Figure 35:
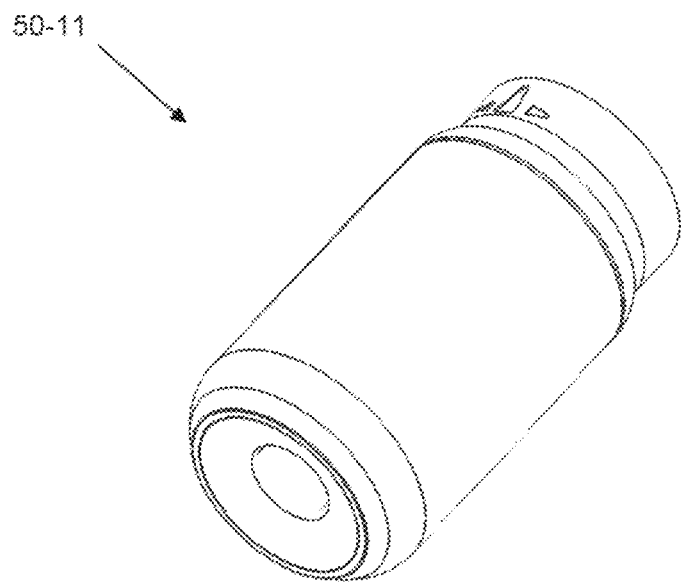
FIG. 35, FIG. 36, FIG. 37, FIG. 38, FIG. 39, and FIG. 40 illustrate a helical output nozzle configured to output a rotating helical airstream for application to a patient to induce compressive shear thinning, stimulation, and directional movement of static fluid, in accordance with embodiments.
Figure 36:
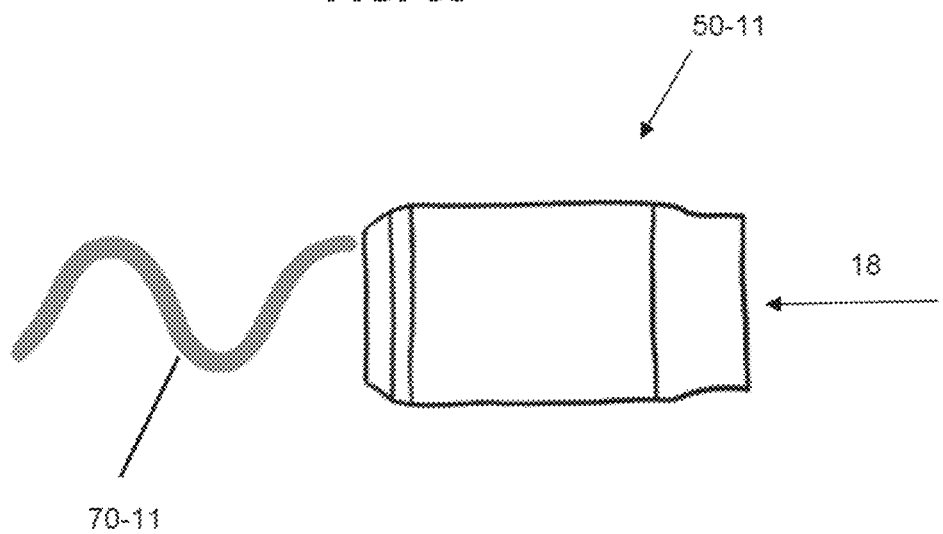

Any of the directional airstream nozzles described herein can include a guide portion configured to be interfaced with the patient to control the position and orientation of the outlet orifice and the airstream outputted there from relative to a zone of deployment for the airstream. For example, FIG. 30 shows an isometric view of a curved blade nozzle with a guide portion (50-4-WGP) configured to output a curved blade airstream 70-4 for application to a patient to induce compressive shear thinning of static fluid, stimulation/conditioning of a fluid movement pathway and/or a natural drainage area for static fluid, and/or directional movement of static fluid, in accordance with embodiments. The curved blade nozzle with a guide portion (50-4-WGP) is configured the same as the curved blade nozzle 50-4 except for having an inlet coupling portion (50-4-ICP-WGP) that includes a guide portion (50-4-GP) that forms a lower protruding portion of the inlet coupling portion (50-4-ICP-WGP). The guide portion (50-4-GP) has one or more external surfaces configured to be interfaced with the patient to control the position and orientation of the nozzle (50-4-WGP) relative to the patient to control the distance and orientation of the airstream curved blade airstream 70-4 relative to a zone of deployment of the airstream 70-4 on the skin. In the illustrated embodiment, the nozzle (50-4-WGP) has a grip portion (50-4-GRIP) distal to the inlet coupling portion (50-4-ICP-WGP) to accommodate grasping of the grip portion (50-4-GRIP) without interference by the guide portion (50-4-GP) and extension of fingers around the grip portion (50-4-GRIP).

FIG. 31, FIG. 32, FIG. 33, and FIG. 34 illustrate a pulsation nozzle 50-10 configured to output a pulsating airstream 70-10 for application to a patient to induce compressive shear thinning, stimulation, and directional movement of static fluid, in accordance with embodiments. The pulsating airstream 70-10 has a cyclically varying flow rate and velocity induced by the pulsation nozzle 50-10. The pulsation nozzle 50-10 includes an outlet housing (50-10-OH), an inlet housing (50-10-IH), an airflow modulation member (50-10-AMM), and rotary bearings (50-10-RB). The pulsation nozzle 50-10 can be assembled by installing both of the rotary bearings (50-10-RB) onto the airflow modulation member (50-10-AMM) on either end and pushing until flush with the bearing seats, followed by the insertion of this subassembly into the outlet housing (50-10-OH), followed by attachment of the inlet housing (50-10-IH) to the outlet housing (50-10-OH). The axial position of the airflow modulation member (50-10-AMM) is maintained via engagement with the rotary bearings (50-10-RB). The outlet housing (50-10-OH) includes a primary airflow outlet (50-10-PAO) and bypass airflow outlets (50-10-BAO). The airflow modulation member (50-10-AMM) is mounted for rotation relative to the outlet housing (50-10-OH) via the rotary bearings (50-10-RB) and defines an airflow modulation channel (50-10-AMC). The inlet housing (50-10-IH) includes an airflow inlet (50-10-INLET) configured to receive a supplied airflow 18 and deliver the supplied airflow 18 into the airflow modulation channel (50-10-AMC). The airflow modulation channel (50-10-AMC) includes internal surfaces shaped to induce rotation of the airflow modulation member (50-10-AMM), thereby inducing rotation of the supplied airflow 18 about the centerline of the nozzle body. The airflow modulation channel (50-10-AMC) has an airflow modulation channel outlet (50-10-AMCO) (shown in FIG. 33) with an elongated cross-sectional shape that extends transverse to an axis of rotation of the airflow modulation member (50-10-AMM). In the configuration shown in FIG. 32, the airflow modulation channel outlet (50-10-AMCO) is fluidly connected with the primary airflow outlet (50-10-PAO) and not fluidly connected with either of the bypass airflow outlets (50-10-BAO). Rotation of the airflow modulation member (50-10-AMM) produces periodic fluid connection of the airflow modulation channel outlet (50-10-AMO) with the bypass airflow outlets (50-10-BAO) for limited time durations, thereby venting a portion of the supplied airflow 18 out through the bypass airflow outlets (50-10-BAO) thereby causing the airstream 70-10 output from the primary airflow outlet (50-10-PAO) to include a pulsed axial flow variation. This vented air serves to keep the backpressure of the system constant when the PAO is not fully open, in turn, increase the longevity of the system/motor. The pulsed axial flow variation of the airstream 70-10 induces corresponding variations in the induced subsurface pressure changes 76, thereby enhancing the resulting compressive shear thinning of static fluid, stimulation and/or conditioning of fluid movements pathways, and/or directional movement of static fluid. The airstream 70-10 generated by the pulsation nozzle 50-10 can be employed as the airstream 70 in act 82 of the method 80 and/or the airstream 70 in act 84 of the method 80.

Figure 37:
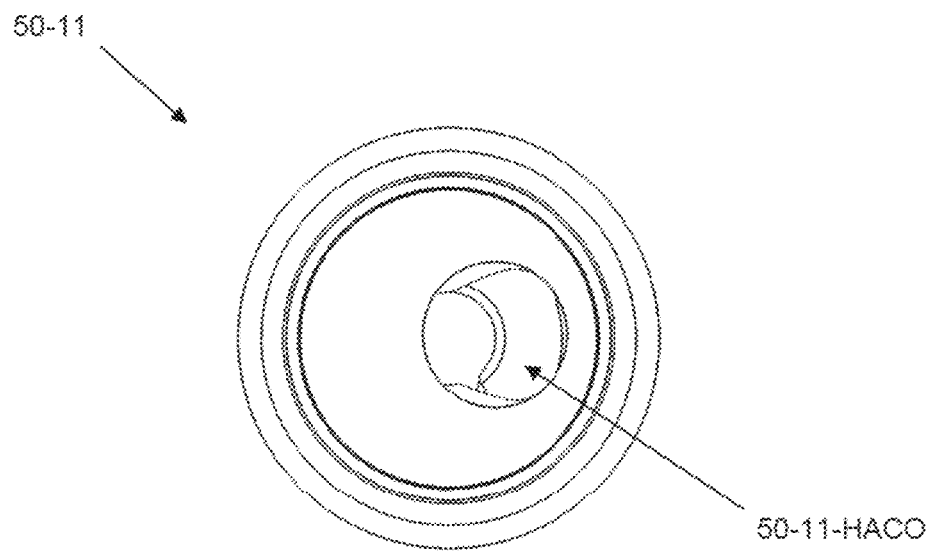
Figure 38:
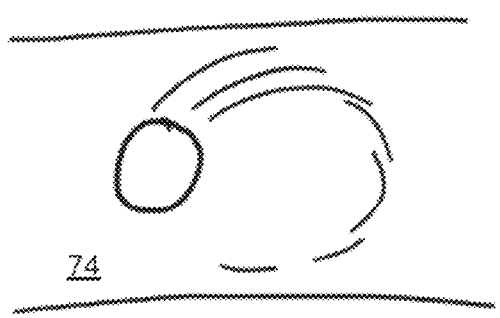
Figure 39:
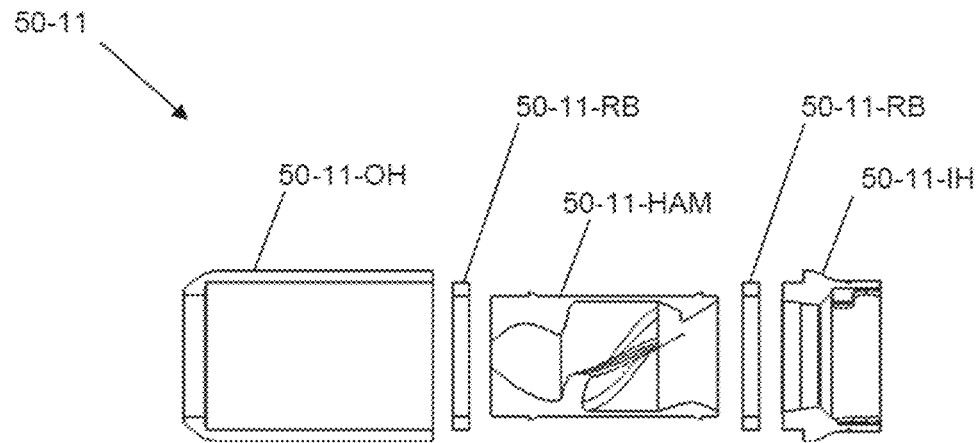
Figure 40:
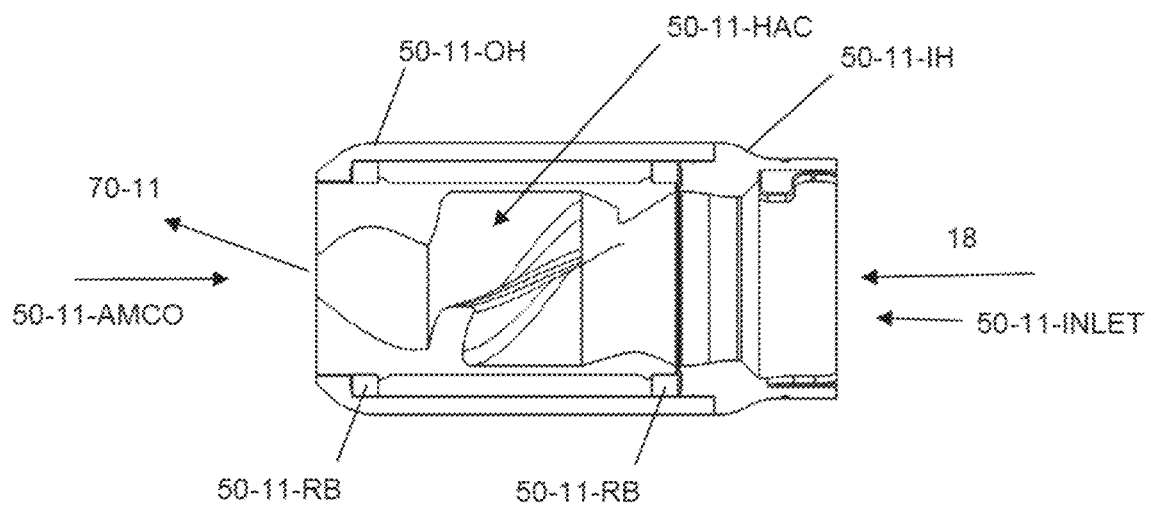

FIG. 35, FIG. 36, FIG. 37, FIG. 38, FIG. 39, and FIG. 40 illustrate a helical output nozzle 50-11 configured to output a rotating helical airstream 70-11 for application to a patient to induce compressive shear thinning, stimulation, and directional movement of static fluid, in accordance with embodiments. The helical output nozzle 50-11 includes an outlet housing (50-11-OH), an inlet housing (50-11-IH), a helical airflow member (50-11-HAM), and rotary bearings (50-11-RB)). The helical output nozzle 50-11 can be assembled by installing both of the rotary bearings (50-11-RB) onto the helical airflow member (50-11-HAM) on either end and pushing until flush with the bearing seats, followed by the insertion of this subassembly into the outlet housing (50-11-OH), followed by attachment of the inlet housing (50-11-IH) to the outlet housing (50-11-OH). The axial position of the helical airflow member (50-11-HAM) is maintained via engagement with the rotary bearings (50-11-RB). The helical airflow member (50-11-HAM) is mounted for rotation relative to the outlet housing (50-11-OH) via the rotary bearings (50-11-RB) and defines a helical airflow channel (50-11-HAC). The inlet housing (50-11-IH) includes an airflow inlet (50-11-INLET) configured to receive a supplied airflow 18 and deliver the supplied airflow 18 into the helical airflow channel (50-11-HAC). The helical airflow channel (50-11-HAC) includes internal surfaces shaped to induce rotation of the helical airflow member (50-11-HAM), thereby inducing rotation of the supplied airflow 18 about the centerline of the nozzle body. The helical airflow channel (50-11-HAC) has a helical airflow channel outlet (50-11-HACO) that is radially offset from a centerline of rotation of the helical airflow member (50-11-HAM) (as illustrated in FIG. 37). Rotation of the helical airflow member (50-11-HAM) rotates the helical airflow channel outlet (50-11-HACO) around the centerline of rotation of the helical airflow member (50-11-HAM), thereby producing the helically rotating configuration of the rotating helical airstream 70-11. The helically rotating configuration of the rotating helical airstream 70-11 produces a corresponding positional variation in the location of an area of deployment of the rotating helical airstream 70-11 on the patient's skin 74 (as illustrated in FIG. 38), thereby inducing corresponding variations in the induced subsurface pressure changes 76, thereby enhancing the resulting compressive shear thinning of static fluid, stimulation and/or conditioning of fluid movements pathways, and/or directional movement of static fluid. The airstream 70-11 generated by the helical airstream nozzle 50-11 can be employed as the airstream 70 in act 82 of the method 80 and/or the airstream 70 in act 84 of the method 80.

FIG. 41, FIG. 42, FIG. 43, and FIG. 44 illustrate a dual helical output nozzle 50-12 configured to output a rotating dual helical airstream for application to a patient to induce compressive shear thinning, stimulation, and directional movement of static fluid, in accordance with embodiments. The dual helical output nozzle 50-12 includes an outlet housing (50-12-OH), an inlet housing (50-12-IH), a dual helical airflow member (50-12-HAM), and rotary bearings (50-12-RB). The dual helical output nozzle 50-12 can be assembled by installing both of the rotary bearings (50-12-RB) onto the dual helical airflow member (50-12-HAM) on either end and pushing until flush with the bearing seats, followed by the insertion of this subassembly into the outlet housing (50-12-OH), followed by attachment of the inlet housing (50-12-IH) to the outlet housing (50-12-OH). The axial position of the dual helical airflow member (50-12-HAM) is maintained via engagement with the rotary bearings (50-12-RB). The dual helical airflow member (50-11-HAM) is mounted for rotation relative to the outlet housing (50-12-OH) via the rotary bearings (50-12-RB) and defines a dual helical airflow channel (50-12-DHAC). The inlet housing (50-12-IH) includes an airflow inlet (50-12-INLET) configured to receive a supplied airflow 18 and deliver the supplied airflow 18 into the dual helical airflow channel (50-12-DHAC). The dual helical airflow channel (50-12-DHAC) includes internal surfaces shaped to induce rotation of the dual helical airflow member (50-11-HAM), thereby inducing rotation of the supplied airflow 18 about the centerline of the nozzle. The dual helical airflow channel (50-11-DHAC) has two separate helical airflow channel outlets (50-12-HACO) that are radially offset from a centerline of rotation of the dual helical airflow member (50-12-HAM) (as illustrated in FIG. 41). Rotation of the dual helical airflow member (50-12-HAM) rotates the two helical airflow channel outlets (50-12-HACO) around the centerline of rotation of the dual helical airflow member (50-12-HAM), thereby producing the helically rotating configuration of the rotating dual helical airstream 70-12. The helically rotating configuration of the rotating dual helical airstream 70-12 produces a corresponding positional variation in the location of areas of deployment of the rotating dual helical airstream 70-12 on the patient's skin 74 (as illustrated in FIG. 42), thereby inducing corresponding variations in the induced subsurface pressure changes 76, thereby enhancing the resulting compressive shear thinning of static fluid, stimulation and/or conditioning of fluid movements pathways, and/or directional movement of static fluid. The rotating dual helical airstream 70-12 generated by the helical airstream nozzle 50-12 can be employed as the airstream 70 in act 82 of the method 80 and/or the airstream 70 in act 84 of the method 80.

In some embodiments, a deformable nozzle is used to generate the airstream 70 employed in act 82 of the method 80 and/or the airstream 70 employed in the act 84 of the method 80. The deformable nozzle can be configured with a deformable nozzle portion that can be selectively deformed to tailor the airstream 70 to better conform to the contours of the area being treated on a patient. In some embodiments, the deformable nozzle is formed from a suitable thermoplastic that can be heated to a heated state and reshaped in the heated state to reconfigure the airstream 70 to better conform to the contours of the area being treated on a patient. In some embodiments, the deformable nozzle is made from a malleable metal or thermoplastics that can be deformed to reshape the deformable nozzle to reconfigure the airstream 70 to better conform to the contours of the area being treated on a patient. The deformable nozzle can be configured similar to any of the nozzles described herein but with a deformable portion that can be selectively reshaped to tailor the airstream 70 to better conform to the contours of the area being treated on a patient, which can be a beneficial attribute since not all patient's anatomy share the same dimensions.

In some embodiments, the one or more internal features include one or more blades or flow directors. Many of the nozzles and hoses described herein have a smaller cross-sectional area or non-round shape, which may induce turbulence in the airflow flowing through the nozzle. Any of the nozzles, nozzle grips, or hoses described herein can further include one or more internal features within the nozzle to guide the airflow and create a more laminar, higher velocity flow.

Any of the systems described herein can include a quick-nozzle-change system configured to accommodate quick change from one embodiment of the airstream nozzle 50 attached to the airflow supply hose 14 to having a different embodiment of the airstream nozzle 50 attached to the airflow supply hose 14. Any suitable quick-nozzle-change can be employed. For example, in some embodiments, the quick-nozzle-change system includes a rotatable assembly (e.g., similar to the optical magnification system of a microscope) that includes multiple nozzles detachably mounted to the rotating assembly. The rotatable assembly can be selectively rotated to change which nozzle is fluidly coupled with the airflow supply hose 14. As another example, the quick-nozzle-change system can include a slidable linear assembly that includes multiple nozzles detachably mounted to the slidable linear assembly. The slidable linear assembly can be selectively translated to change which nozzle is fluidly coupled with the airflow supply hose 14.

Systems for Treating Fluid Stasis

Figure 44:
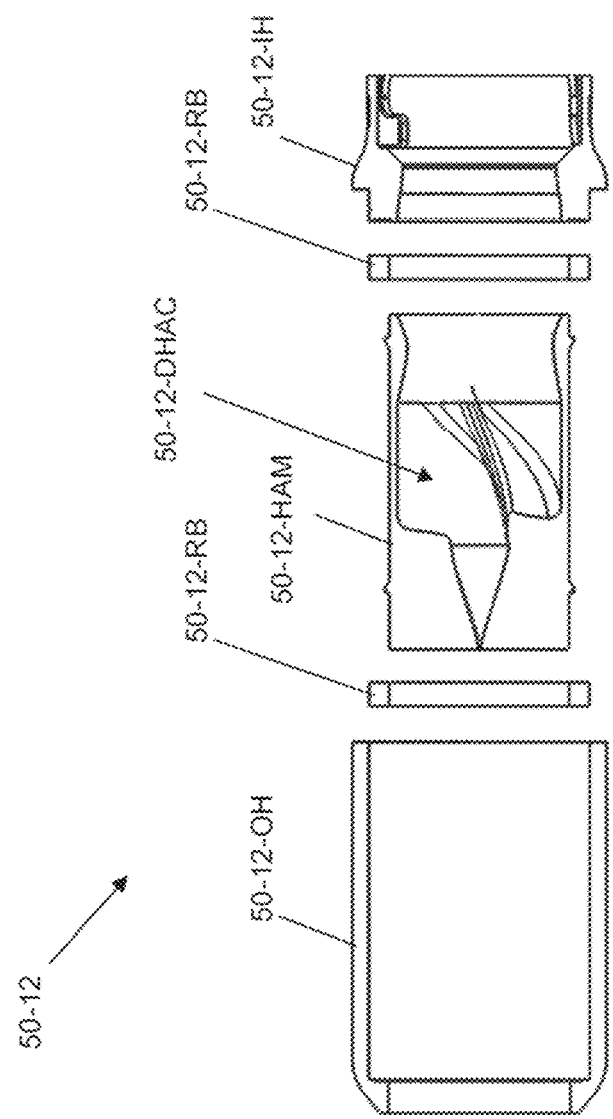

FIG. 44 illustrates an example blower unit 22 and airflow supply hose 14 configured to generate and deliver the supplied airflow 18 to the nozzle 50 for generating the airstream 70 for inducing shear thinning of static fluid, inducing movement of static fluid, and/or simulating/conditioning one or more lymphatic nodes, one or more lymphatic ducts, and/or blood vessels for transport and/or uptake of static fluid, in accordance with embodiments. In many embodiments, the supplied airflow 18 is generated from filtered, room temperature air. In many embodiments, the supplied airflow 18 is transferred from the blower unit 22 to the nozzle 50 via the airflow supply hose 14.

The blower unit 22 is intended for use in managing fluid stasis (e.g., edema). The airflow supply hose 14 is flexible and has a distal end portion 15 configured for selective coupling to any selected one of the nozzles described herein. The blower unit 22 includes a blower motor drivingly coupled to an airflow impeller operable to generate the airflow 18. In many embodiments, the blower unit 22 outputs the supplied airflow 18 to the airflow supply hose 14 at a suitable average flow rate to nozzle area ratio of (in units of ($m^3$/min) to $mm^2$) 0.004 to 0.020, more preferably in a range from 0.009 to 0.014. The optimum volumetric flow rate for the airflow 18 depends on the configuration of the nozzle employed, as well as on configurational parameters of the airflow supply hose 14 related to pressure loss along the airflow supply hose 14, such as length and internal diameter.

In preferred embodiments, the blower unit 22 includes a housing that encloses the motor and the airflow impeller. The housing can be made from any suitable material, such as metal or plastic. Preferably, blower unit 22 includes sound dampening features and/or materials disposed within the housing to reduce the intensity level of the sound generated via operation of the blower unit 22. For example, the blower unit 22 can include a high-density acoustic barrier textile like mass loaded vinyl that is arranged within the housing to surround the motor and the airflow impeller. Alternatively or additionally, the motor and the airflow impeller may be placed within a secondary housing design to inhibit transmission of sound. In some embodiments, the blower unit 22 includes noise-reduction features to mitigate the sound generated by the fan motor 40 and the impeller 42. The noise-reduction features can include, for example, sound-dampening materials (such as various forms of foam), a sound-limiting fan blade design, active noise cancelling units comprised of microphone and speakers, sound deadening motor mount, external baffles dampening the air coming into the air intake of the motor unit, and/or features on the nozzle 50 configured to limit the intensity of the sound generated as the airstream 70 exits the outlet orifice of the nozzle.

In many embodiments, the blower unit 22 includes a filtration assembly and a blower assembly configured to be operable to draw the airflow 18 through the filtration assembly to remove containments from the airflow 18 prior to the airflow 18 being received by the blower assembly. In many embodiments, the blower assembly includes a motor driven airflow impeller that pushes transfers the filtered airflow 18 to the airflow supply hose 14. The filtration of the airflow 18 by the filtration assembly is used to ensure that the airstream 70 is substantially free from contamination. In many embodiments, the filtration assembly includes a HEPA or N95 filter since both filter grades are rated for entrapment of particulates.

In many embodiments, the airflow supply hose 14 has a length and flexibility to accommodate case of maneuverability around the treatment subject. For example, the airflow supply hose 14 can optionally have a length in a range from 3 to 20 feet and optionally be made from a very flexible rubber or plastic and have a flexible external surface configuration (e.g., accordion, corrugated). The hose may be comprised of a set of hoses of different diameters, which neck down closer to the distal end using a coupling. The distal hose should be as short as possible, while still being maneuverable by the clinician, as to decrease the backpressure within the system. The airflow supply hose 14 has a distal end portion 15 configured for detachable coupling to the treatment nozzle 50 (which can be any of the treatment nozzles described herein). In embodiments, the airflow supply hose 14 is made from a material with suitably high heat conduction to cool the airflow 18 as the airflow 18 flows through the airflow supply hose 14. In embodiments, the airflow supply hose 14 is made from a rubber material with suitably high heat conduction and/or includes copper wiring configured to transfer heat from the airflow 18 to the ambient air surrounding the airflow supply hose 14 to cool the airflow 18.

In many embodiments, the blower unit 22 is configured to be operable to select and control one or more airflow parameters of the airflow 18 supplied to the airflow supply hose 14 by the blower unit 22. The one or more airflow parameters can include, but are not limited to, any combination of one or more of the temperature of the airflow, the pressure of the airflow 18 delivered to the airflow supply hose 14, the flow rate of the airflow 18 delivered to the airflow supply hose 14, variation in the flow rate of the airflow 18 delivered to the airflow supply hose 14 (to effect pulsation in the airstream 70 output from the nozzle 50), and the magnitude and frequency of the variation in the flow rate of the airflow 18). The ability to select and control the temperature of the airflow 18 can be used to ensure patient comfort and/or to increase the temperature of the skin 74 to increase mobility of static fluid out of the area of fluid stasis being treated and/or through a fluid pathway to a drainage area and/or be set to a cooler temperature for conditions that do not require heat such as lymphedema. The ability to select and control the flow rate, variation of the flow rate, and/or frequency of a variation in flow rate of the airflow 18 delivered to the airflow supply hose 14 can be used to select and control matching parameters of the airstream 70 output from the nozzle 50. The flow rate or velocity of the airstream 70 is an important airflow parameter to control, as different areas of the body may require different velocities for optimal treatment. For example, a lower air velocity may result in not enough fluid movement while having an air velocity that is excessively high may result in discomfort to the patient or may be desirable when treating areas such as the head. Various specific settings of the blower unit 22 may be preprogrammed and/or recommended for different specific bodily areas being treated for the convenience of the operator. In some embodiments, the blower unit 22 is configured to be operable to vary the flow rate of the airflow 18 delivered to the airflow supply hose 14 by a suitable magnitude at a suitable frequency so that the airstream 70 has a corresponding suitable pulsating flow rate/velocity to produce corresponding variations in the induced subsurface pressure changes 76, which may help enhance shear thinning of static fluid, stimulation/conditioning of the fluid movement pathway and/or the drainage area to which the fluid is directionally moved.

In embodiments, the blower unit 22 includes various control mechanisms to control various parameters. For example, blower unit 22 can include an airflow flow rate control mechanism operable to set the airflow rate of the airflow 18 delivered to the treatment nozzle 50 via the airflow supply hose 14. In some embodiments, the power supplied to the motor is controlled via the airflow rate control mechanism, which can include a dial or rheostat that can optionally have settings that correspond to selectable flow rates for the airflow 18 (or selectable velocities for the airflow 18 or the airstream 70) and/or settings that correspond to airflow rates for the airflow 18 for treating specific body regions to be treated using the selected airflow rate for the airflow 18. For example, blower unit 22 can include an airflow rate selection dial that includes settings for treating specific body regions such as, for example, a "face" setting, a "leg" setting, etc. The "face" setting can be used to select a reduced airflow rate for the airflow 18 suitable for treatment of the face so as not to harm the more sensitive structures of the face as opposed to the "leg" setting, which may provide a more powerful stream of air to better move fluid through a leg.

Any of the systems for treating fluid stasis described herein can optionally be configured to select and control the temperature of the airflow 18. If the temperature of the airstream 70 is either too cold or too hot, deployment of the airstream 70 on the patient may cause patient discomfort and/or may inhibit movement of static fluid. Preferably, the selected temperature of the airstream 70 will be in a range from 20 C to 45 C at the nozzle opening for treating fluid stasis (e.g., edema). For inducing evaporative cooling (as described herein), the selected temperature may be in a lower temperature range (e.g., 5° C. to 20 C).

Any of the systems for treating fluid stasis described herein can optionally be employed for inducing evaporative cooling of a subject. For example, the airstream 70 can be directed onto the subject to induce an accelerated evaporative cooling effect on the skin 74. The system can be optionally configured to receive a temperature selection and control the temperature of the airstream 70 accordingly to the temperature selection, which can be within a suitable temperature range for evaporative cooling (e.g., 5 C to 20 C). Inducing evaporative cooling may be beneficial in various situations. For example, as a result of physical exertion, a subject may be hot and sweaty due to muscle contraction and/or higher blood perfusion. Cooling of a hot and sweaty subject can be induced by directing the airstream 70 (preferably with a suitable cool temperature in a range from 5 C to 20 C) onto the subject to interact with the sweat on the body to evaporate the sweat at a rapid rate. In a sports medicine and recovery setting, inducing evaporative cooling as described herein can be used to rapidly cool the subject, thereby reducing post-exertion recovery time, and increasing the subject's ability to get back "on the field" quicker. In addition, blowing cool air onto a subject may have influence on the sympathetic nervous system's control over bodily sweating, which may inhibit sweating post treatment. Optionally, a liquid cooling agent (water or alcohol) can be applied to the skin 74 prior to or during application of the airstream 70 to increase the rate of evaporative cooling.

In some embodiments, the blower unit 22 is configured for (and controllable to) generating the airflow 18 with an airflow configuration selected from selectable airflow configurations. The selectable airflow configurations can include a constant flow rate configuration (i.e., having a constant flow rate of the airflow 18) and a pulsated airflow configuration (i.e., having a pulsating variation in flow rate of the airflow 18). Any suitable approach can be used by the blower unit 22 to generate the pulsated airflow configuration. For example, the blower unit 22 can be configured to control operation of the motor to vary the speed of the airflow impeller to implement the pulsated airflow configuration. Alternatively or additionally, blower unit 22 can include (and be configured to control) an electrically operated valve to control the flow rate of the airflow 18 to implement the pulsated airflow configuration. The blower unit 22 can control the pulsation of the airflow 18 via a software algorithm. The flow rate of the airflow 18 can be pulsated many times per second so as to achieve enhanced agitation of static fluid via the airstream 70 in order to enhance shear thinning and fluid movement. Pulsation, temperature, velocity, and other fluid control parameters may be controlled simply via analog switches or dials on the blower housing or the nozzle or managed using touch screen displays or other digital means.

The systems for treating fluid stasis described herein can be configured to generate and output feedback indicative of one or more of the relative position of the nozzle 50 relative to an deployment zone of the airstream 70 on the patient, a relative orientation of the nozzle 50 relative to the patient, the temperature of the skin 74 adjacent to the nozzle 50, the angle of the airstream 70 relative to the skin 74 in the deployment zone of the airstream 70 on the patient, the size and frequency of wave-like motions of the skin 74 at or near the deployment zone of the airstream 70 on the patient, or an amount of static fluid remaining within the tissue. The feedback is configured to provide information to the therapist conducting the fluid stasis treatment for use in conducting the treatment and to monitor the progress of the treatment in real-time. In some embodiments, the systems for treating fluid stasis described herein include electrical impedance sensors that are employed to measure the amount of fluid within the tissue. The use of electrical impedance sensors to detect fluid stasis is a proven methodology, particularly with respect to detecting lymphedema. Each of the nozzles described herein can include integrated electrical impedance sensors configured to be contacted with the skin 74 to generate an electrical impedance sensor signal that is processed to determine an amount of remaining fluid within a local area of the skin 74. This embodiment may look similar to the bump nozzle, where the electrodes are attached to the anterior of the bump on either end. During treatment, the clinician will temporarily place these electrodes onto the patient's edematous area in question and read the bioimpedance reading, and alter treatment based off of this. In embodiments, the blower system may read this bioimpedance reading and show progress and recommendations of treatment on a digital screen as well as modify/end treatment based on this feedback. Alternatively, the electrical impedance sensors can be part of another subsystem instead of being integrated into the nozzle 50.

The systems for treating fluid stasis described herein can be configured for use in a stationary setting and/or in a mobile setting. For example, in some embodiments, the blower unit 22 can be configured for use in a dedicated stationary treatment facility. Alternatively or additionally, the blower unit 22 can be configured as a mobile unit that includes mobility features (e.g., a handle, wheels, body straps, backpack straps, etc.).

Figure 46:
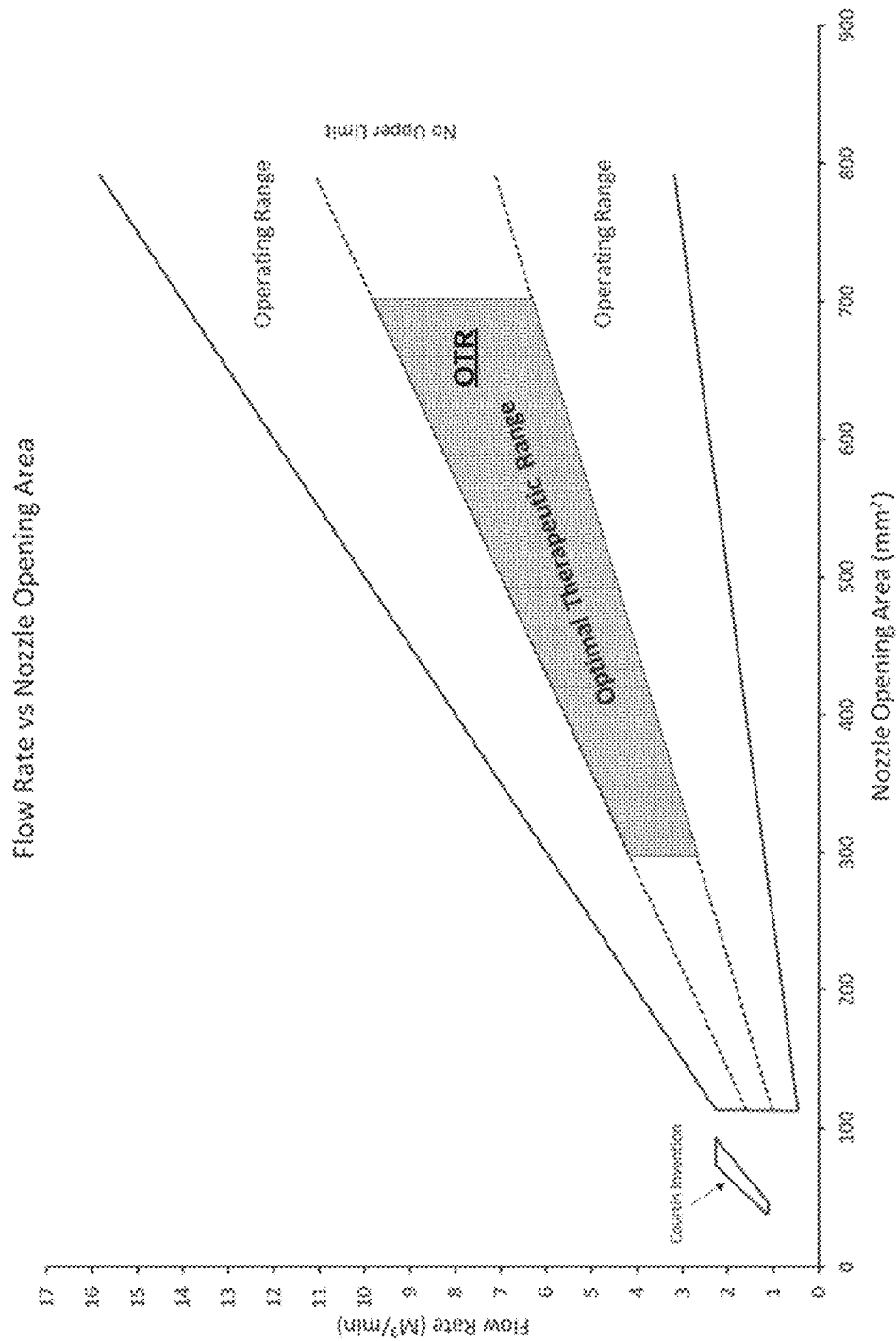
FIG. 46 illustrates an example operational regime for an airstream for inducing shear thinning of static fluid, inducing movement of static fluid, and/or simulating/conditioning one or more lymphatic nodes, one or more lymphatic ducts, and/or blood vessels for transport and/or uptake of static fluid, in accordance with embodiments.

FIG. 46 illustrates an example operational regime in terms of nozzle opening area and flow rate for the airstream 70 for inducing shear thinning of static fluid, inducing movement of static fluid, and/or simulating/conditioning one or more lymphatic nodes, one or more lymphatic ducts, and/or blood vessels for transport and/or uptake of static fluid, in accordance with embodiments. As illustrated, the systems and methods for treating fluid stasis described herein can employ an airstream nozzle with an outlet orifice cross-sectional area of at least 113 $mm^2$ for an overall operating range envisioned for the airstream 70. An envisioned optimal therapeutic range (OTR) extends from a minimum outlet orifice cross-sectional area of 300 $mm^2$ with flow rate in a range from 2.7 $m^3$/min to 4.2 $m^3$/min up to a maximum outlet orifice cross-sectional area of 700 mm2 with a flow rate in a range from 6.2 $m^3$/min to 9.8 $m^3$/min. In contrast, U.S. Pat. No. 3,163,161 is directed to a traveling wave air massaging method in which air is directed to the skin at a low angle using smaller nozzle outlets and compressed air.

Figure 47:
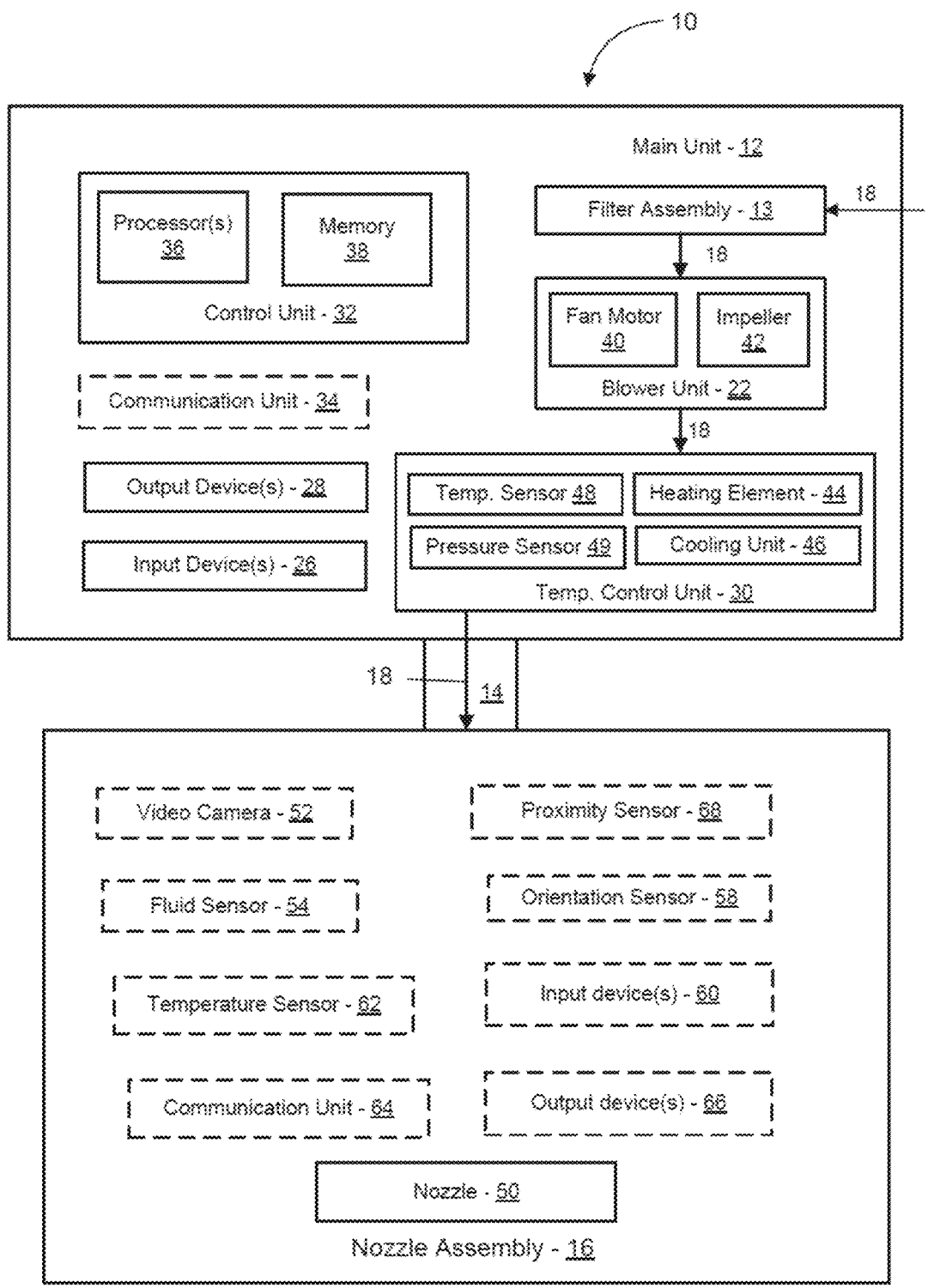
FIG. 47 is a simplified schematic diagram of a system for treating fluid stasis via application of one or more airstreams to a patient, in accordance with embodiments.

FIG. 47 is a simplified schematic diagram of a system 10 for treating fluid stasis, in accordance with embodiments. System 10 includes a main unit 12, the airflow supply hose 14, and a nozzle assembly 16. The main unit 12 is configured to generate and supply an airflow 18 to the nozzle assembly 16 via the airflow supply hose 14. As described herein, the nozzle assembly 16 is configured to receive the airflow 18 and output the airflow 18 as the airstream 20 employed to effect acts 82 and/or 84 of the method 80.

The main unit 12 includes the blower assembly 22, the filter assembly 24, one or more input devices 26, and one or more output devices 28. The main unit 13 can optionally further include an airflow temperature control unit 30, a control unit 32, and/or a communication unit 34. The control unit 32 can include one or more processors 36 and a tangible memory 38 storing non-transient instructions executable by the processor(s) 36 for controlling operation of the blower unit 22, the airflow temperature control unit 30, and/or the communication unit 34. The one or more input devices 26 are user operable to input control signals into the main unit 12 for use in setting operational parameters for the blower assembly 22 and/or the airflow temperature control unit 30. The one or more output devices 28 are operable to display selected or current operational parameters of the blower assembly 22 and/or the airflow temperature control unit 30. The blower assembly 22 includes an impeller motor 40 and an airflow impeller 42 drivingly coupled to the impeller motor 40. The impeller motor 40 rotates the airflow impeller 42, which draws the airflow 18 through the filter assembly 13 and delivers the airflow 18 to the airflow temperature control unit 30. The airflow temperature control unit 30 includes a heating element 44, an airflow cooling unit 46, an airflow temperature sensor 48, and an airflow pressure sensor 49. The airflow temperature sensor 48 is configured to generate an airflow temperature signal indicative of the temperature of the airflow 18 downstream of the airflow temperature control unit 30. The control unit 32 controls the heating element 44 based on the temperature signal to heat the airflow 18, when required, to a selected temperature for the airflow 18 downstream of the airflow temperature control unit 30. The control unit 32 controls the heating element 44 based on the temperature signal to heat the airflow 18, when required, to a selected temperature for the airflow 18. In some embodiments, the cooling unit 46 is configured as an air-to-air heat exchanger through which the airflow 18 passes and an electric fan for generating a cooling airstream over the air-to-air heat exchanger. Alternatively, the cooling unit 46 can be configured as an air-conditioning unit with an evaporator for removing heat from the airflow 18. The control unit 32 can control the electric fan or the air-conditioning unit 46 to cool the airflow, when required, to a selected temperature for the airflow 18. From the airflow temperature control unit 30, the airflow 18 is output to the air hose 14 for delivery to the nozzle assembly 16. The airflow pressure sensor 49 is configured to generate an airflow pressure signal indicative of the pressure of the airflow 18 output to the airflow supply hose 14. In some embodiments, the control unit 32 is configured to control operation of the fan motor 40 to control the pressure of the airflow 18 and thereby control the flow rate of the airflow 18. In some embodiments, the input devices(s) 26 are operable to specify a flow rate for the airflow 18, which the control unit 32 can control via the pressure signal provided by the airflow pressure sensor 49.

The nozzle assembly 16 includes a nozzle 50, which can be any of the nozzles 50-1 through 50-12 described herein. The nozzle assembly 16 can further include any selection of additional components that includes one or more of a video camera 52, a fluid sensor 54, an orientation sensor 58, one or more input devices 60, a temperature sensor 62, a communication unit 64, one or more output devices 66, or a proximity sensor 68. Video camera 52 can be mounted to the nozzle 50 and oriented to monitor movement of the skin 74 in an area of deployment of the airstream 70 on the skin 74. Output from the video camera 52 can be transmitted wirelessly (or via wires) from the communication unit 64 of the nozzle assembly 16 to the communication unit 34 of the main unit 12 for processing by the control unit 32 to estimate an amount of static fluid in the tissue in the area of deployment. The control unit 32 can then output feedback indicative of the estimated amount of static fluid in the tissue in the area of deployment to the user of the system via the one or more output devices 28 of the main unit 12 and/or via the one or more output devices 66 of the nozzle assembly 16. Fluid sensor 54 can be configured to generate a fluid sensor signal indicative of the amount of static fluid in the tissue. Fluid sensor 54 can have any suitable configuration. For example, in some embodiments, the fluid sensor 54 includes an electrical impedance sensor that includes two or more electrodes (preferably four total with two signal electrodes and two sense electrodes) configured to be contacted with the skin 74 to generate an electrical impedance signal indicative of the impedance of tissue between to the two sense electrodes. The fluid sensor 54 can be mounted to the nozzle 50 or separately deployed. The fluid sensor signal can be transmitted wirelessly (or via wires) from the communication unit 64 of the nozzle assembly to the communication unit 34 of the main unit 12 for processing by the control unit 32 to estimate an amount of static fluid in the tissue in the area of deployment. The control unit 32 can then output feedback indicative of the estimated amount of static fluid in the tissue in the area of deployment to the user of the system via the one or more output devices 28 of the main unit 12 and/or via the one or more output devices 66 of the nozzle assembly 16. Pressure sensor 56 can be configured to generate a pressure signal indicative of the pressure of the airflow 18 within the nozzle 50 upstream of the output orifice of the nozzle 50. The pressure signal can be transmitted wirelessly (or via wires) from the communication unit 64 of the nozzle assembly 16 to the communication unit 34 of the main unit 12 for processing by the control unit 32 for use in controlling the fan motor 40 to control the flow rate of the airflow 18 through the nozzle 50. The orientation sensor 58 (e.g., an accelerometer) can be used to generate an orientation signal indicative of the orientation of the nozzle 50 relative to gravity. The orientation signal can be transmitted wirelessly (or via wires) from the communication unit 64 of the nozzle assembly 16 to the communication unit 34 of the main unit 12 for processing by the control unit 32 to determine the orientation of the nozzle 50 relative to gravity. The control unit 32 can then output feedback indicative of the orientation of the nozzle 50 to the user of the system via one or more output devices 28 of the main unit 12 and/or via the one or more output devices 66 of the nozzle assembly 16.

For optimal movement of static fluid, the angle at which the airstream 70 contacts the skin 74 can be controlled to enhance the efficacy of the treatment. Preferably, the angle of the airstream 70 relative to the skin 74 is between 0 deg and 60 deg., depending on the proximity to the skin 74. The angle of the airstream 70 relative to the skin 74 can be selected to provide a suitable balance between compressive fluid thinning and direction movement of static fluid. The angle of the airstream 70 relative to the skin 74 can be selected to maximize wave-like movements of the skin 74 to enhanced shear thinning of static fluid and directional movement of static fluid. To provide feedback to a clinician manipulating the nozzle assembly 16, the nozzle assembly 16 can be configured with an orientation sensor 58 for measuring the orientation of the nozzle 50 to provide feedback to the user as to the orientation of the nozzle 50. The orientation sensor 58 can have any suitable configuration. For example, the orientation sensor 58 can be configured similar to a bubble-sensor on a common carpenter's level. Alternatively or additionally, orientation sensor 58 can include an accelerometer configured to generate an accelerometer output signal indicative of the orientation of the nozzle 50 relative to gravity as described above. The nozzle 50 can also include a simple guide configured as part of the underside of the nozzle 50 or as an attachment to the nozzle 50. The guide can be configured so that when the guide is placed flush against the patient, the nozzle 50 is oriented relative to the skin 74 for outputting the airstream 70 onto the skin 74 at a suitable angle relative to the skin 74.

In some embodiments, the nozzle assembly 16 includes a proximity sensor 68 for measuring proximity of the outlet orifice of the nozzle 50 to the area of deployment of the airstream 70 on the skin 74. The proximity sensor 68 can have any suitable configuration. For example, in some embodiments, the proximity sensor 68 includes an ultrasonic distance sensor or a laser distance sensor configured to generate a proximity sensor signal indicative of the distance between the outlet orifice of the nozzle 50 and the area of deployment of the airstream 70 on the skin 74. The proximity sensor signal can be transmitted wirelessly (or via wires) from the communication unit 64 of the nozzle assembly 16 to the communication unit 34 of the main unit 12 for processing by the control unit 32 to estimate a distance between the outlet orifice of the nozzle 50 and the area of deployment of the airstream 70 on the skin 74. The control unit 32 can then output feedback indicative of the estimated distance between the outlet orifice of the nozzle 50 and the area of deployment to the user of the system via the one or more output devices 28 of the main unit 12 and/or via the one or more output devices 66 of the nozzle assembly 16. The feedback can be configured to give guidance to the user to achieve optimum positioning of the nozzle 50 relative to the area of deployment for optimal shear thinning and movement of static fluid. The optimal nozzle distance depends on the nozzle type, velocity, patient skin integrity and sensitivity, and state of fluid stasis. The optimum distance may vary in an approximate range from 0 cm to 50 cm. In some instances, it may be beneficial to contact skin directly with the outlet orifice of the nozzle 50 depending on patient tolerance and skin integrity. In embodiments, a physical or electronic nozzle spacer may be utilized to set the distance between the outlet orifice of the nozzle 50 and the skin 74.

In some embodiments, the nozzle assembly 16 includes a temperature sensor 62 for measuring skin temperature and/or the temperature of the airstream 70. The temperature of the airstream 70 can be used to ensure suitable temperature of the airstream 70 for patient comfort and/or treatment efficacy. The temperature of the skin 74 may be indicative of the amount of movement of static fluid occurring.

As described above, a video camera 52 can be integrated into the nozzle assembly 16 in order to detect various changes occurring in the skin 74 with respect to wave-like movements of the skin 74 induced by the imparting of the airstream 70 on the skin 74. For example, the control unit 32 can implement software algorithm to detect changes in the height and/or frequency of the ripples or perturbations being created in the skin, which can be indicative of the amount of static fluid remaining in the tissue.

In embodiments, the output devices 66 of the nozzle assembly 16 (or any other part of the system) include a display screen for the purpose providing quantitative data to the user resulting from the use of the aforementioned sensors. Likewise, simple LED lights may be utilized to provide user feedback with respect to the sensors. For example, a green LED on the nozzle may illuminate when the laser sensor detects that the output orifice of the nozzle 50 is within a prescribed range of distances from the area of imparting of the airstream 70 on the skin 74 of the patient.

Figure 48:
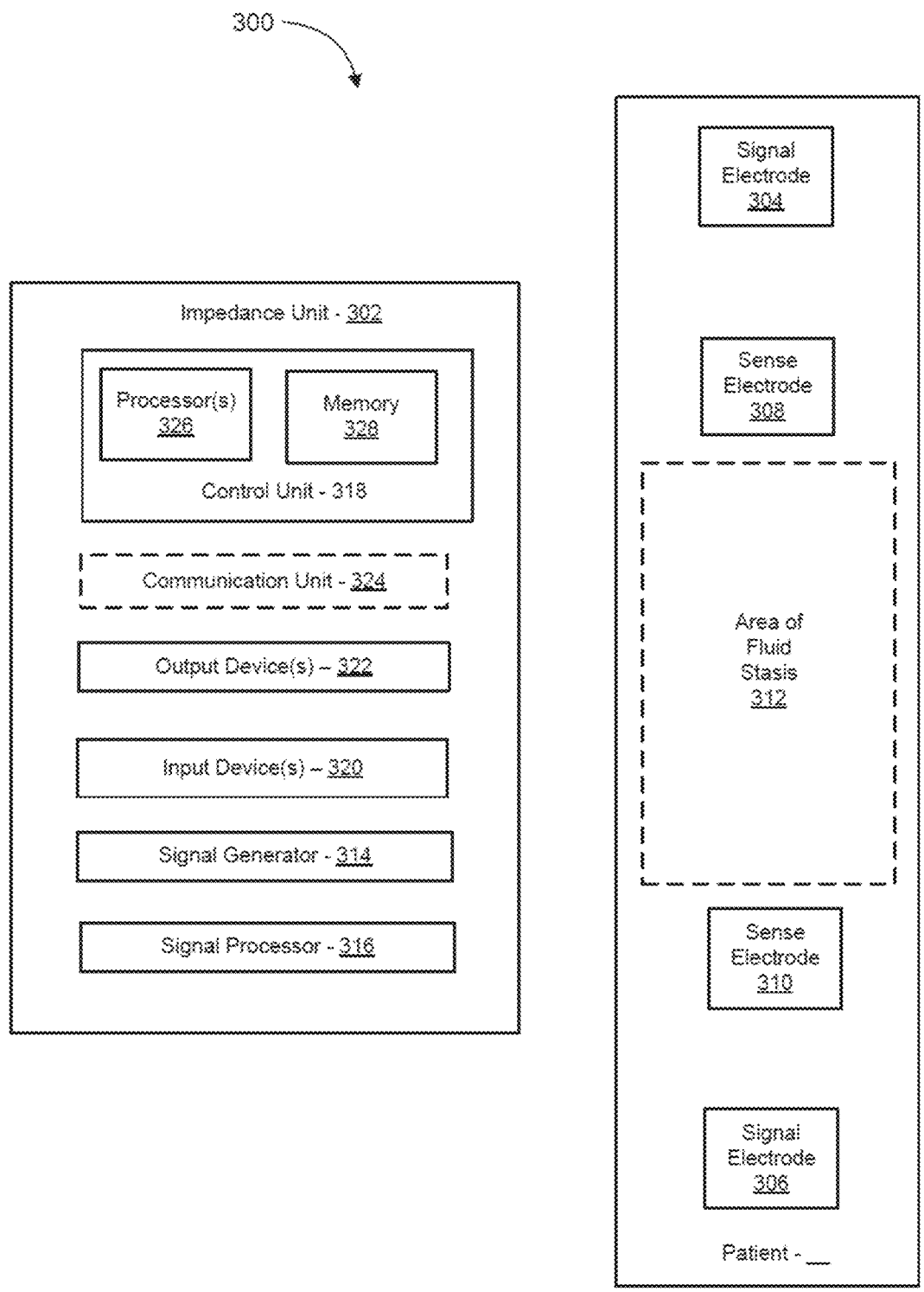
FIG. 48 is a simplified schematic diagram of an impedance system for measuring the extent of static fluid in a fluid stasis area, in accordance with embodiments.
Figure 49:
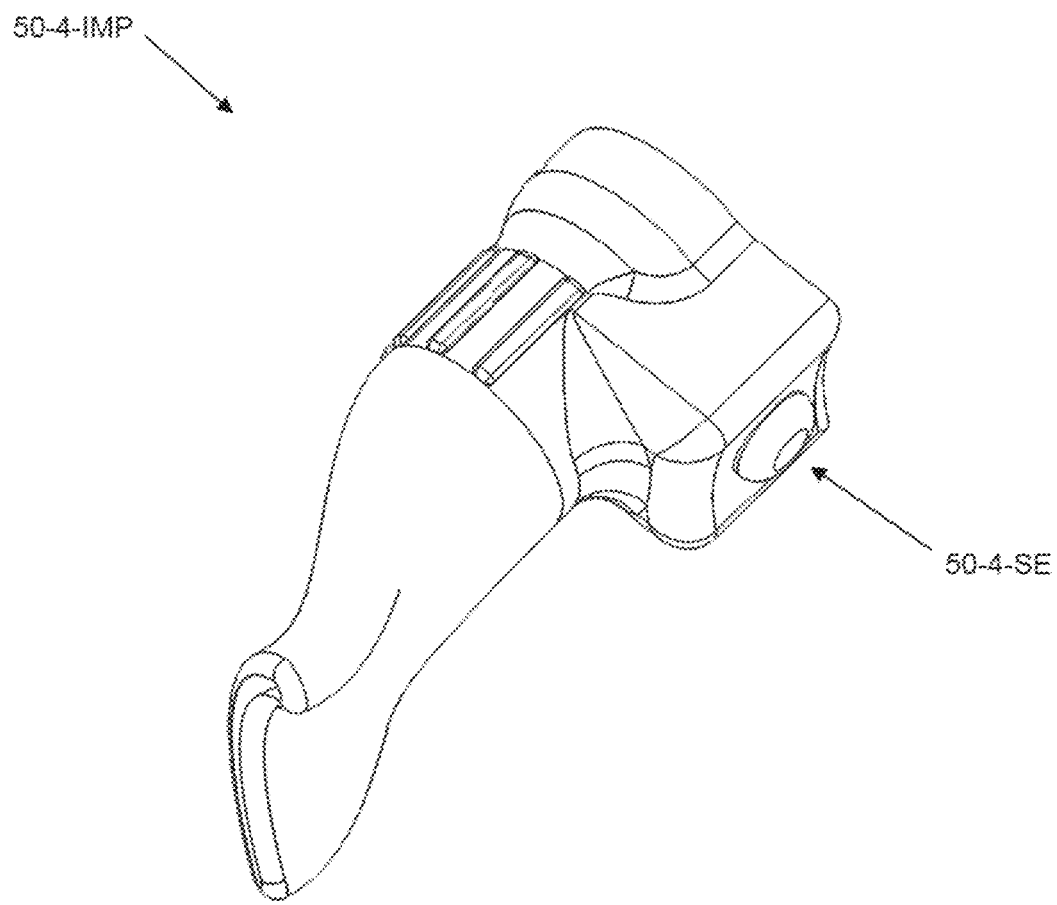
FIG. 49 shows a view of a directional airstream nozzle that includes an impedance electrode for use in measuring the extent of static fluid in a fluid stasis area, in accordance with embodiments.

FIG. 48 is a simplified schematic diagram of an impedance-based static fluid measurement system 300 that can be used in conjunction with the fluid stasis treatment system 10, in accordance with embodiments. The static fluid measurement 300 includes an impedance unit 302, signal electrodes 304, 306, and sense electrodes 308, 310. The signal electrodes 304, 306 are configured to be interfaced with the skin of the patient in a spaced apart manner to transmit an electrical signal through tissue of the patient disposed between the signal electrodes 304, 306. The sense electrodes 308, 310 can be positioned on either side of an area of fluid stasis 312 to monitor a resulting electrical potential across the area of fluid stasis 312 induced by the signal electrodes 304, 306. The impedance unit 302 includes a signal generator 314, a signal processor 316, a control unit 318, one or more input devices 320, one or more output devices 322, and a communications unit 324. The control unit 318 includes one or more processors 324 and a memory 326. The signal generator 314 generates and supplies the electrical signal to the signal electrodes 304, 306 for application to the patient. The signal processor 316 processes the resulting electrical potential across the area of fluid stasis 312 measured by the sense electrodes 308, 310 and generates impedance data indicative of the impedance of the area of fluid stasis 312. The memory stores non-transitory instructions executable by the one or more processors 316 to perform the actions described herein. The one or more processors 316 process the impedance data generated by the signal processor 316 to estimate an amount of static fluid in the area of fluid stasis 312 based on the impedance data generated by the signal processor 316 using any suitable known approach. The one or more processors 316 control the one or more output devices 322 to provide feedback to an operator of the fluid stasis treatment system 10 indicative of an amount of static fluid disposed within the area of fluid stasis 312, which can be used to assess progress of the fluid stasis treatment. The one or more input devices 320 can be configured to control operation of the static fluid measurement system 300. The signal electrodes 304, 306 and the sense electrodes 308, 310 can have any suitable configuration such as, for example, as individually attachable electrodes. As another example, one or more of the sense electrodes 308, 310 can be integrated into an airstream nozzle for ease of application to the patient, such as in the curved blade directional airstream nozzle (50-4-IMP) illustrated in FIG. 49. The curved blade directional airstream nozzle (50-4-IMP) is configured similar to the curved blade nozzle with a guide portion (50-4-WGP), except for further including a sense electrode (50-4-SE) corresponding to one of the sense electrodes 308, 310.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for treating fluid stasis, the system comprising:
   an airstream nozzle comprising an airstream nozzle inlet configured to receive an airflow and an airstream nozzle outlet orifice configured to output an airstream generated from the airflow, wherein the airstream is configured to be directed onto a skin of a patient to induce shear-thinning of static fluid and/or movement of static fluid toward one or more natural drainage areas for static fluid, wherein the airstream nozzle outlet orifice has an airstream nozzle outlet orifice cross-sectional area;
   an airflow hose configured for supplying the airflow to the airstream nozzle; and
   an airflow generator operable to generate and output the airflow to the airflow hose at a flow rate in a range from 1.3 $m^3$/min to 7.1 $m^3$/min, wherein a ratio of the flow rate to the airstream nozzle outlet orifice cross-sectional area is in a range from 0.004 ($m^3$/min)/$mm^2$ to 0.020 ($m^3$/min)/$mm^2$, wherein the flow rate is at least 0.85 $m^3$/min, and wherein the airflow has a pressure in a range from 10,000 Pa to 35,000 Pa within the airstream nozzle upstream of the airstream nozzle outlet orifice.

2. The system of claim 1, wherein the airstream nozzle outlet orifice has a cross-sectional width and a cross-sectional length that is at least 2 times greater than a cross-sectional width.

3. The system of claim 2, wherein the airstream nozzle comprises a lower surface protrusion shaped for application against the skin to apply pressure to the skin to shear thin and/or move static fluid.

4. The system of claim 2, wherein the airstream nozzle comprises a roller configured to be rolled along the skin to apply a contact pressure to the skin to shear thin and/or move static fluid.

5. The system of claim 2, wherein the airstream nozzle comprises longitudinally extending side skirts configured to form a negative pressure channel between the airstream nozzle and the skin in which a negative pressure is formed as a result of the airstream via the negative pressure channel functioning as a venturi.

6. The system of claim 2, wherein the airstream nozzle comprises a turbulence channel that receives the airstream from the airstream nozzle outlet orifice and is configured to induce turbulence in the airstream.

7. The system of claim 1 further comprising a second airstream nozzle configured for detachable mounting to the airflow hose, wherein:
   the second airstream nozzle comprises a second airstream nozzle inlet configured to receive the airflow and a second airstream nozzle outlet orifice configured to output a second airstream generated from the airflow;
   the second airstream is configured to be directed onto the skin to induce shear-thinning of static fluid;
   the second airstream nozzle outlet orifice has a second airstream nozzle outlet orifice cross-sectional area; and
   a ratio of the flow rate to the second airstream nozzle outlet orifice cross-sectional area is in a range from 0.004 (m3/min)/mm2 to 0.020 (m3/min)/mm2.

8. The system of claim 7, wherein the second airstream nozzle comprises a rotating assembly that generates a pulsatile component of the second airstream, wherein the rotating assembly is configured to rotate around a rotational axis aligned with a flow direction of the airflow in the airstream nozzle.

9. The system of claim 1, wherein the airstream nozzle comprises a rotating assembly that generates a directionally varying component of the airstream, wherein the rotating assembly is configured to rotate around a rotational axis aligned with a flow direction of the airflow in the airstream nozzle.

10. A system for treating fluid stasis, the system comprising:
    an airstream nozzle comprising an airstream nozzle inlet configured to receive an airflow and an airstream nozzle outlet orifice configured to output an airstream generated from the airflow, wherein the airstream is configured to be directed onto a skin of a patient to induce shear-thinning of static fluid and/or movement of static fluid toward one or more natural drainage areas for static fluid, wherein the airstream nozzle outlet orifice has a airstream nozzle outlet orifice cross-sectional area;

an airflow hose configured for supplying the airflow to the airstream nozzle;

an airflow generator operable to generate and output the airflow to the airflow hose at a flow rate, wherein a ratio of the flow rate to the airstream nozzle outlet orifice cross-sectional area is in a range from 0.004 (m3/min)/mm2 to 0.020 (m3/min)/mm2, and wherein the flow rate is at least 0.85 m3/min;

a sensor configured to generate a sensor output signal indicative of an extent of static fluid within a tissue of the patient;

an output device; and a control unit configured to process the sensor output signal to determine the extent of static fluid within the tissue, wherein the control unit is configured to control operation of the output device to output a feedback indicative of the extent of static fluid within the tissue.

11. The system of claim 10, wherein the sensor comprises an impedance sensor.

12. A system for treating fluid stasis, the system comprising:

an airstream nozzle comprising an airstream nozzle inlet configured to receive an airflow and an airstream nozzle outlet orifice configured to output an airstream generated from the airflow, wherein the airstream is configured to be directed onto a skin of a patient to induce shear-thinning of static fluid and/or movement of static fluid toward one or more natural drainage areas for static fluid, wherein the airstream nozzle outlet orifice has an airstream nozzle outlet orifice cross-sectional area;

an airflow hose configured for supplying the airflow to the airstream nozzle;

an airflow generator operable to generate and output the airflow to the airflow hose at a flow rate, wherein a ratio of the flow rate to the airstream nozzle outlet orifice cross-sectional area is in a range from 0.004 (m3/min)/mm2 to 0.020 (m3/min)/mm2, and wherein the flow rate is at least 0.85 m3/min;

an image sensor configured to generate skin movement image data for a region of the skin of the patient having induced movements resulting from directing the airstream onto the skin of the patient;

an output device; and a control unit configured to process the skin movement image data to estimate an extent of static fluid within a tissue underlying the region of the skin of the patient, wherein the control unit is configured to control operation of the output device to output a feedback indicative of the extent of static fluid within the tissue.

13. A method of treating fluid stasis, the method comprising:

outputting an airstream from an airstream nozzle onto a skin of a patient to shear-thin static fluid, condition one or more natural drainage regions for uptake of static fluid, and/or move static fluid toward one or more natural drainage regions for static fluid, wherein an airflow used to generate the airstream induces rotation of a rotatable component of the airstream nozzle about a rotational axis that is aligned with the airflow, and wherein the airstream comprises a pulsatile component or a directionally varying component; and assessing movement of the skin induced by the airstream to determine when a desired amount of static fluid has been moved toward the one or more natural drainage regions.

14. The method of claim 13, further comprising moving the airstream nozzle toward the one or more natural drainage regions for static fluid one or more times.

15. The method of claim 13, wherein outputting the airstream comprises orienting the airstream nozzle so that an angle between a direction of the airstream leaving the airstream nozzle and the skin is in a range from 0 degrees to 60 degrees.

16. The method of claim 13, wherein the airstream comprises the pulsatile component.

17. The method of claim 13, wherein the airstream comprises the directionally varying component.

18. The method of claim 13, further comprising outputting a second airstream from a second airstream nozzle onto the skin to shear-thin static fluid.

19. The method of claim 13, further comprising:

generating, by a fluid sensor, a fluid sensor output signal indicative of an extent of static fluid within a treated tissue of the patient;

processing the fluid sensor output signal to determine the extent of static fluid within the treated tissue; and outputting a feedback indicative of the extent of static fluid within the treated tissue.

20. The method of claim 19, wherein the fluid sensor comprises an impedance sensor.

21. The method of claim 13, further comprising:

generating, via an image sensor, skin movement image data for a region of the skin of the patient having induced movements induced by the airstream;

processing the skin movement image data to estimate an extent of static fluid within a tissue underlying the region of the skin of the patient; and outputting a feedback indicative of the extent of static fluid within the tissue underlying the region of the skin of the patient.

22. The system of claim 10, wherein the sensor comprises a photoplethysmography sensor.

23. The system of claim 10, wherein the sensor comprises an ultrasound sensor.

24. The system of claim 10, wherein the sensor comprises a temperature sensor.

* * * * *